(12) United States Patent
Baker et al.

(10) Patent No.: US 7,339,031 B2
(45) Date of Patent: Mar. 4, 2008

(54) MODIFIED BOUGANIN PROTEINS, CYTOTOXINS AND METHODS AND USES THEREOF

(75) Inventors: Matthew Baker, Cambridge (GB); Francis J. Carr, Aberdeenshire (GB); Koen Hellendoorn, Suffolk (GB); Jeannick Cizeau, Manitoba (CA); Glen Christopher MacDonald, Manitoba (CA); Joycelyn Entwistle, Manitoba (CA); Denis Georges Bosc, Manitoba (CA); Nicholas Ronald Glover, Ontario (CA)

(73) Assignee: Merck Patent GmbH, Darmstadt (DE)

( * ) Notice: Subject to any disclaimer, the term of this patent is extended or adjusted under 35 U.S.C. 154(b) by 97 days.

(21) Appl. No.: 11/084,080

(22) Filed: Mar. 18, 2005

(65) Prior Publication Data

US 2005/0238642 A1 Oct. 27, 2005

Related U.S. Application Data

(60) Provisional application No. 60/554,580, filed on Mar. 19, 2004, provisional application No. 60/630,571, filed on Nov. 26, 2004.

(51) Int. Cl.
*C07K 14/00* (2006.01)
*C07K 16/40* (2006.01)
*C12P 21/04* (2006.01)

(52) U.S. Cl. .................. 530/350; 435/69.7; 530/389.1; 530/388.26

(58) Field of Classification Search .................... None
See application file for complete search history.

(56) References Cited

U.S. PATENT DOCUMENTS 6,680,296 B1 1/2004 Stirpe et al.

FOREIGN PATENT DOCUMENTS

| WO | WO 98/52976 | 11/1998 |
|---|---|---|
| WO | WO 98/58678 | 12/1998 |
| WO | WO 00/34317 | 6/2000 |
| WO | WO 02/069232 A2 | 9/2002 |
| WO | WO 02/079415 | 10/2002 |
| WO | WO 03/103715 A1 | 12/2003 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
di Paolo et al, A recombinant immunotoxin derived from a humanized epithelial cell adhesion molecule-specific single-chain antibody fragment has potent and selective antitumor activity. Clin Cancer Res. Jul. 2003;9(7):2837-48. Erratum in: Clin Cancer Res. Apr. 1, 2004;10(7):2579.*
Den Hartog, M T et al. (2002), Cloning and expression of cDNA coding for bouganin, *Eur J Biochem,* 269(6):1172-1179.

* cited by examiner

*Primary Examiner*—Sheridan Swope
(74) *Attorney, Agent, or Firm*—Dann, Dorfman, Herrell & Skillman, P.C.; Robert C. Netter

(57) ABSTRACT

The invention provides modified forms of bouganin protein having biological activity and a reduced propensity to activate human T cells as compared to the non-modified bouganin protein. The invention also provides T-cell epitope peptides of bouganin, and modified T-cell epitope peptides of bouganin which have a reduced propensity to activate human T cells as compared to the non-modified T-cell epitope peptide. The invention also provides cytotoxins having the having a ligand that binds to a cancer cells attached to the modified bouganin proteins. Also provided are methods of inhibiting or destroying mammalian cancer cells using the cytotoxins of the invention and pharmaceutical compositions for treating human cancer.

19 Claims, 35 Drawing Sheets

FIGURE 1

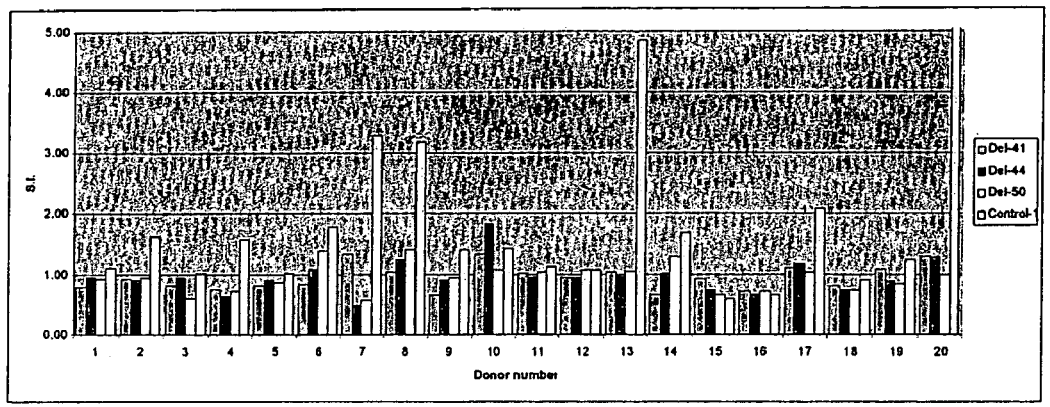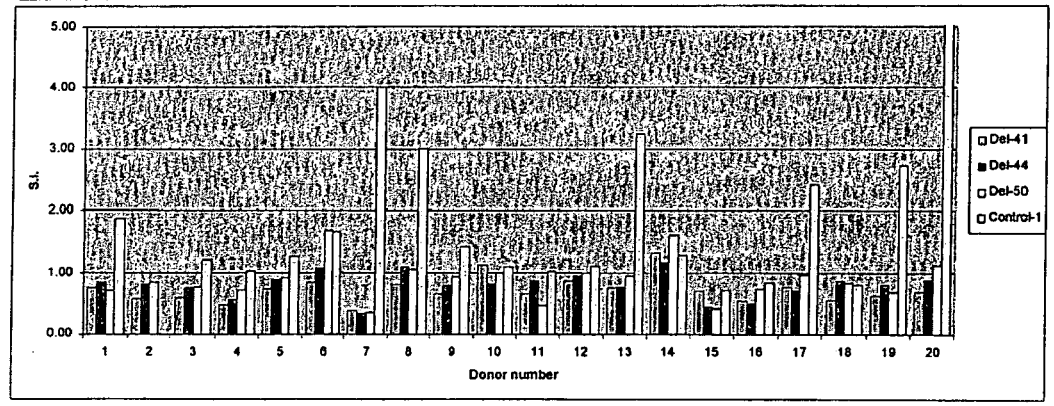
FIGURE 2

GAATTCCTGCAGGTCTATGGAACGATAAATGCCCATGAAAATTCTATTTCAAGGAGACAGTCATAATGAAATACCTATTGCCTAC 85
                                                                        |—— PelB ——

M  K  Y  L  L  P  T

GGCAGCCGCTGGATTGTTATTACTCGCTGCCCAACCAGCGATGGCGGAAGTACAGCTGGTTCAGTCCGGCCCGGGTCTTGTTCAA 170
|—————————— PelB ——————————|————— start of VH —————▶

A  A  A  G  L  L  L  L  A  A  Q  P  A  M  A  E  V  Q  L  V  Q  S  G  P  G  L  V  Q

CCGGGTGGTTCCGTTCGTATCTCTTGCGCTGCTTCTGGTTACACGTTCACCAACTACGGCATGAACTGGGTCAAACAGGCTCCGG 255

P  G  G  S  V  R  I  S  C  A  A  S  G  Y  T  F  T  N  Y  G  M  N  W  V  K  Q  A  P

GTAAAGGCCTGGAATGGATGGGCTGGATCAACACCTACACCGGTGAATCCACCTACGCTGACTCCTTCAAAGGTCGCTTCACTTT 340

G  K  G  L  E  W  M  G  W  I  N  T  Y  T  G  E  S  T  Y  A  D  S  F  K  G  R  F  T  F

CTCCCTCGACACAAGTGCTAGTGCTGCATACCTCCAAATCAACTCGCTGCGTGCAGAGGATACAGCAGTCTATTACTGCGCCCGT 425

S  L  D  T  S  A  S  A  A  Y  L  Q  I  N  S  L  R  A  E  D  T  A  V  Y  Y  C  A  R

TTCGCTATCAAAGGTGACTACTGGGGTCAAGGCACGCTGCTGACCGTTTCCTCGGCTAGCACCAAAGGCCCATCGGTCTTCCCCC 510
                                       |—— end of VH ——|————— start of CH —————▶

F  A  I  K  G  D  Y  W  G  Q  G  T  L  L  T  V  S  S  A  S  T  K  G  P  S  V  F  P

TGGCACCCTCCTCCAAGAGCACCTCTGGGGGCACAGCGGCCCTGGGCTGCCTGGTCAAGGACTACTTCCCCGAACCGGTGACGGT 595

L  A  P  S  S  K  S  T  S  G  G  T  A  A  L  G  C  L  V  K  D  Y  F  P  E  P  V  T  V

GTCGTGGAACTCAGGCGCCCTGACCAGCGGCGTGCACACCTTCCCGGCTGTCCTACAGTCCTCAGGACTCTACTCCCTCAGCAGC 680

S  W  N  S  G  A  L  T  S  G  V  H  T  F  P  A  V  L  Q  S  S  G  L  Y  S  L  S  S

GTGGTGACCGTGCCCTCCAGCAGCTTGGGCACCCAGACCTACATCTGCAACGTGAATCACAAGCCCAGCAACACCAAGGTGGACA 765

V  V  T  V  P  S  S  S  L  G  T  Q  T  Y  I  C  N  V  N  H  K  P  S  N  T  K  V  D

AGAAAGTTGAGCCCAAATCTTGTACCAGGCACAGGCAGCCCAGAGGCTGGGAGCAGCTCTACAACACCGTGTCATTTAACCTTGG 850
|—— end of CH ——|———— Furin Linker ————|—— start of De-Bouganin156 ▶

K  K  V  E  P  K  S  C  T  R  H  R  Q  P  R  G  W  E  Q  L  Y  N  T  V  S  F N L G

AGAAGCTTATGAGTACCCCACTTTTATACAAGATTTGCGCAATGAATTGGCTAAGGGCACACCAGTATGTCAACTTCCAGTGACA 935

E A Y E Y P T F I Q D L R N E L A K G T P V C Q L P V T

CTACAAACCATAGCCGATGACAAGCGATTTGTTCTAGTTGATATCACTACGACCTCGAAGAAAACAGTTAAGGTTGCTATAGATG 1020

L Q T I A D D K R F V L V D I T T T S K K T V K V A I D

TGACAGATGTGTATGTTGTGGGTTATCAAGACAAATGGGATGGCAAAGATCGAGCTGTTTTCCTTGACAAGGTTCCTACTGTTGC 1105

V T D V Y V V G Y Q D K W D G K D R A V F L D K V P T V A

AACTAGTAAACTTTTCCCAGGGGTGACTAATCGTGTAACGTTAACATTTGATGGCAGCTATCAGAAACTTGTGAATGCTGCCAAA 1190

T S K L F P G V T N R V T L T F D G S Y Q K L V N A A K

GCTGATAGAAAGGCTCTCGAACTGGGGGTTAACAAATTGGAATTTTCCATTGAAGCAATCCATGGTAAAACGATAAATGGTCAAG 1275

A D R K A L E L G V N K L E F S I E A I H G K T I N G Q

AGGCACCCAAGTTCTTTCTTATTGTCATCCAAATGGTTTCAGAGGCAGCTCGGTTCAAATATATTGAGACTGAGGTGGTTGATAG 1360

E A A K F F L I V I Q M V S E A A R F K Y I E T E V V D R

AGGATTATATGGATCATTCAAACCTAATTTTAAAGTATTGAACTTGGAGAACAATTGGGGCGACATCTCTGATGCCATTCACAAA 1445

G L Y G S F K P N F K V L N L E N N W G D I S D A I H K

TCATCCCCACAATGTACCACTATTAATCCGGCACTTCAGTTGATAAGCCCCTCAAATGACCCATGGGTTGTAAATAAAGTGAGTC 1530

S S P Q C T T I N P A L Q L I S P S N D P W V V N K V S

FIGURE 3B

```
AAATTAGTCCCGATATGGGTATCCTTAAGTTTAAAAGCTCCAAATAGTGATCTAGAGTCGACCTGCAGGTCTATGGAACGATAAA  1615
                                    |— end of De-Bouganin156 —|
 Q  I  S  P  D  M  G  I  L  K  F  K  S  S  K  .  .

TGCCCATGAAAATTCTATTTCAAGGAGACAGTCATAATGAAATACCTATTGCCTACGGCAGCCGCTGGATTGTTATTACTCGCTG  1700
                                             |————————— PelB ——————————
                                             .M  K  Y  L  L  P  T  A  A  A  G  L  L  L  L  A

CCCAACCAGCGATGGCGCACCATCATCACCATCACGATATCCAGATGACCCAGTCCCCGTCCTCCCTGAGTGCTTCTGTTGGTGA  1785
———— PelB ————|    6xHis         |—— start of VL ——————▶
 A  Q  P  A  M  A  H  H  H  H  H  H  D  I  Q  M  T  Q  S  P  S  S  L  S  A  S  V  G  D CCGTGTTACCATCACCTGCCGTTCCACCAAATCCCTCCTGCACTCCAACGGTATCACCTACCTTTATTGGTATCAACAGAAACCG  1870
 R  V  T  I  T  C  R  S  T  K  S  L  L  H  S  N  G  I  T  Y  L  Y  W  Y  Q  Q  K  P GGTAAAGCTCCGAAACTTCTGATCTACCAGATGTCCAACCTGGCTTCCGGTGTTCCGTCTCGTTTCTCCAGTTCTGGTTCTGGTA  1955
 G  K  A  P  K  L  L  I  Y  Q  M  S  N  L  A  S  G  V  P  S  R  F  S  S  S  G  S  G CCGACTTCACCCTGACCATCTCTTCTCTGCAGCCGGAAGACTTCGCTACCTACTACTGCGCTCAGAACCTGGAAATCCCGCGTAC  2040
 T  D  F  T  L  T  I  S  S  L  Q  P  E  D  F  A  T  Y  Y  C  A  Q  N  L  E  I  P  R  T CTTCGGTCAGGGTACCAAAGTTGAACTTAAGCGCACTGTGGCTGCACCATCTGTCTTCATCTTCCCGCCATCTGATGAGCAGTTG  2125
            |—— end of VL ——|—————— start of CL ——————▶
 F  G  Q  G  T  K  V  E  L  K  R  T  V  A  A  P  S  V  F  I  F  P  P  S  D  E  Q  L AAATCTGGAACTGCCTCTGTTGTGTGCCTGCTGAATAACTTCTATCCCAGAGAGGCCAAAGTACAGTGGAAGGTGGATAACGCCC  2210
 K  S  G  T  A  S  V  V  C  L  L  N  N  F  Y  P  R  E  A  K  V  Q  W  K  V  D  N  A TCCAATCGGGTAACTCCCAGGAGAGTGTCACAGAGCAGGACAGCAAGGACAGCACCTACAGCCTCAGCAGCACCCTGACGCTGAG  2295
 L  Q  S  G  N  S  Q  E  S  V  T  E  Q  D  S  K  D  S  T  Y  S  L  S  S  T  L  T  L  S CAAAGCAGACTACGAGAAACACAAAGTCTACGCCTGCGAAGTCACCCATCAGGGCCTGAGCTCGCCCGTCACAAAGAGCTTCAAC  2380
 K  A  D  Y  E  K  H  K  V  Y  A  C  E  V  T  H  Q  G  L  S  S  P  V  T  K  S  F  N AGGGGAGAGTGTTAGTAGCTCGAG  2404
|—— end of CL ——|
 R  G  E  C
```

FIGURE 3B CONT.

Map of the expression vector. Inserts are ligated in 3302 vector using EcoRI and XhoI restriction sites.

VB5-845

```
GAATTCCTGCAGGTCTATGGAACGATAAATGCCCATGAAAATTCTATTTCAAGGAGACAGTCATAATGAAATACCTATTGCCTAC 85
                                                                    |———— PelB ————
                                                                     M  K  Y  L  L  P  T

GGCAGCCGCTGGATTGTTATTACTCGCTGCCCAACCAGCGATGGCGGAAGTACAGCTGGTTCAGTCCGGCCCGGGTCTTGTTCAA 170
———————————— PelB ————————————————|———— start of VH ————▶
 A  A  A  G  L  L  L  A  A  Q  P  A  M  A  E  V  Q  L  V  Q  S  G  P  G  L  V  Q CCGGGTGGTTCCGTTCGTATCTCTTGCGCTGCTTCTGGTTACACGTTCACCAACTACGGCATGAACTGGGTCAAACAGGCTCCGG 255
 P  G  G  S  V  R  I  S  C  A  A  S  G  Y  T  F  T  N  Y  G  M  N  W  V  K  Q  A  P GTAAAGGCCTGGAATGGATGGGCTGGATCAACACCTACACCGGTGAATCCACCTACGCTGACTCCTTCAAAGGTCGCTTCACTTT 340
 G  K  G  L  E  W  M  G  W  I  N  T  Y  T  G  E  S  T  Y  A  D  S  F  K  G  R  F  T  F CTCCCTCGACACAAGTGCTAGTGCTGCATACCTCCAAATCAACTCGCTGCGTGCAGAGGATACAGCAGTCTATTACTGCGCCCGT 425
 S  L  D  T  S  A  S  A  A  Y  L  Q  I  N  S  L  R  A  E  D  T  A  V  Y  Y  C  A  R TTCGCTATCAAAGGTGACTACTGGGGTCAAGGCACGCTGCTGACCGTTTCCTCGGCTAGCACCAAAGGCCCATCGGTCTTCCCCC 510
                                      |———— end of VH ————|———— start of CH ————▶
 F  A  I  K  G  D  Y  W  G  Q  G  T  L  L  T  V  S  S  A  S  T  K  G  P  S  V  F  P TGGCACCCTCCTCCAAGAGCACCTCTGGGGGCACAGCGGCCCTGGGCTGCCTGGTCAAGGACTACTTCCCCGAACCGGTGACGGT 595
 L  A  P  S  S  K  S  T  S  G  G  T  A  A  L  G  C  L  V  K  D  Y  F  P  E  P  V  T  V GTCGTGGAACTCAGGCGCCCTGACCAGCGGCGTGCACACCTTCCCGGCTGTCCTACAGTCCTCAGGACTCTACTCCCTCAGCAGC 680
 S  W  N  S  G  A  L  T  S  G  V  H  T  F  P  A  V  L  Q  S  S  G  L  Y  S  L  S  S GTGGTGACCGTGCCCTCCAGCAGCTTGGGCACCCAGACCTACATCTGCAACGTGAATCACAAGCCCAGCAACACCAAGGTGGACA 765
 V  V  T  V  P  S  S  S  L  G  T  Q  T  Y  I  C  N  V  N  H  K  P  S  N  T  K  V  D AGAAAGTTGAGCCCAAATCTTGTTAGTGATCTAGAGTCGACCTGCAGGTCTATGGAACGATAAATGCCCATGAAAATTCTATTTC 850
           |———— end of CH ————|
 K  K  V  E  P  K  S  C  .  .

AAGGAGACAGTCATAATGAAATACCTATTGCCTACGGCAGCCGCTGGATTGTTATTACTCGCTGCCCAACCAGCGATGGCGCACC 935
                                                  ———————— PelB ————————————|  6x  |
         M  K  Y  L  L  P  T  A  A  A  G  L  L  L  A  A  Q  P  A  M  A  H

ATCATCACCATCACGATATCCAGATGACCCAGTCCCCGTCCTCCCTGAGTGCTTCTGTTGGTGACCGTGTTACCATCACCTGCCG 1020
|  6xHis  |———— start of VL ————▶
 H  H  H  H  H  D  I  Q  M  T  Q  S  P  S  S  L  S  A  S  V  G  D  R  V  T  I  T  C  R TTCCACCAAATCCCTCCTGCACTCCAACGGTATCACCTACCTTTATTGGTATCAACAGAAACCGGGTAAAGCTCCGAAACTTCTG 1105
 S  T  K  S  L  L  H  S  N  G  I  T  Y  L  Y  W  Y  Q  Q  K  P  G  K  A  P  K  L  L
```

FIGURE 5B

```
ATCTACCAGATGTCCAACCTGGCTTCCGGTGTTCCGTCTCGTTTCTCCAGTTCTGGTTCTGGTACCGACTTCACCCTGACCATCT 1190
 I  Y  Q  M  S  N  L  A  S  G  V  P  S  R  F  S  S  S  G  S  G  T  D  F  T  L  T  I

CTTCTCTGCAGCCGGAAGACTTCGCTACCTACTACTGCGCTCAGAACCTGGAAATCCCGCGTACCTTCGGTCAGGGTACCAAAGT 1275
 S  S  L  Q  P  E  D  F  A  T  Y  Y  C  A  Q  N  L  E  I  P  R  T  F  G  Q  G  T  K  V

TGAACTTAAGCGCACTGTGGCTGCACCATCTGTCTTCATCTTCCCGCCATCTGATGAGCAGTTGAAATCTGGAACTGCCTCTGTT 1360
├─ end of VL ─┤├────── start of CL ──────▶
    E  L  K  R  T  V  A  A  P  S  V  F  I  F  P  P  S  D  E  Q  L  K  S  G  T  A  S  V GTGTGCCTGCTGAATAACTTCTATCCCAGAGAGGCCAAAGTACAGTGGAAGGTGGATAACGCCCTCCAATCGGGTAACTCCCAGG 1445
 V  C  L  L  N  N  F  Y  P  R  E  A  K  V  Q  W  K  V  D  N  A  L  Q  S  G  N  S  Q AGAGTGTCACAGAGCAGGACAGCAAGGACAGCACCTACAGCCTCAGCAGCACCCTGACGCTGAGCAAAGCAGACTACGAGAAACA 1530
 E  S  V  T  E  Q  D  S  K  D  S  T  Y  S  L  S  S  T  L  T  L  S  K  A  D  Y  E  K  H CAAAGTCTACGCCTGCGAAGTCACCCATCAGGGCCTGAGCTCGCCCGTCACAAAGAGCTTCAACAGGGGAGAGTGTTAGTAGCTC 1615
                                         ├────────── end of CL ──────────┤
 K  V  Y  A  C  E  V  T  H  Q  G  L  S  S  P  V  T  K  S  F  N  R  G  E  C  .  .

GAG 1618
```

FIGURE 5B CONT.

```
GAATTCCTGCAGGTCTATGGAACGATAAATGCCCATGAAAATTCTATTTCAAGGAGACAGTCATAATGAAATACCTATTGCCTAC  85
                                                                        |—— PelB ———
                                                                         M  K  Y  L  L  P  T

GGCAGCCGCTGGATTGTTATTACTCGCTGCCCAACCAGCGATGGCGCACCATCATCACCATCACGAAGTACAGCTGGTTCAGTCC  170
———————————— PelB ——————————————|[    6xHis    ]——— start of VH ———▶
 A  A  A  G  L  L  L  A  A  Q  P  A  M  A  H  H  H  H  H  H  E  V  Q  L  V  Q  S GGCCCGGGTCTTGTTCAACCGGGTGGTTCCGTTCGTATCTCTTGCGCTGCTTCTGGTTACACGTTCACCAACTACGGCATGAACT  255
 G  P  G  L  V  Q  P  G  G  S  V  R  I  S  C  A  A  S  G  Y  T  F  T  N  Y  G  M  N GGGTCAAACAGGCTCCGGGTAAAGGCCTGGAATGGATGGGCTGGATCAACACCTACACCGGTGAATCCACCTACGCTGACTCCTT  340
 W  V  K  Q  A  P  G  K  G  L  E  W  M  G  W  I  N  T  Y  T  G  E  S  T  Y  A  D  S  F CAAAGGTCGCTTCACTTTCTCCCTCGACACAAGTGCTAGTGCTGCATACCTCCAAATCAACTCGCTGCGTGCAGAGGATACAGCA  425
 K  G  R  F  T  F  S  L  D  T  S  A  S  A  A  Y  L  Q  I  N  S  L  R  A  E  D  T  A GTCTATTACTGCGCCCGTTTCGCTATCAAAGGTGACTACTGGGGTCAAGGCACGCTGCTGACCGTTTCCTCGGCTAGCACCAAAG  510
                                                    |——— end of VH ————|—— start of CH ——
 V  Y  Y  C  A  R  F  A  I  K  G  D  Y  W  G  Q  G  T  L  L  T  V  S  S  A  S  T  K GCCCATCGGTCTTCCCCCTGGCACCCTCCTCCAAGAGCACCTCTGGGGGCACAGCGGCCCTGGGCTGCCTGGTCAAGGACTACTT  595
—— start of CH ———▶
 G  P  S  V  F  P  L  A  P  S  S  K  S  T  S  G  G  T  A  A  L  G  C  L  V  K  D  Y  F CCCCGAACCGGTGACGGTGTCGTGGAACTCAGGCGCCCTGACCAGCGGCGTGCACACCTTCCCGGCTGTCCTACAGTCCTCAGGA  680
 P  E  P  V  T  V  S  W  N  S  G  A  L  T  S  G  V  H  T  F  P  A  V  L  Q  S  S  G CTCTACTCCCTCAGCAGCGTGGTGACCGTGCCCTCCAGCAGCTTGGGCACCCAGACCTACATCTGCAACGTGAATCACAAGCCCA  765
 L  Y  S  L  S  S  V  V  T  V  P  S  S  S  L  G  T  Q  T  Y  I  C  N  V  N  H  K  P GCAACACCAAGGTGGACAAGAAAGTTGAGCCCAAATCTTGTTAGTGATCTAGAGTCGACCTGCAGGTCTATGGAACGATAAATGC  850
                                      |——————— end of CH ———————|
 S  N  T  K  V  D  K  K  V  E  P  K  S  C  . .

CCATGAAAATTCTATTTCAAGGAGACAGTCATAATGAAATACCTATTGCCTACGGCAGCCGCTGGATTGTTATTACTCGCTGCCC  935
                                                        |————————— PelB ——————————
                                      M  K  Y  L  L  P  T  A  A  A  G  L  L  L  L  A  A

AACCAGCGATGGCGGATATCCAGATGACCCAGTCCCCGTCCTCCCTGAGTGCTTCTGTTGGTGACCGTGTTACCATCACCTGCCG  1020
——— PelB ———|—— start of VL ———▶
 Q  P  A  M  A  D  I  Q  M  T  Q  S  P  S  S  L  S  A  S  V  G  D  R  V  T  I  T  C  R TTCCACCAAATCCCTCCTGCACTCCAACGGTATCACCTACCTTTATTGGTATCAACAGAAACCGGGTAAAGCTCCGAAACTTCTG  1105
 S  T  K  S  L  L  H  S  N  G  I  T  Y  L  Y  W  Y  Q  Q  K  P  G  K  A  P  K  L  L
```

FIGURE 6B

```
ATCTACCAGATGTCCAACCTGGCTTCCGGTGTTCCGTCTCGTTTCTCCAGTTCTGGTTCTGGTACCGACTTCACCCTGACCATCT 1190
 I  Y  Q  M  S  N  L  A  S  G  V  P  S  R  F  S  S  S  G  S  G  T  D  F  T  L  T  I

CTTCTCTGCAGCCGGAAGACTTCGCTACCTACTACTGCGCTCAGAACCTGGAAATCCCGCGTACCTTCGGTCAGGGTACCAAAGT 1275
 S  S  L  Q  P  E  D  F  A  T  Y  Y  C  A  Q  N  L  E  I  P  R  T  F  G  Q  G  T  K  V

TGAACTTAAGCGCACTGTGGCTGCACCATCTGTCTTCATCTTCCCGCCATCTGATGAGCAGTTGAAATCTGGAACTGCCTCTGTT 1360
├─end of VL─┤├──────────start of CL──────────▶
 E  L  K  R  T  V  A  A  P  S  V  F  I  F  P  P  S  D  E  Q  L  K  S  G  T  A  S  V GTGTGCCTGCTGAATAACTTCTATCCCAGAGAGGCCAAAGTACAGTGGAAGGTGGATAACGCCCTCCAATCGGGTAACTCCCAGG 1445
 V  C  L  L  N  N  F  Y  P  R  E  A  K  V  Q  W  K  V  D  N  A  L  Q  S  G  N  S  Q AGAGTGTCACAGAGCAGGACAGCAAGGACAGCACCTACAGCCTCAGCAGCACCCTGACGCTGAGCAAAGCAGACTACGAGAAACA 1530
 E  S  V  T  E  Q  D  S  K  D  S  T  Y  S  L  S  S  T  L  T  L  S  K  A  D  Y  E  K  H CAAAGTCTACGCCTGCGAAGTCACCCATCAGGGCCTGAGCTCGCCCGTCACAAAGAGCTTCAACAGGGGAGAGTGTACCAGGCAC 1615
                                                            ├─end of CL─┤├Furin Link▪
 K  V  Y  A  C  E  V  T  H  Q  G  L  S  S  P  V  T  K  S  F  N  R  G  E  C  T  R  H AGGCAGCCCAGAGGCTGGGAGCAGCTCTACAACACCGTGTCATTTAACCTTGGAGAAGCTTATGAGTACCCCACTTTTATACAAG 1700
────────Furin Linker────────┤├─start of De-Bouganin156─▶
 R  Q  P  R  G  W  E  Q  L  Y  N  T  V  S  F  N  L  G  E  A  Y  E  Y  P  T  F  I  Q ATTTGCGCAATGAATTGGCTAAGGGCACACCAGTATGTCAACTTCCAGTGACACTACAAACCATAGCCGATGACAAGCGATTTGT 1785
 D  L  R  N  E  L  A  K  G  T  P  V  C  Q  L  P  V  T  L  Q  T  I  A  D  D  K  R  F  V TCTAGTTGATATCACTACGACCTCGAAGAAAACAGTTAAGGTTGCTATAGATGTGACAGATGTGTATGTTGTGGGTTATCAAGAC 1870
 L  V  D  I  T  T  T  S  K  K  T  V  K  V  A  I  D  V  T  D  V  Y  V  V  G  Y  Q  D AAATGGGATGGCAAAGATCGAGCTGTTTTCCTTGACAAGGTTCCTACTGTTGCAACTAGTAAACTTTTCCCAGGGGTGACTAATC 1955
 K  W  D  G  K  D  R  A  V  F  L  D  K  V  P  T  V  A  T  S  K  L  F  P  G  V  T  N GTGTAACGTTAACATTTGATGGCAGCTATCAGAAACTTGTGAATGCTGCCAAAGCTGATAGAAAGGCTCTCGAACTGGGGGTTAA 2040
 R  V  T  L  T  F  D  G  S  Y  Q  K  L  V  N  A  A  K  A  D  R  K  A  L  E  L  G  V  N CAAATTGGAATTTTCCATTGAAGCAATCCATGGTAAAACGATAAATGGTCAAGAGGCAGCCAAGTTCTTTCTTATTGTCATCCAA 2125
 K  L  E  F  S  I  E  A  I  H  G  K  T  I  N  G  Q  E  A  A  K  F  F  L  I  V  I  Q ATGGTTTCAGAGGCAGCTCGGTTCAAATATATTGAGACTGAGGTGGTTGATAGAGGATTATATGGATCATTCAAACCTAATTTTA 2210
 M  V  S  E  A  A  R  F  K  Y  I  E  T  E  V  V  D  R  G  L  Y  G  S  F  K  P  N  F AAGTATTGAACTTGGAGAACAATTGGGGCGACATCTCTGATGCCATTCACAAATCATCCCCACAATGTACCACTATTAATCCGGC 2295
 K  V  L  N  L  E  N  N  W  G  D  I  S  D  A  I  H  K  S  S  P  Q  C  T  T  I  N  P  A
```

FIGURE 6B CONT.

```
ACTTCAGTTGATAAGCCCCTCAAATGACCCATGGGTTGTAAATAAAGTGAGTCAAATTAGTCCCGATATGGGTATCCTTAAGTTT 2380
                                                    ╠═══ end of De-Bouganin156 ═══
   L   Q   L   I   S   P   S   N   D   P   W   V   V   N   K   V   S   Q   I   S   P   D   M   G   I   L   K   F AAAAGCTCCAAATAGTAGCTCGAG 2404
▪ end of De-Bouganin15
   K   S   S   K   .   .
```

FIGURE 6B CONT.

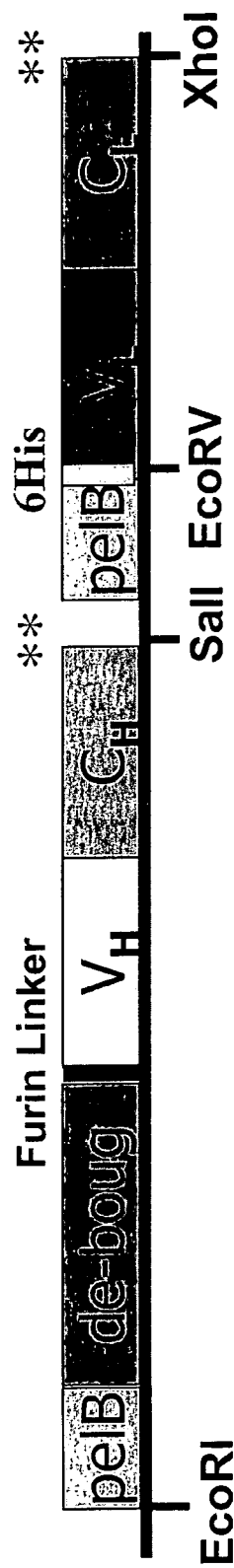
FIGURE 7A
FIGURE 7C

```
GAATTCCTGCAGGTCTATGGAACGATAAATGCCCATGAAAATTCTATTTCAAGGAGACAGTCATAATGAAATACCTATTGCCTAC  85
                                                                     |——— PelB ———
                                                             M  K  Y  L  L  P  T
GGCAGCCGCTGGATTGTTATTACTCGCTGCCCAACCAGCGATGGCGTACAACACCGTGTCATTTAACCTTGGAGAAGCTTATGAG  170
——————————————— PelB ———————————————|——— start of De-Bouganin156 ————————▶
  A  A  A  G  L  L  L  L  A  A  Q  P  A  M  A  Y  N  T  V  S  F  N  L  G  E  A  Y  E
TACCCCACTTTTATACAAGATTTGCGCAATGAATTGGCTAAGGGCACACCAGTATGTCAACTTCCAGTGACACTACAAACCATAG  255
  Y  P  T  F  I  Q  D  L  R  N  E  L  A  K  G  T  P  V  C  Q  L  P  V  T  L  Q  T  I
CCGATGACAAGCGATTTGTTCTAGTTGATATCACTACGACCTCGAAGAAAACAGTTAAGGTTGCTATAGATGTGACAGATGTGTA  340
  A  D  D  K  R  F  V  L  V  D  I  T  T  T  S  K  K  T  V  K  V  A  I  D  V  T  D  V  Y
TGTTGTGGGTTATCAAGACAAATGGGATGGCAAAGATCGAGCTGTTTTCCTTGACAAGGTTCCTACTGTTGCAACTAGTAAACTT  425
    V  V  G  Y  Q  D  K  W  D  G  K  D  R  A  V  F  L  D  K  V  P  T  V  A  T  S  K  L
TTCCCAGGGGTGACTAATCGTGTAACGTTAACATTTGATGGCAGCTATCAGAAACTTGTGAATGCTGCCAAAGCTGATAGAAAGG  510
  F  P  G  V  T  N  R  V  T  L  T  F  D  G  S  Y  Q  K  L  V  N  A  A  K  A  D  R  K
CTCTCGAACTGGGGGTTAACAAATTGGAATTTTCCATTGAAGCAATCCATGGTAAAACGATAAATGGTCAAGAGGCAGCCAAGTT  595
  A  L  E  L  G  V  N  K  L  E  F  S  I  E  A  I  H  G  K  T  I  N  G  Q  E  A  A  K  F
CTTTCTTATTGTCATCCAAATGGTTTCAGAGGCAGCTCGGTTCAAATATATTGAGACTGAGGTGGTTGATAGAGGATTATATGGA  680
    F  L  I  V  I  Q  M  V  S  E  A  A  R  F  K  Y  I  E  T  E  V  V  D  R  G  L  Y  G
TCATTCAAACCTAATTTTAAAGTATTGAACTTGGAGAACAATTGGGGCGACATCTCTGATGCCATTCACAAATCATCCCCACAAT  765
  S  F  K  P  N  F  K  V  L  N  L  E  N  N  W  G  D  I  S  D  A  I  H  K  S  S  P  Q
GTACCACTATTAATCCGGCACTTCAGTTGATAAGCCCCTCAAATGACCCATGGGTTGTAAATAAAGTGAGTCAAATTAGTCCCGA  850
  C  T  T  I  N  P  A  L  Q  L  I  S  P  S  N  D  P  W  V  V  N  K  V  S  Q  I  S  P  D
TATGGGTATCCTTAAGTTTAAAAGCTCCAAAACCAGGCACAGGCAGCCCAGAGGCTGGGAGCAGCTCGAAGTACAGCTGGTTCAG  935
|—— end of De-Bouganin156 ——|——————— Furin Linker ——————————|—— start of VH ——▶
  M  G  I  L  K  F  K  S  S  K  T  R  H  R  Q  P  R  G  W  E  Q  L  E  V  Q  L  V  Q
TCCGGCCCGGGTCTTGTTCAACCGGGTGGTTCCGTTCGTATCTCTTGCGCTGCTTCTGGTTACACGTTCACCAACTACGGCATGA  1020
  S  G  P  G  L  V  Q  P  G  G  S  V  R  I  S  C  A  A  S  G  Y  T  F  T  N  Y  G  M
ACTGGGTCAAACAGGCTCCGGGTAAAGGCGTGGAATGGATGGGCTGGATCAACACCTACACCGGTGAATCCACCTACGCTGACTC  1105
  N  W  V  K  Q  A  P  G  K  G  L  E  W  M  G  W  I  N  T  Y  T  G  E  S  T  Y  A  D  S
CTTCAAAGGTCGCTTCACTTTCTCCCTCGACACAAGTGCTAGTGCTGCATACCTCCAAATCAACTCGCTGCGTGCAGAGGATACA  1190
  F  K  G  R  F  T  F  S  L  D  T  S  A  S  A  A  Y  L  Q  I  N  S  L  R  A  E  D  T
GCAGTCTATTACTGCGCCCGTTTCGCTATCAAAGGTGACTACTGGGGTCAAGGCACGCTGCTGACCGTTTCCTCGGCTAGCACCA  1275
                                                                 |—— end of VH ——|▪start of CH ▪
  A  V  V  Y  Y  C  A  R  F  A  I  K  G  D  Y  W  G  Q  G  T  L  L  T  V  S  S  A  S  T
AAGGCCCATCGGTCTTCCCCCTGGCACCCTCCTCCAAGAGCACCTCTGGGGGCACAGCGGCCCTGGGCTGCCTGGTCAAGGACTA  1360
——— start of CH ——▶
  K  G  P  S  V  F  P  L  A  P  S  S  K  S  T  S  G  G  T  A  A  L  G  C  L  V  K  D  Y
CTTCCCCGAACCGGTGACGGTGTCGTGGAACTCAGGCGCCCTGACCAGCGGCGTGCACACCTTCCCGGCTGTCCTACAGTCCTCA  1445
    F  P  E  P  V  T  V  S  W  N  S  G  A  L  T  S  G  V  H  T  F  P  A  V  L  Q  S  S
```

FIGURE 7B

```
GGACTCTACTCCCTCAGCAGCGTGGTGACCGTGCCCTCCAGCAGCTTGGGCACCCAGACCTACATCTGCAACGTGAATCACAAGC 1530
 G  L  Y  S  L  S  S  V  V  T  V  P  S  S  S  L  G  T  Q  T  Y  I  C  N  V  N  H  K

CCAGCAACACCAAGGTGGACAAGAAAGTTGAGCCCAAATCTTGTTAGTGATCTAGAGTCGACCTGCAGGTCTATGAACGATAAA 1615
                            |━━━ end of CH ━━━|
 P  S  N  T  K  V  D  K  K  V  E  P  K  S  C  .  .

TGCCCATGAAAATTCTATTTCAAGGAGACAGTCATAATGAAATACCTATTGCCTACGGCAGCCGCTGGATTGTTATTACTCGCTG 1700
                                       |━━━━━━━━━━━ PelB ━━━━━━━━━━━
                               M  K  Y  L  L  P  T  A  A  A  G  L  L  L  L  A

CCCAACCAGCGATGGCGCACCATCATCACCATCACGATATCCAGATGACCCAGTCCCCGTCCTCCCTGAGTGCTTCTGTTGGTGA 1785
━━━ PelB ━━|━━━━━━ 6xHis ━━━━━|━━━━━ start of VL ━━━━━▶
 A  Q  P  A  M  A  H  H  H  H  H  H  D  I  Q  M  T  Q  S  P  S  S  L  S  A  S  V  G  D CCGTGTTACCATCACCTGCCGTTCCACCAAATCCCTCCTGCACTCCAACGGTATCACCTACCTTTATTGGTATCAACAGAAACCG 1870
  R  V  T  I  T  C  R  S  T  K  S  L  L  H  S  N  G  I  T  Y  L  Y  W  Y  Q  Q  K  P GGTAAAGCTCCGAAACTTCTGATCTACCAGATGTCCAACCTGGCTTCCGGTGTTCCGTCTCGTTTCTCCAGTTCTGGTTCTGGTA 1955
  G  K  A  P  K  L  L  I  Y  Q  M  S  N  L  A  S  G  V  P  S  R  F  S  S  S  G  S  G CCGACTTCACCCTGACCATCTCTTCTCTGCAGCCGGAAGACTTCGCTACCTACTACTGCGCTCAGAACCTGGAAATCCCCCGTAC 2040
  T  D  F  T  L  T  I  S  S  L  Q  P  E  D  F  A  T  Y  Y  C  A  Q  N  L  E  I  P  R  T CTTCGGTCAGGGTACCAAAGTTGAACTTAAGCGCACTGTGGCTGCACCATCTGTCTTCATCTTCCCGCCATCTGATGAGCAGTTG 2125
            |━━━━━ end of VL ━━━━━|━━━━━ start of CL ━━━━━▶
  F  G  Q  G  T  K  V  E  L  K  R  T  V  A  A  P  S  V  F  I  F  P  P  S  D  E  Q  L AAATCTGGAACTGCCTCTGTTGTGTGCCTGCTGAATAACTTCTATCCCAGAGAGGCCAAAGTACAGTGGAAGGTGGATAACGCCC 2210
  K  S  G  T  A  S  V  V  C  L  L  N  N  F  Y  P  R  E  A  K  V  Q  W  K  V  D  N  A TCCAATCGGGTAACTCCCAGGAGAGTGTCACAGAGCAGGACAGCAAGGACAGCACCTACAGCCTCAGCAGCACCCTGACGCTGAG 2295
  L  Q  S  G  N  S  Q  E  S  V  T  E  Q  D  S  K  D  S  T  Y  S  L  S  S  T  L  T  L  S CAAAGCAGACTACGAGAAACACAAAGTCTACGCCTGCGAAGTCACCCATCAGGGCCTGAGCTCGCCCGTCACAAAGAGCTTCAAC 2380
  K  A  D  Y  E  K  H  K  V  Y  A  C  E  V  T  H  Q  G  L  S  S  P  V  T  K  S  F  N AGGGGAGAGTGTTAGTAGCTCGAG 2404
|━━━ end of CL ━━━|
  R  G  E  C  .  .
```

FIGURE 7B CONT.

VB6-845-NV_L-de-bouganin

EcoRI — pelB — 6His — V_H — C_H —  — SalI — pelB — de-boug — Furin Linker — V_L — EcoRV — C_L —  — XhoI

FIGURE 8A

6xHis — V_H — C_H —S—S— C_L — V_L — Furin Linker — de-boug

FIGURE 8C

```
GAATTCCTGCAGGTCTATGGAACGATAAATGCCCATGAAAATTCTATTTCAAGGAGACAGTCATAATGAAATACCTATTGCCTAC  85
                                                                 |━━━ PelB ━━━
                                                                  M  K  Y  L  L  P  T

GGCAGCCGCTGGATTGTTATTACTCGCTGCCCAACCAGCGATGGCGCACCATCATCACCATCACGAAGTACAGCTGGTTCAGTCC  170
━━━━━━━━━━ PelB ━━━━━━━━━━|━━━━━━ 6xHis ━━━━━|━ start of VH ━━▶
 A  A  A  G  L  L  L  L  A  A  Q  P  A  M  A  H  H  H  H  H  H  E  V  Q  L  V  Q  S GGCCCGGGTCTTGTTCAACCGGGTGGTTCCGTTCGTATCTCTTGCGCTGCTTCTGGTTACACGTTCACCAACTACGGCATGAACT  255
 G  P  G  L  V  Q  P  G  G  S  V  R  I  S  C  A  A  S  G  Y  T  F  T  N  Y  G  M  N GGGTCAAACAGGCTCCGGGTAAAGGCCTGGAATGGATGGGCTGGATCAACACCTACACCGGTGAATCCACCTACGCTGACTCCTT  340
 G  V  K  Q  A  P  G  K  G  L  E  W  M  G  W  I  N  T  Y  T  G  E  S  T  Y  A  D  S  F CAAAGGTCGCTTCACTTTCTCCCTCGACACAAGTGCTAGTGCTGCATACCTCCAAATCAACTCGCTGCGTGCAGAGGATACAGCA  425
 K  G  R  F  T  F  S  L  D  T  S  A  S  A  A  Y  L  Q  I  N  S  L  R  A  E  D  T  A GTCTATTACTGCGCCCGTTTCGCTATCAAAGGTGACTACTGGGGTCAAGGCACGCTGCTGACCGTTTCCTCGGCTAGCACCAAAG  510
                                   |━━━ end of VH ━━━|━ start of CH ━━
 V  Y  Y  C  A  R  F  A  I  K  G  D  Y  W  G  Q  G  T  L  L  T  V  S  S  A  S  T  K GCCCATCGGTCTTCCCCCTGGCACCCTCCTCCAAGAGCACCTCTGGGGGCACAGCGGCCCTGGGCTGCCTGGTCAAGGACTACTT  595
━━━ start of CH ━━▶
 G  P  S  V  F  P  L  A  P  S  S  K  S  T  S  G  G  T  A  A  L  G  C  L  V  K  D  Y  F CCCCGAACCGGTGACGGTGTCGTGGAACTCAGGCGCCCTGACCAGCGGCGTGCACACCTTCCCGGCTGTCCTACAGTCCTCAGGA  680
 P  E  P  V  T  V  S  W  N  S  G  A  L  T  S  G  V  H  T  F  P  A  V  L  Q  S  S  G CTCTACTCCCTCAGCAGCGTGGTGACCGTGCCCTCCAGCAGCTTGGGCACCCAGACCTACATCTGCAACGTGAATCACAAGCCCA  765
 L  Y  S  L  S  S  V  V  T  V  P  S  S  S  L  G  T  Q  T  Y  I  C  N  V  N  H  K  P GCAACACCAAGGTGGACAAGAAAGTTGAGCCCAAATCTTGTTAGTGATCTAGAGTCGACCTGCAGGTCTATGGAACGATAAATGC  850
                             |━━━ end of CH ━━━|
 S  N  T  K  V  D  K  K  V  E  P  K  S  C  .  .

CCATGAAAATTCTATTTCAAGGAGACAGTCATAATGAAATACCTATTGCCTACGGCAGCCGCTGGATTGTTATTACTCGCTGCCC  935
                                         |━━━━━━━ PelB ━━━━━━━
                                           M  K  Y  L  L  P  T  A  A  A  G  L  L  L  L  A  A

AACCAGCGATGGCGTACAACACCGTGTCATTTAACCTTGGAGAAGCTTATGAGTACCCCACTTTTATACAAGATTTGCGCAATGA  1020
━━ PelB ━━|━━━━━ start of De-Bouganin156 ━━━━━━▶
 Q  P  A  M  A  Y  N  T  V  S  F  N  L  G  E  A  Y  E  Y  P  T  F  I  Q  D  L  R  N  E ATTGGCTAAGGGCACACCAGTATGTCAACTTCCAGTGACACTACAAACCATAGCCGATGACAAGCGATTTGTTCTAGTTGATATC  1105
 L  A  K  G  T  P  V  C  Q  L  P  V  T  L  Q  T  I  A  D  D  K  R  F  V  L  V  D  I ACTACGACCTCGAAGAAAACAGTTAAGGTTGCTATAGATGTGACAGATGTGTATGTTGTGGGTTATCAAGACAAATGGGATGGCA  1190
 T  T  T  S  K  K  T  V  K  V  A  I  D  V  T  D  V  Y  V  V  G  Y  Q  D  K  W  D  G AAGATCGAGCTGTTTTCCTTGACAAGGTTCCTACTGTTGCAACTAGTAAACTTTTCCCAGCGGTCACTAATCGTGTAACGTTAAC  1275
 K  D  R  A  V  F  L  D  K  V  P  T  V  A  T  S  K  L  F  P  G  V  T  N  R  V  T  L  T ATTTGATGGCAGCTATCAGAAACTTGTGAATGCTGCCAAAGCTGATAGAAAGGCTCTCGAACTGGGGGTTAACAAATTGGAATTT  1360
 F  D  G  S  Y  Q  K  L  V  N  A  A  K  A  D  R  K  A  L  E  L  G  V  N  K  L  E  F TCCATTGAAGCAATCCATGGTAAAACGATAAATGGTCAAGAGGCAGCCAAGTTCTTTCTTATTGTCATCCAAATGGTTTCAGACG  1445
 S  I  E  A  I  H  G  K  T  I  N  G  Q  E  A  A  K  F  F  L  I  V  I  Q  M  V  S  E
```

FIGURE 8B

```
CAGCTCGGTTCAAATATATTGAGACTGAGGTGGTTGATAGAGGATTATATGGATCATTCAAACCTAATTTTAAAGTATTGAACTT 1530
 A  A  R  F  K  Y  I  E  T  E  V  V  D  R  G  L  Y  G  S  F  K  P  N  F  K  V  L  N  L

GGAGAACAATTGGGGCGACATCTCTGATGCCATTCACAAATCATCCCCACAATGTACCACTATTAATCCGGCACTTCAGTTGATA 1615
  E  N  N  W  G  D  I  S  D  A  I  H  K  S  S  P  Q  C  T  T  I  N  P  A  L  Q  L  I

AGCCCCTCAAATGACCCATGGGTTGTAAATAAAGTGAGTCAAATTAGTCCCGATATGGGTATCCTTAAGTTTAAAAGCTCCAAAA 1700
  S  P  S  N  D  P  W  V  V  N  K  V  S  Q  I  S  P  D  M  G  I  L  K  F  K  S  S  K

CCAGGCACAGGCAGCCCAGAGGCTGGGAGCAGCTCGATATCCAGATGACCCAGTCCCCGTCCTCCCTGAGTGCTTCTGTTGGTGA 1785
━━━━━━━━━━━━━Furin Linker━━━━━━━━━┣━━━━━━━━━ start of VL ━━━━━━━━▶
 T  R  H  R  Q  P  R  G  W  E  Q  L  D  I  Q  M  T  Q  S  P  S  S  L  S  A  S  V  G  D CCGTGTTACCATCACCTGCCGTTCCACCAAATCCCTCCTGCACTCCAACGGTATCACCTACCTTTATTGGTATCAACAGAAACCG 1870
  R  V  T  I  T  C  R  S  T  K  S  L  L  H  S  N  G  I  T  Y  L  Y  W  Y  Q  Q  K  P GGTAAAGCTCCGAAACTTCTGATCTACCAGATGTCCAACCTGGCTTCCGGTGTTCCGTCTCGTTTCTCCAGTTCTGGTTCTGGTA 1955
  G  K  A  P  K  L  L  I  Y  Q  M  S  N  L  A  S  G  V  P  S  R  F  S  S  S  G  S  G CCGACTTCACCCTGACCATCTCTTCTCTGCAGCCGGAAGACTTCGCTACCTACTACTGCGCTCAGAACCTGGAAATCCCGCGTAC 2040
 T  D  F  T  L  T  I  S  S  L  Q  P  E  D  F  A  T  Y  Y  C  A  Q  N  L  E  I  P  R  T CTTCGGTCAGGGTACCAAAGTTGAACTTAAGCGCACTGTGGCTGCACCATCTGTCTTCATCTTCCCGCCATCTGATGAGCAGTTG 2125
┣━━━━━━end of VL ━━━━┫┣━━━━━━━━━━ start of CL ━━━━━━━━━▶
 F  G  Q  G  T  K  V  E  L  K  R  T  V  A  A  P  S  V  F  I  F  P  P  S  D  E  Q  L AAATCTGGAACTGCCTCTGTTGTGTGCCTGCTGAATAACTTCTATCCCAGAGAGGCCAAAGTACAGTGGAAGGTGGATAACGCCC 2210
 K  S  G  T  A  S  V  V  C  L  L  N  N  F  Y  P  R  E  A  K  V  Q  W  K  V  D  N  A TCCAATCGGGTAACTCCCAGGAGAGTGTCACAGAGCAGGACAGCAAGGACAGCACCTACAGCCTCAGCAGCACCCTGACGCTGAG 2295
 L  Q  S  G  N  S  Q  E  S  V  T  E  Q  D  S  K  D  S  T  Y  S  L  S  S  T  L  T  L  S CAAAGCAGACTACGAGAAACACAAAGTCTACGCCTGCGAAGTCACCCATCAGGGCCTGAGCTCGCCCGTCACAAAGAGCTTCAAC 2380
 K  A  D  Y  E  K  H  K  V  Y  A  C  E  V  T  H  Q  G  L  S  S  P  V  T  K  S  F  N AGGGGAGAGTGTTAGTAGCTCGAG 2404
┣━━━━end of CL━━━━┫
 R  G  E  C  .  .
```

FIGURE 8B CONT.

Competition Assay - VB6-845 and Proxinium - NIH:OVCAR-3

Conditions;
- 0.3x10$^6$ cells/group.
- VB6-845 and Proxinium concentrations mixed in equal volumes.
- 1h incubation on ice.
- 1/200 dilution of Rb a-Bouganin-biotin as 2nd Ab-1h on ice.
- fluorochrome - 1/120 dilution of streptavidin-cychrome-1/2h on ice.
- 100% bound - 0μg/mL Proxinium.

```
GAATTCCTGCAGGTCTATGGAACGATAAATGCCCATGAAAATTCTATTTCAAGGAGACAGTCATAATGAAATACCTATTGCCTAC 85
                                                                    |———— PelB ————|

M  K  Y  L  L  P  T
GGCAGCCGCTGGATTGTTATTACTCGCTGCCCAACCAGCGATGGCGGAAGTACAGCTGGTTCAGTCCGGCCCGGGTCTTGTTCAA 170
|——————————— PelB ——————————|————— start of VH —————▶

A  A  A  G  L  L  L  A  A  D  P  A  M  A  E  V  Q  L  V  Q  S  G  P  G  L  V  Q
CCGGGTGGTTCCGTTCGTATCTCTTGCGCTGCTTCTGGTTACACGTTCACCAACTACGGCATGAACTGGGTCAAACAGGCTCCGG 255

P  G  G  S  V  R  I  S  C  A  A  S  G  Y  T  F  T  N  Y  G  M  N  W  V  K  Q  A  P
GTAAAGGCCTGGAATGGATGGGCTGGATCAACACCTACACCGGTGAATCCACCTACGCTGACTCCTTCAAAGGTCGCTTCACTTT 340

G  K  G  L  E  W  M  G  W  I  N  T  Y  T  G  E  S  T  Y  A  D  S  F  K  G  R  F  T  F
CTCCCTCGACACAAGTGCTAGTGCTGCATACCTCCAAATCAACTCGCTGCGTGCAGAGGATACAGCAGTCTATTACTGCGCCCGT 425

S  L  D  T  S  A  S  A  A  Y  L  Q  I  N  S  L  R  A  E  D  T  A  V  Y  Y  C  A  R
TTCGCTATCAAAGGTGACTACTGGGGTCAAGGCACGCTGCTGACCGTTTCCTCGGCTAGCACCAAAGGCCCATCGGTCTTCCCCC 510
                                              |————— end of VH ————|————— start of CH —————▶

F  A  I  K  G  D  Y  W  G  Q  G  T  L  L  T  V  S  S  A  S  T  K  G  P  S  V  F  P
TGGCACCCTCCTCCAAGAGCACCTCTGGGGGCACAGCGGCCCTGGGCTGCCTGGTCAAGGACTACTTCCCCGAACCGGTGACGGT 595

L  A  P  S  S  K  S  T  S  G  G  T  A  A  L  G  C  L  V  K  D  Y  F  P  E  P  V  T  V
GTCGTGGAACTCAGGCGCCCTGACCAGCGGCGTGCACACCTTCCCGGCTGTCCTACAGTCCTCAGGACTCTACTCCCTCAGCAGC 680

S  W  N  S  G  A  L  T  S  G  V  H  T  F  P  A  V  L  Q  S  S  G  L  Y  S  L  S  S
GTGGTGACCGTGCCCTCCAGCAGCTTGGGCACCCAGACCTACATCTGCAACGTGAATCACAAGCCCAGCAACACCAAGGTGGACA 765

V  V  T  V  P  S  S  S  L  G  T  Q  T  Y  I  C  N  V  N  H  K  P  S  N  T  K  V  D
AGAAAGTTGAGCCCAAATCTTGTACCAGGCACAGGCAGCCCAGAGGCTGGGAGCAGCTCGGCCTGGACACCGTGAGCTTTAGCAC 850
|——— end of CH ———|—|————— Furin linker —————|————— start of Gelonin —————▶

K  K  V  E  P  K  S  C  T  R  H  R  Q  P  R  G  W  E  Q  L  G  L  D  T  V  S  F  S  T
TAAAGGTGCCACTTATATTACCTACGTGAATTTCTTGAATGAGCTACGAGTTAAATTGAAACCCGAAGGTAACAGCCATGGAATC 935

K  G  A  T  Y  I  T  Y  V  N  F  L  N  E  L  R  V  K  L  K  P  E  G  N  S  H  G  I
CCATTGCTGCGCAAAAAATGTGATGATCCTGGAAAGTGTTTCGTTTTGGTAGCGCTTTCAAATGACAATGGACAGTTGGCGGAAA 1020

P  L  L  R  K  K  C  D  D  P  G  K  C  F  V  L  V  A  L  S  N  D  N  G  Q  L  A  E
TAGCTATAGATGTTACAAGTGTTTATGTGGTGGGCTATCAAGTAAGAAACAGATCTTACTTCTTTAAAGATGCTCCAGATGCTGC 1105

```
TTACGAAGGCCTCTTCAAAAACACAATTAAAACAAGACTTCATTTTGGCGGCAGCTATCCCTCGCTGGAAGGTGAGAAGGCATAT 1190
  Y  E  G  L  F  K  N  T  I  K  T  R  L  H  F  G  G  S  Y  P  S  L  E  G  E  K  A  Y

AGAGAGACAACAGACTTGGGCATTGAACCATTAAGGATTGGCATCAAGAAACTTGATGAAAATGCGATAGACAATTATAAACCAA 1275
 R  E  T  T  D  L  G  I  E  P  L  R  I  G  I  K  K  L  D  E  N  A  I  D  N  Y  K  P

CGGAGATAGCTAGTTCTCTATTGGTTGTTATTCAAATGGTGTCTGAAGCAGCTCGATTCACCTTTATTGAGAACCAAATTAGAAA 1360
 T  E  I  A  S  S  L  L  V  V  I  Q  M  V  S  E  A  A  R  F  T  F  I  E  N  Q  I  R  N

TAACTTTCAACAGAGAATCCGCCCGACGAATAATACAATCAGCCTTGAGAATAAATGGGGTAAACTCTCGTTCCAGATCCGGACA 1445
  N  F  Q  Q  R  I  R  P  T  N  N  T  I  S  L  E  N  K  W  G  K  L  S  F  Q  I  R  T

TCAGGTGCAAATGGAATGTTTTCGGAGGCAGTTGAATTGGAACGTGCAAATGGCAAAAAATACTATGTCACCGCAGTTGATCAAG 1530
  S  G  A  N  G  M  F  S  E  A  V  E  L  E  R  A  N  G  K  K  Y  Y  V  T  A  V  D  Q

TAAAACCCAAAATAGCACTCTTGAAGTTCGTCGATAAAGATCCTAAATAGTGATCTAGAGTCGACCTGCAGGTCTATGGAACGAT 1615
                                     |———— end of Gelonin ————|
  V  K  P  K  I  A  L  L  K  F  V  D  K  D  P  K AAATGCCCATGAAAATTCTATTTCAAGGAGACAGTCATAATGAAATACCTATTGCCTACGGCAGCCGCTGGATTGTTATTACTCG 1700
                                              |———————————— PelB ————————————
                                                M  K  Y  L  L  P  T  A  A  A  G  L  L  L  L CTGCCCAACCAGCGATGGCGCACCATCATCACCATCACGATATCCAGATGACCCAGTCCCCGTCCTCCCTGAGTGCTTCTGTTGG 1785
———— PelB ————|——| 6xHis |———————— start of VL ————▶
 A  A  Q  P  A  M  A  H  H  H  H  H  H  D  I  Q  M  T  Q  S  P  S  S  L  S  A  S  V  G TGACCGTGTTACCATCACCTGCCGTTCCACCAAATCCCTCCTGCACTCCAACGGTATCACCTACCTTTATTGGTATCAACAGAAA 1870
  D  R  V  T  I  T  C  R  S  T  K  S  L  L  H  S  N  G  I  T  Y  L  Y  W  Y  Q  Q  K CCGGGTAAAGCTCCGAAACTTCTGATCTACCAGATGTCCAACCTGGCTTCCGGTGTTCCGTCTCGTTTCTCCAGTTCTGGTTCTG 1955
  P  G  K  A  P  K  L  L  I  Y  Q  M  S  N  L  A  S  G  V  P  S  R  F  S  S  S  G  S GTACCGACTTCACCCTGACCATCTCTTCTCTGCAGCCGGAAGACTTCGCTACCTACTACTGCGCTCAGAACCTGGAAATCCCGCG 2040
  G  T  D  F  T  L  T  I  S  S  L  Q  P  E  D  F  A  T  Y  Y  C  A  Q  N  L  E  I  P  R TACCTTCGGTCAGGGTACCAAAGTTGAACTTAAGCGCACTGTGGCTGCACCATCTGTCTTCATCTTCCCGCCATCTGATGAGCAG 2125
             |———— end of VL ————|———— start of CL ————▶
  T  F  G  Q  G  T  K  V  E  L  K  R  T  V  A  A  P  S  V  F  I  F  P  P  S  D  E  Q TTGAAATCTGGAACTGCCTCTGTTGTGTGCCTGCTGAATAACTTCTATCCCAGAGAGGCCAAAGTACAGTGGAAGGTGGATAACG 2210
  L  K  S  G  T  A  S  V  V  C  L  L  N  N  F  Y  P  R  E  A  K  V  Q  W  K  V  D  N CCCTCCAATCGGGTAACTCCCAGGAGAGTGTCACAGAGCAGGACAGCAAGGACAGCACCTACAGCCTCAGCAGCACCCTGACGCT 2295
  A  L  Q  S  G  N  S  Q  E  S  V  T  E  Q  D  S  K  D  S  T  Y  S  L  S  S  T  L  T  L
```

FIGURE 14C CONT.

```
GAGCAAAGCAGACTACGAGAAACACAAAGTCTACGCCTGCGAAGTCACCCATCAGGGCCTGAGCTCGCCCGTCACAAAGAGCTTC 2380
  S  K  A  D  Y  E  K  H  K  V  Y  A  C  E  V  T  H  Q  G  L  S  S  P  V  T  K  S  F

AACAGGGAGAGTGTTAGTAGCTCGAG 2407
|——— end of CL ———|
  N  R  G  E  C  .  .
```

FIGURE 14C CONT.

```
GAATTCCTGCAGGTCTATGGAACGATAAATGCCCATGAAAATTCTATTTCAAGGAGACAGTCATAATGAAATACCTATTGCCTAC  85
                                                                    |━━━━ PelB ━━━━
                                                                    M  K  Y  L  L  P  T

GGCAGCCGCTGGATTGTTATTACTCGCTGCCCAACCAGCGATGGCGCAGGTGCAGCTGGTGGAGTCTGGGGGAGGCGTGGTCCAG 170
━━━━━━━━━━━━━━━ PelB ━━━━━━━━━━━━━|━━━━━ start of VH ━━━━▶

A  A  A  G  L  L  L  L  A  A  Q  P  A  M  A  Q  V  Q  L  V  E  S  G  G  G  V  V  Q

CCTGGGAGGTCCCTGAGACTCTCCTGTGCAGCCTCTGGATTCCCCTTCAGAAGCTTTGCTATGCACTGGGTCCGCCAGGCTCTAG 255

P  G  R  S  L  R  L  S  C  A  A  S  G  F  P  F  R  S  F  A  M  H  W  V  R  Q  A  L

GCAAGGGGCTGGAGTGGGTGGCAGTTATATCATATGATGGAAGCACTAAATACTACGCAGACTCCGTGAAGGGCCGATTCACCAT 340

G  K  G  L  E  W  V  A  V  I  S  Y  D  G  S  T  K  Y  Y  A  D  S  V  K  G  R  F  T  I

CTCCAGAGACACTTCCAAGAACACGGTGTATCTAAAAATGAACAGCCTGAGAACTGAGGACACGGCTGTCTATTACTGTGCGAGA 425

S  R  D  T  S  K  N  T  V  Y  L  K  M  N  S  L  R  T  E  D  T  A  V  Y  Y  C  A  R

GATCAGAGCCTGTTGGGTGACTATGACCACTACTACGGTTTGGACGTCTGGGGCAAAGGGACCACGGTCACGGTCTCTTCAGCTA 510
                                                     |━━━━━ end of VH ━━━━━|━ sta ━

D  Q  S  L  L  G  D  Y  D  H  Y  Y  G  L  D  V  W  G  K  G  T  T  V  T  V  S  S  A

GCACCAAAGGCCCATCGGTCTTCCCCCTGGCACCCTCCTCCAAGAGCACCTCTGGGGGCACAGCGGCCCTGGGCTGCCTGGTCAA 595
━━━━ start of CH ━━━━▶

S  T  K  G  P  S  V  F  P  L  A  P  S  S  K  S  T  S  G  G  T  A  A  L  G  C  L  V  K

GGACTACTTCCCCGAACCGGTGACGGTGTCGTGGAACTCAGGCGCCCTGACCAGCGGCGTGCACACCTTCCCGGCTGTCCTACAG 680

D  Y  F  P  E  P  V  T  V  S  W  N  S  G  A  L  T  S  G  V  H  T  F  P  A  V  L  Q

TCCTCAGGACTCTACTCCCTCAGCAGCGTGGTGACCGTGCCCTCCAGCAGCTTGGGCACCCAGACCTACATCTGCAACGTGAATC 765

S  S  G  L  Y  S  L  S  S  V  V  T  V  P  S  S  S  L  G  T  Q  T  Y  I  C  N  V  N

ACAAGCCCAGCAACACCAAGGTGGACAAGAAAGTTGAGCCCAAATCTTGTACCAGGCACAGGCAGCCCAGAGGCTGGGAGCAGCT 850
                                        |━━━━━ end of CH ━━━━|━━━━━ Furin Linker ━━━━

```
CTACAACACCGTGTCATTTAACCTTGGAGAAGCTTATGAGTACCCCACTTTTATACAAGATTTGCGCAATGAATTGGCTAAGGGC  935
```
|◄──── start of De-Bouganin156 ────►|

```
    Y  N  T  V  S  F  N  L  G  E  A  Y  E  Y  P  T  F  I  Q  D  L  R  N  E  L  A  K  G
ACACCAGTATGTCAACTTCCAGTGACACTACAAACCATAGCCGATGACAAGCGATTTGTTCTAGTTGATATCACTACGACCTCGA 1020

T  P  V  C  Q  L  P  V  T  L  Q  T  I  A  D  D  K  R  F  V  L  V  D  I  T  T  T  S
AGAAAACAGTTAAGGTTGCTATAGATGTGACAGATGTGTATGTTGTGGGTTATCAAGACAAATGGGATGGCAAAGATCGAGCTGT 1105

K  K  T  V  K  V  A  I  D  V  T  D  V  Y  V  V  G  Y  Q  D  K  W  D  G  K  D  R  A  V
TTTCCTTGACAAGGTTCCTACTGTTGCAACTAGTAAACTTTTCCCAGGGGTGACTAATCGTGTAACGTTAACATTTGATGGCAGC 1190

F  L  D  K  V  P  T  V  A  T  S  K  L  F  P  G  V  T  N  R  V  T  L  T  F  D  G  S
TATCAGAAACTTGTGAATGCTGCCAAAGCTGATAGAAAGGCTCTCGAACTGGGGGTTAACAAATTGGAATTTTCCATTGAAGCAA 1275

Y  Q  K  L  V  N  A  A  K  A  D  R  K  A  L  E  L  G  V  N  K  L  E  F  S  I  E  A
TCCATGGTAAAACGATAAATGGTCAAGAGGCAGCCAAGTTCTTTCTTATTGTCATCCAAATGGTTTCAGAGGCAGCTCGGTTCAA 1360

I  H  G  K  T  I  N  G  Q  E  A  A  K  F  F  L  I  V  I  Q  M  V  S  E  A  A  R  F  K
ATATATTGAGACTGAGGTGGTTGATAGAGGATTATATGGATCATTCAAACCTAATTTTAAAGTATTGAACTTGGAGAACAATTGG 1445

Y  I  E  T  E  V  V  D  R  G  L  Y  G  S  F  K  P  N  F  K  V  L  N  L  E  N  N  W
GGCGACATCTCTGATGCCATTCACAAATCATCCCCACAATGTACCACTATTAATCCGGCACTTCAGTTGATAAGCCCCTCAAATG 1530

G  D  I  S  D  A  I  H  K  S  S  P  Q  C  T  T  I  N  P  A  L  Q  L  I  S  P  S  N
ACCCATGGGTTGTAAATAAAGTGAGTCAAATTAGTCCCGATATGGGTATCCTTAAGTTTAAAAGCTCCAAATAGTGATCTAGAGT 1615
```
                                          |◄──── end of De-Bouganin156 ────►|
```
    D  P  W  V  V  N  K  V  S  Q  I  S  P  D  M  G  I  L  K  F  K  S  S  K
CGACCTGCAGGTCTATGGAACGATAAATGCCCATGAAAATTCTATTTCAAGGAGACAGTCATAATGAAATACCTATTGCCTACGG 1700
```
                                                                    |◄──── PelB ────|
                                                                       M  K  Y  L  L  P  T
```
CAGCCGCTGGATTGTTATTACTCGCTGCCCAACCAGCGATGGCGCATCACCATCACCATCACGATATCGTGTTGACGCAGTCTCC 1785
```
|──────── PelB ────────|  | 6xHis |  |◄── start of VL ───►|
 A  A  A  G  L  L  L  L  A  A  Q  P  A  M  A  H  H  H  H  H  H  D  I  V  L  T  Q  S  P

Figure 15 (Cont)

```
AGGCACCCTGTCTTTGTCTCCAGGGGAAAGAGCCACCCTCTCCTGCAGGGCCAGTCAGAGTGTTAGTAGCAGCTACTTAGCCTGG  1870
  G  T  L  S  L  S  P  G  E  R  A  T  L  S  C  R  A  S  Q  S  V  S  S  S  Y  L  A  W

TACCAGCAGAAACCTGGCCAGGCTCCCAGGCTCCTCATCTATGGTGCATCCACCAGGGCCACTGGCATGCCAGACAGGTTCAGTG  1955
  Y  Q  Q  K  P  G  Q  A  P  R  L  L  I  Y  G  A  S  T  R  A  T  G  M  P  D  R  F  S

GCAGTGGGTCCGGGACAGACTTCACTCTCACCATCAGTAGACTGGAGCCTGAAGATTTTGCAGTGTATTACTGTCAGCAGTATGG  2040
  G  S  G  S  G  T  D  F  T  L  T  I  S  R  L  E  P  E  D  F  A  V  Y  Y  C  Q  Q  Y  G

TAGCTCACCTCAGACACCTCAGATCACTTTCGGCGGAGGGACCAAGGTGGAGATCAAACGAACTGTGGCTGCACCATCTGTCTTC  2125
                                            ├──── end of VL ────┤├──── start of CL ────▶
  S  S  P  Q  T  P  Q  I  T  F  G  G  G  T  K  V  E  I  K  R  T  V  A  A  P  S  V  F ATCTTCCCGCCATCTGATGAGCAGTTGAAATCTGGAACTGCCTCTGTTGTGTGCCTGCTGAATAACTTCTATCCCAGAGAGGCCA  2210
  I  F  P  P  S  D  E  Q  L  K  S  G  T  A  S  V  V  C  L  L  N  N  F  Y  P  R  E  A AAGTACAGTGGAAGGTGGATAACGCCCTCCAATCGGGTAACTCCCAGGAGAGTGTCACAGAGCAGGACAGCAAGGACAGCACCTA  2295
  K  V  Q  W  K  V  D  N  A  L  Q  S  G  N  S  Q  E  S  V  T  E  Q  D  S  K  D  S  T  Y CAGCCTCAGCAGCACCCTGACGCTGAGCAAAGCAGACTACGAGAAACACAAAGTCTACGCCTGCGAAGTCACCCATCAGGGCCTG  2380
  S  L  S  S  T  L  T  L  S  K  A  D  Y  E  K  H  K  V  Y  A  C  E  V  T  H  Q  G  L AGCTCGCCCGTCACAAAGAGCTTCAACAGGGGAGAGTGTTAGTGACTCGAG  2431
           ├──── end of CL ────┤
  S  S  P  V  T  K  S  F  N  R  G  E  C  .  .
```

Figure 15(Cont)

|          | IC$_{50}$ |
|----------|-----------|
| VB6-011  | 350nM     |

MODIFIED BOUGANIN PROTEINS, CYTOTOXINS AND METHODS AND USES THEREOF

CROSS REFERENCE TO RELATED APPLICATIONS

This application claims priority under 35 USC 119(e) from U.S. provisional application No. 60/554,580, filed on Mar. 19, 2004 and U.S. provisional application No. 60/630,571, filed on Nov. 26, 2004, which are incorporated by reference herein in their entirety.

FIELD OF THE INVENTION

The invention relates to modified bouganin proteins and cytotoxins containing the modified proteins useful as therapeutics against cancer. Specifically, T-cell epitopes are removed or altered to reduce immunogenicity of the bouganin toxins.

BACKGROUND OF THE INVENTION

There are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response [Schroff, R. W. et al (1985) Cancer Res. 45: 879-885; Shawler, D. L. et al (1985) J. Immunol. 135: 1530-1535]. For monoclonal antibodies, a number of techniques have been developed in attempt to reduce the HAMA response [WO 89/09622; EP 0239400; EP 0438310; WO 91/06667]. These recombinant DNA approaches have generally reduced the mouse genetic information in the final antibody construct whilst increasing the human genetic information in the final construct. Notwithstanding, the resultant "humanised" antibodies have, in several cases, still elicited an immune response in patients [Issacs J. D. (1990) Sem. Immunol. 2: 449, 456; Rebello, P. R. et al (1999) Transplantation 68: 1417-1420].

The key to the induction of an immune response is the presence within the protein of peptides that can stimulate the activity of T-cells via presentation on MHC class II molecules, so-called "T-cell epitopes". Such T-cell epitopes are commonly defined as any amino acid residue sequence with the ability to bind to MHC Class II molecules. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response.

MHC Class II molecules are a group of highly polymorphic proteins which play a central role in helper T-cell selection and activation. The human leukocyte antigen group DR (HLA-DR) are the predominant isotype of this group of proteins; however, isotypes HLA-DQ and HLA-DP perform similar functions. In the human population, individuals bear two to four DR alleles, two DQ and two DP alleles. The structure of a number of DR molecules has been solved and these appear as an open-ended peptide binding groove with a number of hydrophobic pockets which engage hydrophobic residues (pocket residues) of the peptide [Brown et al (1993) Nature 364: 33; Stern et al (1994) Nature 368: 215]. Polymorphism identifying the different allotypes of class II molecule contributes to a wide diversity of different binding surfaces for peptides within the peptide binding groove and at the population level ensures maximal flexibility with regard to the ability to recognize foreign proteins and mount an immune response to pathogenic organisms.

An immune response to a therapeutic protein proceeds via the MHC class II peptide presentation pathway. Here exogenous proteins are engulfed and processed for presentation in association with MHC class II molecules of the DR, DQ or DP type. MHC Class II molecules are expressed by professional antigen presenting cells (APCs), such as macrophages and dendritic cells amongst others. Engagement of a MHC class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T-killer cells as a full cellular immune response.

T-cell epitope identification is the first step to epitope elimination as recognized in WO98/52976; WO00/34317; WO02/069232; WO02/079232; and WO02/079415. In these teachings, predicted T-cell epitopes are removed by the use of judicious amino acid substitution within the protein of interest. Besides computational techniques, there are in vitro methods for measuring the ability of synthetic peptides to bind MHC class II molecules. An exemplary method uses B-cell lines of defined MHC allotype as a source of MHC class II binding surface and may be applied to MHC class II ligand identification [Marshall K. W. et al. (1994) J. Immunol. 152:4946-4956; O'Sullivan et al (1990) J. Immunol. 145: 1799-1808; Robadey C. et al (1997) J. Immunol 159: 3238-3246]. However, such techniques are not adapted for the screening of multiple potential epitopes to a wide diversity of MHC allotypes, nor can they confirm the ability of a binding peptide to function as a T-cell epitope.

Techniques exploiting soluble complexes of recombinant MHC molecules in combination with synthetic peptides have also come into use [Kern, F. et al (1998) Nature Medicine 4:975-978; Kwok, W. W. et al (2001) TRENDS in Immunol. 22:583-588]. These reagents and procedures are used to identify the presence of T-cell clones from peripheral blood samples from human or experimental animal subjects that are able to bind particular MHC-peptide complexes and are not adapted for screening multiple potential epitopes to a wide diversity of MHC allotypes.

Biological assays of T-cell activation offer a practical option to providing a reading of the ability of a test peptide/protein sequence to evoke an immune response. Examples of this kind of approach include the work of Petra et al using T-cell proliferation assays to the bacterial protein staphylokinase, followed by epitope mapping using synthetic peptides to stimulate T-cell lines [Petra, A. M. et al (2002) J. Immunol. 168: 155-161]. Similarly, T-cell proliferation assays using synthetic peptides of the tetanus toxin protein have resulted in definition of immunodominant epitope regions of the toxin [Reece J. C. et al (1993) J. Immunol. 151: 6175-6184]. WO99/53038 discloses an approach whereby T-cell epitopes in a test protein may be determined using isolated sub-sets of human immune cells, promoting their differentiation in vitro and culture of the cells in the presence of synthetic peptides of interest and measurement of any induced proliferation in the cultured T-cells. The same technique is also described by Stickler et al. [Stickler, M. M. et al (2000) J. Immunotherapy 23:654-660], where in both instances the method is applied to the detection of T-cell epitopes within bacterial subtilisin. Such a technique requires careful application of cell isolation techniques and cell culture with multiple cytokine supplements to obtain the desired immune cell sub-sets (dendritic cells, CD4+ and or CD8+ T-cells) and is not conducive to rapid through-put screening using multiple donor samples.

Recently a combination approach using population based T-cell proliferation assays and in silico simulation of peptide MHC binding in the design of epitope depleted proteins has also been advanced [WO 03/104803].

As depicted above and as consequence thereof, it would be desirable to identify and to remove or at least to reduce T-cell epitopes from a principal therapeutically valuable but originally immunogenic peptide, polypeptide or protein.

SUMMARY OF THE INVENTION

The invention is conceived to overcome the practical reality that soluble proteins introduced with therapeutic intent in humans can trigger an immune response resulting in development of host antibodies that bind to the soluble protein. The present invention seeks to address this by providing bouganin proteins with reduced propensity to elicit an immune response. According to the methods described herein, the inventors have identified the regions of the bouganin molecule comprising the critical T-cell epitopes driving the immune responses to this protein.

The present invention relates to a modified bouganin protein wherein the modified bouganin has a reduced propensity to elicit an immune response. In a preferred embodiment, the modified bouganin has a reduced propensity to activate T-cells and the modified bouganin is modified at one or more amino acid residues in a T-cell epitope. The T-cell epitopes are selected preferably from the group consisting of:

a) AKVDRKDLELGVYKL (epitope region R1, SEQ ID NO: 2), b) LGVYKLEFSIEAIHG (epitope region R2, SEQ ID NO: 3); and c) NGQEIAKFFLIVIQM (epitope region R3, SEQ ID NO: 4).

The present invention also relates to a cytotoxin comprising a targeting moiety attached to a modified bouganin protein of the invention. In one embodiment, the targeting moiety is a ligand that binds to a cancer cell. In a further embodiment, the ligand is an antibody or antibody fragment that binds to a cancer cell. In a particular embodiment, the antibody recognizes Ep-CAM or tumor-associated antigen. In a most particular embodiment, the present invention provides a cytotoxin comprising VB6-845 or VB6-011.

In another aspect, the invention provides a method of inhibiting or destroying cancer cells comprising administering a cytotoxin of the invention to the cancer cells.

The present invention also relates to a method of treating cancer by administering a cytotoxin of the invention to an animal in need thereof.

Still further, a process is provided for preparing a pharmaceutical for treating an animal with cancer comprising the steps of identifying T-cell epitopes of bouganin, modifying one or more amino acid residues in a T-cell epitope to prepare a modified bouganin having reduced propensity to activate T-cells; preparing a cytotoxin have a cancer-binding ligand attached to a modified bouganin; and suspending the cytotoxin in a pharmaceutically acceptable carrier, diluent or excipient.

In a further aspect, the invention provides a pharmaceutical composition for treating an animal with cancer comprising the cytotoxin of the invention and a pharmaceutically acceptable carrier, diluent or excipient.

The cytotoxins, compositions and methods of the present invention may be used to treat various forms of cancer such as colorectal cancer, breast cancer, ovarian cancer, pancreatic cancer, head and neck cancer, bladder cancer, gastrointestinal cancer, prostate cancer, small cell and non small cell lung cancer, sarcomas, gliomas, T- and B-cell lymphomas.

The invention also provides the T-cell epitope peptides of the bouganin protein and the modified T-cell epitope peptides of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows results of activity assays of the T-cell epitope depleted modified bouganin proteins Bou156 (panel A) and Bou157 (panel B). Bou156 comprises the substitutions V123A, D127A, Y133N and I152A. Bou157 comprises the substitutions V123A, D127A, Y133Q and I152A. Both assay sets are conducted using wild type protein and a disabled modified bouganin (Y70A) as controls. Activity is expressed as % measured luciferase activity versus concentration of bouganin protein in the assay.

FIG. 2 shows T-cell proliferation assay results for three synthetic peptides and 2 different PBMC donor samples. The peptides designated Del-41, Del-44 and Del-50 were tested at 1 µM final concentration (panel A) and 5 µM final concentration (panel B). These peptides are derived from the immunogenic regions of the bouganin molecule and contain substitutions designed to eliminate their immunogenicity.

FIG. 3 illustrates VB6-845, a modified bouganin cytotoxin having a Fab anti-Ep-CAM, wherein the de-bouganin (Bou156) is linked to the C-terminus of the CH domain via a furin linker. FIG. 3B illustrates the nucleic acid coding sequence (SEQ ID NO:15) and the amino acid sequence (SEQ ID NO:16) of the pro-sequences

FIG. 5 illustrates the control Fab anti-Ep-CAM construct without the plant toxin, de-bouganin (VB5-845). FIG. 5B illustrates the nucleic acid coding sequence (SEQ ID NO:17) and the amino acid sequence (SEQ ID NO:18) of the pro-sequences

FIG. 6 illustrates the Fab anti-Ep-CAM de-bouganin construct VB6-845-$C_L$-de-bouganin, wherein the Bou156 is linked at the C-terminus of the $C_L$ domain. FIG. 6B illustrates the nucleic acid coding sequence (SEQ ID NO:19) and the amino acid sequence (SEQ ID NO:20) of the pro-sequences

FIG. 7 illustrates the Fab anti Ep-CAM, de-bouganin construct, VB6-845-NV$_H$-de-bouganin, wherein Bou156 is linked to the N-terminus of the V$_H$ domain. FIG. 7A illustrates the dicistronic units encoding the pro-sequences, FIG. 7B illustrates the nucleic acid coding sequence (SEQ ID NO:21) and the amino acid sequence (SEQ ID NO:22) of the pro-sequences and FIG. 7C illustrates the assembled VB6-845-NV$_H$-de-bouganin protein without the pelB sequences.

FIG. 8 illustrates the Fab anti-Ep-CAM de-bouganin construct, VB6-845-NV$_L$-de-bouganin, wherein Bou156 is linked to the N-terminus of the V$_L$ domain. FIG. 8A illustrates the dicistronic units encoding the pro-sequences, FIG. 8B illustrates the nucleic acid coding sequence (SEQ ID NO:23) and the amino acid sequence (SEQ ID NO:24) of the pro-sequences and FIG. 8C illustrates the assembled VB6-845-NV$_L$-de-bouganin protein without the pelB sequences.

FIG. 10 illustrates the results of the flow cytometry reactivity studies. FIG. 10A illustrates the reactivity of VB6-845 (construct of FIG. 3) and VB6-845-C$_L$-de-bouganin (construct of FIG. 6) in Ep-CAM-positive cell lines CAL 27 and OVCAR-3 and Ep-CAM-negative cell line A-375, while

FIG. 15 illustrates the nucleic acid coding sequence (SEQ ID NO: 27) and the amino acid sequence (SEQ ID NO:28) of the pro-sequences of VB6-011.

DETAILED DESCRIPTION OF THE INVENTION

Figure 3A:
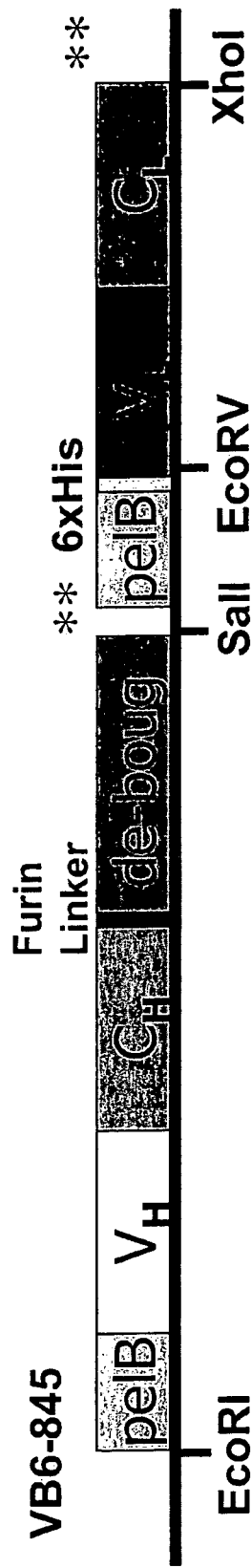
FIG. 3A illustrates the dicistronic unit encoding the pro-sequences.

The inventors have identified T-cell epitopes in bouganin, and have designed and made modified bouganin proteins that have reduced propensity to activate human T cells compared to the non-modified bouganin protein.

(A) Modified Boucianin Proteins

The present invention relates to a modified bouganin protein wherein bouganin has been modified in order to have a reduced propensity to elicit an immune response, preferably a T-cell response, as compared to a non-modified bouganin protein. Mature bouganin protein is a single polypeptide of 250 amino acids with a molecular weight of approximately 26,200 Da [Den Hartog et al (2002) *Eur. J. Biochem.* 269: 1772-1779; U.S. Pat. No. 6,680,296]. Bouganin is a type 1 ribosome inactivating protein (RIP) originally isolated from the plant *Bougainvillea spectabilis Willd* [Bolognesi et al (1997) *Planta* 203: 422-429]. The RIPs from plants are RNA N-glycosidases that depurinate the major ribosomal RNA of cells, thereby damaging the ribosomes and leading to a cessation of protein synthesis and cell death.

The amino acid sequence of the mature bouganin protein (depicted in single-letter code) is:

```
                                        [SEQ ID NO. 1]
YNTVSFNLGEAYEYPTFIQDLRNELAKGTPVCQLPVTLQTIADDKRFVL

VDITTTSKKTVKVAIDVTDVYVVGYQDKWDGKDRAVFLDKVPTVATSKL

FPGVTNRVTLTFDGSYQKLVNAAKVDRKDLELGVYKLEFSIEAIHGKTI

NGQEIAKFFLIVIQMVSEAARFKYIETEVVDRGLYGSFKPNFKVLNLEN

NWGDISDAIHKSSPQCTTINPALQLISPSNDPWVVNKVSQISPDMGILK

FKSSK.
```

The term "non-modified bouganin protein" means a bouganin protein that has not been modified in order to reduce its propensity to elicit an immune response. The sequence of wild-type or a non-modified bouganin is shown in SEQ ID NO:1. However, one of skill in the art will appreciate that the term "non-modified bouganin" also includes modifications to SEQ ID NO:1 as long as such modifications do not reduce the propensity to elicit an immune response. Examples of modifications that can be made to SEQ ID NO:1 include peptide fragments and conservative amino acid substitutions that do not reduce the immunogenicity of the protein.

The term "modified bouganin protein" means a bouganin protein that has been modified as compared to the non-modified bouganin protein (described above) wherein said modification reduces the propensity of the bouganin to elicit an immune response. Modified bouganin protein can also be referred to as deimmunized bouganin. The "modified bouganin protein" can be a modified full length sequence or a modified fragment of the non-modified bouganin protein. The "modified bouganin protein" may also contain other changes as compared to the wild-type bouganin sequence which do not alter immunogenicity of the peptide. The modified bouganin protein will preferably have the same biological activity as the non-modified bouganin.

The term "reduced propensity to elicit an immune response" as used herein means that the modified bouganin protein is less immunogenic than non-modified bouganin.

The term "immune response" includes both cellular and humoral immune responses. In a preferred embodiment, the modified bouganin has a reduced propensity to activate T-cells.

The term "reduced propensity to activate human T-cells" as used herein means the modified bouganin protein has a reduced propensity to activate human T-cells as compared to the non-modified bouganin protein. One of skill in the art can test whether or not a modified bouganin has a reduced propensity to activate T-cells using assays known in the art including assessing the stimulation index of the protein.

The term "stimulation index" as used herein refers to the measure of the ability of the modified or non-modified bouganin protein to activate human T cells. For example, the modified or non-modified bouganin protein, or peptides thereof, can be tested for their ability to evoke a proliferative response in human T-cells cultured in vitro. Where this type of approach is conducted using naïve human T-cells taken from healthy donors, the inventors have established that in the operation of such an assay, a stimulation index equal to or greater than 2.0 is a useful measure of induced proliferation. The stimulation index is conventionally derived by division of the proliferation score (e.g. counts per minute of radioactivity if using $^3$H-thymidine incorporation) measured to the test peptide by the score measured in cells not contacted with a test peptide.

In one embodiment, the invention provides a modified bouganin protein, wherein the modified bouganin protein has biological activity and has reduced propensity to activate human T cells compared to a non-modified bouganin protein.

In another embodiment, the invention provides a modified bouganin protein, wherein the modified bouganin protein has reduced propensity to activate human T cells compared to a non-modified bouganin protein and has biological activity that is lower than the non-modified bouganin protein. In yet another embodiment, the invention provides a modified bouganin protein wherein the modified bouganin protein has reduced propensity to activate human T cells and no biological activity. Such modified proteins could, for instance, be used as controls, in assays or to tolerize subjects.

The term "biological activity" as used herein is the ability of the modified or non-modified bouganin protein to inhibit protein synthesis on ribosomes, which can be assessed in a number of ways. It should be noted that a modified bouganin protein will still have biological activity even if such activity is lower than that of the non-modified protein, however it would need to have some level of detectable activity. For example, the biological activity of the modified or non-modified bouganin protein can be assessed by identifying their N-glycosidase activity, and in particular with sufficient activity to provide significant inhibition of protein translation. One such suitable assay involves testing the activity of the variant bouganin proteins in comparison to non-modified bouganin in a cell-free protein synthesis assay. A coupled transcription/translation mix containing methionine, DNA encoding the reporter protein luciferase and serial dilutions of non-modified and modified bouganin protein are co-incubated. The levels of translated luciferase are readily detected using a luminescence counter following addition of a substrate reagent. The measured luminescence is inversely proportional to the bouganin N-glycosidase activity present in the reaction. It is usual to provide a negative control such as an in-active bouganin protein, for example containing a Y70A substitution.

In a preferred embodiment, the modified bouganin peptide is modified at one or more T-cell epitopes in the bouganin protein sequence.

The term "T-cell epitope" means an amino acid sequence which is able to bind major histocompatibility complex (MHC) class II, able to stimulate T-cells and/or also able to bind (without necessarily measurably activating) T-cells in complex with MHC class II.

In one aspect, a general method that can be used in the present invention leading to the modified bouganin proteins comprising modified T-cell epitopes comprises the following steps:

(i) determining the amino acid sequence of the protein or part thereof;

(ii) identifying one or more potential T-cell epitopes within the amino acid sequence of the protein by methods such as determination of the binding of the peptides to MHC molecules using in vitro or in silico techniques or biological assays;

(iii) designing new sequence variants with one or more amino acids within the identified potential T-cell epitopes modified in such a way to substantially reduce or eliminate the activity of the T-cell epitope as determined by the binding of the peptides to MHC molecules using in vitro or in silico techniques or biological assays. Such sequence variants are created in such a way to avoid creation of new potential T-cell epitopes by the sequence variations unless such new potential T-cell epitopes are, in turn, modified in such a way to substantially reduce or eliminate the activity of the T-cell epitope;

(iv) constructing such sequence variants by recombinant DNA techniques and testing said variants in order to identify one or more variants with desirable properties according to well known recombinant techniques; and (v) optionally repeating steps (ii) to (iv).

In an example, step (iii) is carried out by substitution, addition or deletion of amino acid residues in any of the T-cell epitopes in the non-modified bouganin protein. In another example, the method to make the modified bouganin protein is made with reference to the homologous protein sequence and/or in silico modeling.

The identification of potential T-cell epitopes according to step (ii) can be carried out according to methods described previously in the art. Suitable methods are disclosed in WO 98/59244; WO 98/52976; WO 00/34317; WO 02/069232 and may be used to identify binding propensity of bouganin derived peptides to an MHC class II molecule. In order to identify biologically relevant peptides, the inventors have developed an approach exploiting ex vivo human T-cell proliferation assays. This approach has proven to be a particularly effective method and has involved the testing of overlapping bouganin derived peptide sequences in a scheme so as to scan and test the entire bouganin sequence. The synthetic peptides are tested for their ability to evoke a proliferative response in human T-cells cultured in vitro. Where this type of approach is conducted using naïve human T-cells taken from healthy donors, the inventors have established that in the operation of such an assay, a stimulation index equal to or greater than 2.0 is a useful measure of induced proliferation. The stimulation index is conventionally derived by division of the proliferation score (e.g. counts per minute of radioactivity if using $^3$H-thymidine incorporation) measured to the test peptide by the score measured in cells not contacted with a test peptide.

Accordingly, in the present studies, 89 synthetic 15-mer peptides (as listed in Table 1) were used in T-cell proliferation assays with PBMCs (peripheral blood mononuclear cells) from naïve donors (i.e. no known sensitization to bouganin). 20 donor PBMC samples were selected to achieve an optimal coverage of MHC class II allotypes. PBMCs were stimulated with individual peptides in triplicate cultures for 7 days before proliferation was assessed by $^3$H-thymidine incorporation. All peptides were diluted at two different concentrations: 1 μM and 5 μM. The stimulation indices (SI) were calculated as the amount of $^3$H incorporated into the cells, divided by the amount of $^3$H incorporated in mock-stimulated controls.

This method has identified the most immunogenic regions of the bouganin molecule in humans. Accordingly, in a specific embodiment, the modified bouganin protein is modified at one or more amino acid residues in a T-cell epitope selected from the group consisting of:
a) AKVDRKDLELGVYKL, termed herein epitope region R1 (SEQ ID NO:2);
b) LGVYKLEFSIEAIHG, termed herein epitope region R2 (SEQ ID NO:3); and
c) NGQEIAKFFLIVIQM, termed herein epitope region R3 (SEQ ID NO:4).

These T-cell epitopes have been identified on the basis of giving SI>2 in two or more donor PBMC samples. The above disclosed peptide sequences represent the critical information required for the construction of modified bouganin proteins in which one or more of these epitopes is compromised.

In an embodiment of the invention, the modified bouganin protein of the invention has at least one T-cell epitope removed. In another embodiment, the modified bouganin protein of the invention has one, two or three T-cell epitopes removed. The invention also contemplates a modified bouganin protein wherein 1 to 9 amino acid residues are modified, preferably in the T-cell epitope. In another embodiment, 1 to 5 amino acid residues are modified. The term "modified" as used herein means the amino acid residues are modified by substitution, addition or deletion, preferably by substitution, but the bouganin protein has reduced propensity to activate human T cells. In another embodiment the modified protein has biological activity. More preferably the modified bouganin protein of the invention is modified by substitution at a position corresponding to any of the amino acids specified within sequences (a), (b) or (c) above.

One embodiment of the present invention comprises bouganin proteins for which the MHC class II ligands identified within any of the epitopes R1-R3 are modified such as to eliminate binding or otherwise reduce the numbers of MHC allotypes to which the peptide can bind. Amino acids in the R1 to R3 regions to eliminate binding or otherwise reduce the numbers of MHC allotypes to which the peptide can bind can be modified by substitution, addition or deletion.

For the elimination of T-cell epitopes, amino acid substitutions are made at appropriate points within the peptide sequence predicted to achieve substantial reduction or elimination of the activity of the T-cell epitope. In practice an appropriate point will in one embodiment equate to an amino acid residue binding within one of the pockets provided within the MHC class II binding groove.

In one embodiment, the binding within the first pocket of the cleft at the so-called P1 or P1 anchor position of the peptide is modified. The quality of binding interaction between the P1 anchor residue of the peptide and the first pocket of the MHC class II binding groove is recognized as being a major determinant of overall binding affinity for the whole peptide. An appropriate substitution at this position of the peptide will be for a residue less readily accommodated within the pocket, for example, substitution to a more hydrophilic residue. Amino acid residues in the peptide at positions equating to binding within other pocket regions within the MHC binding cleft are also considered and fall under the scope of the present.

It is understood that single amino acid substitutions, deletions or additions within a given potential T-cell epitope are a preferred route by which the epitope may be eliminated. Combinations of modifications (i.e. substitutions, deletions and additions) within a single epitope may be contemplated and for example can be particularly appropriate where individually defined epitopes are in overlap with each other as is the present case where epitope regions R1 and R2 overlap by 5 residues. Moreover, either single amino acid modifications within a given epitope or in combination within a single epitope may be made at positions not equating to the "pocket residues" with respect to the MHC class II binding groove, but at any point within the peptide sequence. Modifications may be made with reference to an homologue structure or structural method produced using in silico techniques known in the art and may be based on known structural features of the molecule according to this invention. All such modifications fall within the scope of the present invention.

The epitope regions R1-R3 of bouganin were analyzed for indication of MHC class II ligands encompassed within their respective sequences. A software tool exploiting the schemes outlined in WO 98/59244 and WO 02/069232 was used for this analysis. The software simulates the process of antigen presentation at the level of the peptide MHC class II binding interaction to provide a binding score for any given peptide sequence. Such a score is determined for many of the predominant MHC class II allotypes existent in the population. As this scheme is able to test any peptide sequence, the consequences of amino acid substitutions, additions or deletions with respect to the ability of a peptide to interact with a MHC class II binding groove can be predicted. Consequently new sequence compositions can be designed which contain reduced numbers of peptides able to interact with the MHC class II and thereby function as immunogenic T-cell epitopes.

Under this scheme in one embodiment of the invention substitutions within epitope region R1 comprise changes at positions V123, D127 and/or E129. Similarly for epitope region R2, in one embodiment the substitution is at position Y133. This residue falls into the region of overlap between R1 and R2 but substitution at Y133 is sufficient to eliminate the R2 related MHC class II ligand and is not sufficient of itself to eliminate R1 related MHC class II ligands. For epitope region R3, in one embodiment of the invention substitutions are to residues E151, and/or I152.

In all instances the substitutions are to one or more alternative amino acid residues. Analysis of R1 with the MHC II stimulation software indicated that amino acid residues 123, 127, 129 and 131 were key residues in this epitope for binding to MHC II molecules. Residue 123 is a preferred site for mutation of the R1 region because it is at the surface of the molecule, away from the active site and is variable in RIP sequence alignment. Nevertheless, not all substitution yield an active molecule hence the need to validate mutations in the bioactivity assay. Thus for example within R1, substitutions V123T, V123A and V123Q are examples of preferred alternative substitutions. Residue 131 was found to be absolutely conserved in RIP and hence is unlikely suitable for mutation. Residue 127 and 129 are not highly conserved but only a restricted number of residues were found to have an impact on MHC II binding. The substitution sets: D127G, D127A, E129Q and E129G are also preferred substitutions. For R2, residue 133 was shown to be a likely candidate to abolish MHC II binding and its apparent surface localization (as determined by modeling) combined to the fact that it is not highly conserved across RIP make it a good candidate for mutation. Preferred alternative substitutions were found to be Y133N, Y133T, Y133A, Y133R, Y133D, Y133E, Y133Q, Y133G, Y133K, Y133H and Y133S. For R3, amino acid residues 152, 155 and 158 were identified as key residues for MHC II binding. However, residues 155 and 158 are part of a highly conserved hydrophobic stretch thus suggesting that their mutation would not yield bioactive molecules. Residue poorly conserved was found to be a more likely candidate. For R3, the substitution sets: 1152Q and 1152A are also preferred substitutions.

Accordingly, the invention provides a modified bouganin protein wherein the bouganin is modified at one or more of $X^1$, $X^2$, $X^3$, $X^4$ or $X^5$ as follows:

a) AKX$^1$DRKX$^2$LX$^3$LGVX$^4$KL (epitope region R1, SEQ ID NO:5);
b) LGVX$^4$KLEFSIEAIHG (epitope region R2, SEQ ID NO:6); and
c) NGQEX$^5$AKFFLIVIQM (epitope region R3, SEQ ID NO:7)

wherein $X^1$ through $X^5$ can be any amino acid.

In a specific embodiment, $X^1$ is T or A or Q; $X^2$ is G or A; $X^3$ is Q or G; $X^4$ is N or D or T or A or R or Q or E or G or H or K or S; and $X^5$ is Q or A (epitope region R1, SEQ ID NO:8; epitope region R2, SEQ ID NO:9; epitope region R3, SEQ ID NO:10).

Taken together a most preferred substitution set may be compiled based on immunogenic epitope mapping studies using ex vivo T-cell assays, in silico MHC peptide binding simulations and structural considerations from sequence homology analysis. Finally, if a bioactive protein is preferred, in vitro activity assay can then be performed on the modified protein that may comprise one or multiple mutations.

Accordingly, in another embodiment, the invention provides a modified bouganin peptide, comprising the amino acid sequence:

YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKX$^1$DRKX$^2$LX$^3$LGVX$^4$KLEFSIEAIHGKT

INGQEX$^5$AKFFLIVIQMVSEAARFKYIETEVVDRGLYGSFKPNFKVLNLE

NNWGDISDAIHKSSPQCTTINPALQLISPSNDPWVVNKVSQISPDMGILK

FKSSK wherein $X^1$ through $X^5$ can be any amino acid (SEQ ID NO:11).

In a preferred embodiment, $X^1$ is T or A or Q; $X^2$ is G or A; $X^3$ is Q or G; $X^4$ is N or D or T or A or R or Q or E or G or H or K or S; and $X^5$ is Q or A (SEQ ID NO: 12).

In a specific embodiment, the modified bouganin protein comprises the amino acid sequence:

(SEQ ID NO:13)
YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKADRKALELGVNKLEFSIEAIHGKTINGQ

EAAKFFLIVIQMVSEAARFKYIETEVVDRGLYGSFKPNFKVLNLENNWGD

ISDAIHKSSPQCTTINPALQLISPSNDPWVVNKVSQISPDMGILKF

KSSK.

In yet another embodiment, the modified bouganin protein comprises the amino acid sequence:

(SEQ ID NO:14)
YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKADRKALELGVQKLEFSIEAIHGKTINGQ

EAAKFFLIVIQMVSEAARFKYIETEVVDRGLYGSFKPNFKVLNLENNWGD

ISDAIHKSSPQCTTINPALQLISPSNDPWVVNKVSQISPDMGILKF

KSSK.

Underlined residues are substituted residues different from the non-modified bouganin protein.

As will be clear to the person skilled in the art, multiple alternative sets of modifications could be arrived at which achieve the objective of removing undesired epitopes. The resulting sequences would however remain broadly homologous with the specific proteins disclosed herein and therefore fall under the scope of the present invention. Obvious chemical equivalents to the sequences disclosed by the present invention are also contemplated to fall within the scope of the present invention. Such equivalents include proteins that perform substantially the same function in substantially the same way.

In another embodiment the modified bouganin protein of the invention has 1, 2, 3, 4, 5 or more amino acid modifications in the T-cell epitopes of the protein.

In an additional embodiment, the modified bouganin protein of the invention when tested in a T-cell assay evokes a reduced stimulation index in comparison to the non-modified bouganin protein.

In a further embodiment of the invention, the T-cell epitopes of the bouganin protein are mapped using a T-cell assay and then modified such that upon re-testing in the T-cell assay the modified bouganin protein evokes a stimulation index less than the non-modified bouganin protein, preferably the stimulation index is less than 2.0.

It will be clear to a person skilled in the art that if the modified bouganin protein has substantially reduced or no biological activity, it may need further modification by substitution, addition or deletion of amino acid residues to restore the biological activity of the modified bouganin protein. However, such modified bouganin proteins that have substantially reduced or no biological activity are still encompassed within the scope of the invention and have utility as controls in assays, or for tolerization.

In one embodiment, the modified bouganin is mutated at the tyrosine residue at position 70 to yield an inactive bouganin. In a specific embodiment, the tyrosine at position 70 is replaced with alanine. In a preferred embodiment, the modified bouganin has the sequence:

[SEQ ID NO. 129]
YNTVSFNLGEAYEYPTFIQDLRNELAKGTPVCQLPVTLQTIADDKRFVLV

DITTTSKKTVKVAIDVTDVAVVGYQDKWDGKDRAVFLDKVPTVATSKLFP

GVTNRVTLTFDGSYQKLVNAAKVDRKDLELGVYKLEFSIEAIHGKTINGQ

EIAKFFLIVIQMVSEAARFKYIETEVVDRGLYGSFKPNFKVLNLENNWGD

ISDAIHKSSPQCTTINPALQLISPSNDPWVVNKVSQISPDMGILKF

KSSK.

Under the scheme of the present invention, the epitopes are compromised by mutation to result in sequences no longer able to function as T-cell epitopes. It is possible to use recombinant DNA methods to achieve directed mutagenesis of the target sequences and many such techniques are available and well known in the art. In practice a number of modified bouganin proteins will be produced and tested for the desired immune and functional characteristic. It is particularly important when conducting modifications to the protein sequence that the contemplated changes do not introduce new immunogenic epitopes. This event is avoided in practice by retesting the contemplated sequence for the presence of epitopes and/or of MHC class II ligands by any suitable means.

The modified bouganin proteins of the invention may also contain or be used to obtain or design "peptide mimetics". "Peptide mimetics" are structures which serve as substitutes for peptides in interactions between molecules (See Morgan et al (1989), *Ann. Reports Med. Chem.* 24:243-252 for a review). Peptide mimetics include synthetic structures which may or may not contain amino acids and/or peptide bonds but retain the structural and functional features protein of the invention, including biological activity and a reduced propensity to activate human T cells. Peptide mimetics also include peptoids, oligopeptoids (Simon et al (1972) *Proc. Natl. Acad, Sci USA* 89:9367).

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins of the invention. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The molecules of this invention can be prepared in any of several ways but is most preferably conducted exploiting routine recombinant methods. It is a relatively straightforward procedure to use the protein sequences and information provided herein to deduce a polynucleotide (DNA) encoding any of the preferred protein sequences. This can be achieved for example using computer software tools such as the DNSstar software suite [DNAstar Inc, Madison, Wis., USA] or similar. Any such DNA sequence with the capability of encoding the preferred polypeptides of the present or significant homologues thereof, should be considered as embodiments of this invention.

As a general scheme, genes encoding any of the preferred modified bouganin protein sequences can be made using gene synthesis and cloned into a suitable expression vector. In turn the expression vector is introduced into a host cell and cells selected and cultured. The proteins of the invention are purified from the culture medium and formulated into a preparation for therapeutic administration. Alternatively, a wild-type bouganin gene sequence can be obtained for example following a cDNA cloning strategy using RNA prepared from the root tissues of the *Bougainvillea spectabilis Willd* plant. The wild-type gene can be used as a template for mutagenesis and construction preferred variant sequences. In this regard it is particularly convenient to use the strategy of "overlap extension PCR" as described by Higuchi et al [Higuchi et al (1988) *Nucleic Acids Res.* 16: 7351] although other methodologies and systems could be readily applied.

The biological activity of the proteins of the invention can equally be assessed in many ways. In one embodiment, modified bouganin molecules are identified with N-glycosidase activity, and in particular with sufficient activity to provide significant inhibition of protein translation. One such suitable assay involves testing the activity of the modified bouganin proteins in comparison to non-modified bouganin in a cell-free protein synthesis assay. A coupled transcription/translation mix containing methionine, DNA encoding the reporter protein luciferase and serial dilutions of non-modified and modified bouganin proteins are co-incubated. The levels of translated luciferase are readily detected using a luminescence counter following addition of a substrate reagent. The measured luminescence is inversely proportional to the bouganin N-glycosidase activity present in the reaction. It is usual to provide a negative control such as an in-active bouganin protein for example containing a Y70A substitution.

Constitution of the preferred and active bouganin molecules may be achieved by recombinant DNA techniques and this includes bouganin molecules fused with desired antibody or other targeting moieties. Methods for purifying and manipulating recombinant proteins including fusion proteins are well known in the art. Necessary techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

The proteins and peptides of the invention can be prepared using recombinant DNA methods. The proteins of the invention may also be prepared by chemical synthesis using techniques well known in the chemistry of proteins such as solid phase synthesis (Merrifield, 1964, *J. Am. Chem. Assoc.* 85:2149-2154) or synthesis in homogenous solution (Houbenweyl, 1987, Methods of Organic Chemistry, ed. E. Wansch, Vol. 15 I and II, Thieme, Stuttgart).

The present invention also provides a purified and isolated nucleic acid molecule comprising a sequence encoding the modified bouganin proteins or peptides of the invention, preferably a sequence encoding the protein described herein as SEQ ID NO:13 or SEQ ID NO:14.

The term "isolated and purified" as used herein refers to a nucleic acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e. sequences located at the 5' and 3' ends of the nucleic acid) from which the nucleic acid is derived.

The term "nucleic acid" as used herein refers to a sequence of nucleotide or nucleoside monomers consisting of naturally occurring bases, sugars and intersugar (backbone) linkages. The term also includes modified or substituted sequences comprising non-naturally occurring monomers or portions thereof, which function similarly. The nucleic acid sequences of the present invention may be ribonucleic (RNA) or deoxyribonucleic acids (DNA) and may contain naturally occurring bases including adenine, guanine, cytosine, thymidine and uracil. The sequences may also contain modified bases such as xanthine, hypoxanthine, 2-aminoadenine, 6-methyl, 2-propyl, and other alkyl adenines, 5-halo uracil, 5-halo cytosine, 6-aza uracil, 6-aza cytosine and 6-aza thymine, pseudo uracil, 4-thiouracil, 8-halo adenine, 8-amino adenine, 8-thiol adenine, 8-thioalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

In one embodiment, the purified and isolated nucleic acid molecule comprises a sequence encoding the proteins or peptides, preferably SEQ ID NO: 13 or SEQ ID NO: 14, of the invention, comprising
  (a) the nucleic acid sequence, wherein T can also be U;
  (b) nucleic acid sequences complementary to (a);
  (c) nucleic acid sequences which are homologous to (a) or (b);
  (d) a fragment of (a) to (c) that is at least 15 bases, preferably 20 to 30 bases, and which will hybridize to (a) to (c) under stringent hybridization conditions; or
  (e) a nucleic acid molecule differing from any of the nucleic acids of (a) to (c) in codon sequences due to the degeneracy of the genetic code.

Further, it will be appreciated that the invention includes nucleic acid molecules comprising nucleic acid sequences having substantial sequence homology with the nucleic acid sequences encoding the proteins and peptides of the invention, and fragments thereof. The term "sequences having substantial sequence homology" means those nucleic acid sequences which have slight or inconsequential sequence variations from these sequences, i.e., the sequences function in substantially the same manner to produce functionally equivalent proteins. The variations may be attributable to local mutations or structural modifications.

Nucleic acid sequences having substantial homology include nucleic acid sequences having at least 80%, preferably 90% identity with the nucleic acid sequence encoding the proteins and peptides of the invention.

Another aspect of the invention provides a nucleic acid molecule, and fragments thereof having at least 15 bases, which hybridize to nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Accordingly, nucleic acid molecules of the present invention having a sequence which encodes a protein or peptide of the invention may be incorporated according to procedures known in the art into an appropriate expression vector which ensures good expression of the protein or peptide. Possible expression vectors include but are not limited to cosmids, plasmids, or modified viruses (e.g., replication defective retroviruses, adenoviruses and adeno associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

In some embodiments the expression vector comprises a nucleic acid sequence encoding a modified bouganin with a reduced number of potential T cell epitopes, operably linked to an expression control sequence. In various embodiments the expression vector comprises a nucleic acid sequence encoding the proteins or peptides of the invention, or a degenerate variant thereof and will comprise at least the RIP encoding domain of the said nucleic acids operably linked with suitable expression control and selection sequences. Degeneracy in relation to polynucleotides refers to the fact well recognized that in the genetic code many amino acids are specified by more than one codon. The degeneracy of the code accounts for 20 different amino acids encoded by 64 possible triplet sequences of the four different bases comprising DNA.

The term "RIP encoding domain" or "Ribosome Inactivating Protein encoding domain" as used here in means the functional domain which gives bouganin its biological activity.

The nucleic acid molecules of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The invention also provides nucleic acids encoding fusion proteins comprising a novel protein of the invention and a selected protein, or a selectable marker protein Another aspect of the present invention is a cultured cell comprising at least one of the above-mentioned vectors.

A further aspect of the present invention is a method for preparing the modified bouganin comprising culturing the above mentioned cell under conditions permitting expression of the modified bouganin from the expression vector and purifying the bouganin from the cell.

(B) Modified Bouganin Cytotoxins:

As mentioned previously, bouganin is a type 1 ribosome inactivating protein (RIP) that depurinates the major ribosomal RNA of cells leading to cessation of protein synthesis and cell death. As such, the modified bouganins of the invention can be used to prepare cytotoxins. Cytotoxins containing a modified bouganin protein are preferred over cytotoxins containing a non-modified bouganin protein as the former is less immunogenic and will be less likely to be destroyed by the immune system before it reaches its target.

Accordingly, the present invention also provides a cytotoxin comprising (a) a targeting moiety attached to (b) a modified bouganin protein of the invention.

The term "modified bouganin protein of the invention" is used for ease of referral and includes any and all of the modified bouganin proteins described herein such as the modified bouganin proteins described above in Section (A) as well as in the figures and examples.

The term "targeting moiety" as used herein refers to a substance, means, or technique of delivering the modified bouganin protein to a target cell. In one embodiment the targeting moiety is an antibody. In one embodiment the targeting moiety could be a liposome. In one embodiment the liposome can be linked to an antibody. In another embodiment the targeting moiety is a protein able to direct a specific binding interaction to a particular target cell. Such protein moieties include a variety of polypeptide ligands for which there are specific cell surface receptors and include therefore numerous cytokines, peptide and polypeptide hormones and other biological response modifiers. Prominent examples include such proteins as vascular epithelial growth factor, epidermal growth factor, heregulin, the interleukins, interferons, tumour necrosis factor and other protein and glycoprotein molecules. Fusion proteins of these and other molecules with bouganin of the present invention may be contemplated and may comprise the modified bouganin moiety in either the N-terminal or C-terminal orientation with respect to the protein ligand domain. The targeting moiety may be jointed directly to the proteins of the invention or through a linker. In one embodiment, the linker is a peptide linker or a chemical linker. Equally, chemical cross-linking of the purified ligand to the modified bouganin protein may be contemplated and within the scope of the present invention.

In a preferred embodiment, the present invention provides a cytotoxin comprising (a) a ligand that binds to a cancer cell attached to; (b) a modified bouganin protein of the invention.

The ligand can be any molecule that can bind to a cancer cell including, but not limited to, proteins. In one embodiment, the ligand is an antibody or antibody fragment that recognizes the surface of a cancer cell.

Accordingly, the cytotoxins of the present invention may be used to treat various forms of cancer such as colorectal cancer, breast cancer, ovarian cancer, pancreatic cancer, head and neck cancer, bladder cancer, gastrointestinal cancer, prostate cancer, small cell and non small cell lung cancer, sarcomas, gliomas, T- and B-cell lymphomas.

In one embodiment, the cancer cell binding ligand comprises a complete immunoglobulin molecule that binds to the cancer cell. When a cancer cell binding ligand is an antibody or fragment thereof, cytotoxin can be referred to as immunotoxin. In another embodiment, the cancer cell-binding ligand is a dimer of Fab, Fab', scFv, single-domain antibody fragments, or disulfide stabilized Fv fragments. In another embodiment, the cancer antibody comprises a variable heavy chain, variable light chain, Fab, Fab', scFv, single-domain antibody fragment, or disulfide-stabilized Fv fragment. Portions of the cancer cell-binding ligand may be derived from one or more species, preferably comprising portions derived from the human species, and most preferably are completely human or humanized. Regions designed to facilitate purification or for conjugation to toxin may also be included in or added to the cancer cell-binding portion.

In a particular embodiment, the cancer cell binding ligand recognizes Ep-CAM. Ep-CAM (for Epithelial Cell Adhesion Molecule, which is also known as 17-1A, KSA, EGP-2 and GA733-2) is a transmembrane protein that is highly expressed in many solid tumors, including carcinomas of the lung, breast, ovary, colorectum, and squamous cell carcinoma of the head and neck, but weakly expressed in most normal epithelial tissues.

Accordingly, in one embodiment, the invention provides an Ep-CAM-targeted-modified bouganin cytotoxin comprising (a) a ligand (such as an antibody or antibody fragment) that binds to Ep-CAM on the cancer cell attached to; (b) a modified bouganin protein having a reduced propensity to activate T-cells as compared to a non-modified bouganin protein.

In a specific embodiment, the cytotoxin comprises (a) a humanized antibody or antibody fragment that binds to the extracellular domain of human Ep-CAM and comprises complementarity determining region (CDR) sequences derived from a MOC-31 antibody attached to: (b) a modified bouganin protein having a reduced propensity to activate T-cells as compared to a non-modified bouganin protein.

Suitable Ep-CAM-targeted-modified bouganins according to the invention include, without limitation, VB6-845 and variants thereof, other cytotoxins that comprises other single or double chain immunoglobulins that selectively bind Ep-CAM, or variants thereof. The term "VB6-845" as used herein means a cytotoxin that comprises a Fab version of an anti-Ep-CAM scFv antibody linked to a modified form of bouganin, Bou 156 (SEQ ID NO:13). The amino acid sequence and nucleotide sequence of VB6-845 is shown in FIG. 3B (SEQ ID NO:16 and SEQ ID NO:15, respectively).

In another embodiment, the cancer cell binding ligand recognizes a tumor-associated antigen that is found specifically on neoplastic cells and not on normal cells. In a preferred embodiment, the ligand is an antibody that binds tumor-associated antigen. The anti-tumor-associated-antigen antibody specifically recognizes cancer cells from a wide variety of cancers but does not recognize normal, non-cancerous cells.

Accordingly in another embodiment, the invention provides a cytotoxin comprising (a) ligand (such as an antibody or antibody fragment) that binds to tumor-associated antigen on the cancer cell attached to; (b) a modified bouganin protein having a reduced propensity to activate T-cells as compared to a non-modified bouganin protein.

Suitable tumor-associated-antigen-targeted-modified bouganins according to the invention include, without limitation, VB6-011 and variants thereof, other cytotoxins that comprises other single or double chain immunoglobulins that selectively bind tumor-associated-antigen, or variants thereof. The term "VB6-011" as used herein means a cytotoxin that comprises a Fab version of the H11 human monoclonal antibody genetically linked to a modified form of bouganin, BOU 156 (SEQ ID No. 13). The H11 antibody was obtained by the fusion of peripheral blood lymphocytes of a 64 year old male cancer patient fused with a human myeloma cell line to produce hybridomas. The hybridoma NBGM1/H11 produces an $IgM_k$ that was re-engineered into a Fab format to make VB6-011 (see U.S. Pat. No. 6,207,153 or WO 97/44461 for detail on the preparation of the H11 antibody-secreting hybridoma). The amino acid sequence and nucleotide sequence of VB6-011 is shown in FIG. 15 (SEQ ID NO:28 and SEQ ID NO:27, respectively).

In a specific, non-limiting embodiment, the cytotoxin comprises VB6-845 (FIG. 3B, SEQ ID No.16) or VB6-011 (FIG. 15, SEQ ID NO: 28). In other non-limiting embodiments, the cytotoxin comprises a variant of VB6-845 or VB6-011.

A VB6-845 variant binds to the same Ep-CAM epitope or to a substantially similar Ep-CAM epitope that is bound by VB6-845, and the variant may competitively inhibit VB6-845 binding to Ep-CAM, under physiologic conditions, by at least 10%, 15%, 20%, 25%, 30%, 35%, 40%, 45%, 50%, 55%, 60%, 65%, 70%, 75%, 80%, 85%, 90%, or 95%. A VB6-845 variant may comprise the same modified bouganin as VB6-845, or may comprise a different modified bouganin of the invention. In another non-limiting embodiment, the cytotoxin comprises an Ep-CAM-binding portion comprising the variable region of MOC31, or a variant thereof. In yet another embodiment, the cytotoxin comprises an Ep-CAM-binding portion comprising 4D5MOCB, or a variant thereof. Binding of any of these cytotoxins to Ep-CAM may be reduced by at least 10%, 15%, 20%, 25%, 30%, 35%, 40%, 45%, 50%, 55%, 60%, 65%, 70%, 75%, 80%, 85%, 90%, or 95% by competition with the reference MOC31 or 4D5MOCB antibody under physiologic conditions.

A VB6-011 variant binds to the same tumor-associated-antigen epitope or to a substantially similar tumor-associated-antigen epitope that is bound by VB6-011, and the variant may competitively inhibit VB6-011 binding to tumor-associated-antigen, under physiologic conditions, by at least 10%, 15%, 20%, 25%, 30%, 35%, 40%, 45%, 50%, 55%, 60%, 65%, 70%, 75%, 80%, 85%, 90%, or 95%. A VB6-011 variant may comprise the same modified bouganin as VB6-011, or may comprise a different modified bouganin of the invention. In another non-limiting embodiment, the cytotoxin comprises a tumor-associated-antigen binding portion comprising the H11 monoclonal antibody, H11 antigen binding fragments, or variants thereof. Binding of any of these cytotoxins to VB6-011 may be reduced by at least 10%, 15%, 20%, 25%, 30%, 35%, 40%, 45%, 50%, 55%, 60%, 65%, 70%, 75%, 80%, 85%, 90%, or 95% by competition with the reference H11 antibody under physiologic conditions.

In a preferred embodiment, the binding affinity of the Ep-CAM-binding portion or the tumor-associated-antigen-binding portion is at least four orders of magnitude, preferably at least three orders of magnitude, more preferably less than two orders of magnitude of the binding affinity of VB6-845 or VB6-011 respectively as measured by standard laboratory techniques. In non-limiting embodiments, the Ep-CAM-binding portion may competitively block the binding of a known anti-Ep-CAM antibody, such as, but not limited to, PANOREX® or MT201, to Ep-CAM, under physiologic conditions, by at least 0.1%, 1%, 10%, 15%, 20%, 25%, 30%, 35%, 40%, 45%, 50%, 55%, 60%, 65%, 70%, 75%, 80%, 85%, 90%, or 95%. In non-limiting embodiments, the tumor-associated-antigen-binding portion may competitively block the binding of a known anti-tumor-associated-antigen antibody, such as, but not limited to, H11, to tumor-associated antigen, under physiologic conditions, by at least 0.1%, 1%, 10%, 15%, 20%, 25%, 30%, 35%, 40%, 45%, 50%, 55%, 60%, 65%, 70%, 75%, 80%, 85%, 90%, or 95%.

The skilled artisan would appreciate that specificity determining residues can be identified. The term "specificity determining residue," also known as "SDR," refers to a residue that forms part of the paratope of an antibody, particularly CDR residues, the individual substitution of which by alanine, independently of any other mutations, diminishes the affinity of the antibody for the epitope by at least 10 fold, preferably by at least 100 fold, more preferably by at least 1000 fold. This loss in affinity underscores that residue's importance in the ability of the antibody to bind the epitope. See, e.g., Tamura et al., 2000, "Structural correlates of an anticarcinoma antibody: identification of specificity-determining residues (SDRs) and development of a minimally immunogenic antibody variant by retention of SDRs only," J. Immunol. 164(3):1432-1441.

The effect of single or multiple mutations on binding activity, particularly on binding affinity, may be evaluated contemporaneously to assess the importance of a particular series of amino acids on the binding interaction (e.g., the contribution of the light or heavy chain CDR2 to binding). Effects of an amino acid mutation may also be evaluated sequentially to assess the contribution of a single amino acid when assessed individually. Such evaluations can be performed, for example, by in vitro saturation scanning (see, e.g., U.S. Pat. No. 6,180,341; Hilton et al., 1996, "Saturation mutagenesis of the WSXWS motif of the erythropoietin receptor," J Biol Chem. 271:4699-4708) and site-directed mutagenesis (see, e.g., Cunningham and Wells, 1989, "High-resolution epitope mapping of hGH-receptor interactions by alanine-scanning mutagenesis," Science 244:1081-1085; Bass et al., 1991, "A systematic mutational analysis of hormone-binding determinants in the human growth hormone receptor," Proc Natl Acad Sci. USA 88:4498-4502). In the alanine-scanning mutagenesis technique, single alanine mutations are introduced at multiple residues in the molecule, and the resultant mutant molecules are tested for biological activity to identify amino acid residues that are critical to the activity of the molecule.

Sites of ligand-receptor or other biological interaction can also be identified by physical analysis of structure as determined by, for example, nuclear magnetic resonance, crystallography, electron diffraction, or photoaffinity labeling, in conjunction with mutation of putative contact site amino acids (see, e.g., de Vos et al., 1992, "Human growth hormone and extracellular domain of its receptor: crystal structure of the complex," Science 255:306-312; Smith et al., 1992, "Human interleukin 4. The solution structure of a four-helix bundle protein," J Mol Biol. 224:899-904; Wlodaver et al., 1992, "Crystal structure of human recombinant interleukin-4 at 2.25 A resolution," FEBS Lett. 309:59-64). Additionally, the importance of particular individual amino acids, or series of amino acids, may be evaluated by comparison with the amino acid sequence of related polypeptides or analogous binding sites.

Furthermore, the skilled artisan would appreciate that increased avidity may compensate for lower binding affinity. The avidity of a cytotoxin for a cancer cell receptor is a measure of the strength of the Ep-CAM-binding portion's binding of Ep-CAM, which has multiple binding sites. The functional binding strength between Ep-CAM and the Ep-CAM-binding portion represents the sum strength of all the affinity bonds, and thus an individual component may bind with relatively low affinity, but a multimer of such components may demonstrate potent biological effect. In fact, the multiple interactions between Ep-CAM-binding sites and Ep-CAM epitopes may demonstrate much greater than additive biological effect, i.e., the advantage of multivalence can be many orders of magnitude with respect to the equilibrium constant.

Similarly, the avidity of a cytotoxin for a cancer cell receptor is a measure of the strength of the tumor-associated antigen-binding portion's binding of tumor-associated antigen, which may have multiple binding sites. The functional binding strength between tumor-associated antigen and the tumor-associated antigen-binding portion represents the sum strength of all the affinity bonds, and thus an individual component may bind with relatively low affinity, but a multimer of such components may demonstrate potent biological effect. In fact, the multiple interactions between tumor-associated antigen-binding sites and tumor-associated antigen epitopes may demonstrate much greater than additive biological effect, i.e., the advantage of multivalence can be many orders of magnitude with respect to the equilibrium constant.

In one non-limiting embodiment, the Ep-CAM-binding portion has a structure substantially similar to that of 4D5MOCB. The substantially similar structure can be characterized by reference to epitope maps that reflect the binding points of the cytotoxin's Ep-CAM-binding portion to an Ep-CAM molecule. In another non-limiting embodiment, epitope maps can be generated for the tumor-associated antigen binding portion and a substantially similar structure can be characterized by reference to epitope maps that reflect the binding points of the cytotoxin's tumor-associated antigen binding portion to a tumor-associated antigen molecule.

The cytotoxins of the present invention may be prepared by chemical synthesis using techniques well known in the chemistry of proteins such as solid phase synthesis (Merrifield, J. Am. Chem. Assoc. 85:2149-2154 (1964)) or synthesis in homogenous solution (Houbenweyl, Methods of Organic Chemistry, ed. E. Wansch, Vol. 15 I and II, Thieme, Stuttgart (1987)). In one embodiment, the cancer-binding ligand and modified bouganin are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the ligand or toxin. In addition, if there are no reactive groups a photoactivatible crosslinker can be used. In certain instances, it may be desirable to include a spacer between the ligand and the toxin. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

A ligand-bouganin toxin fusion protein may also be prepared using recombinant DNA techniques. In such a case a DNA sequence encoding the cancer-binding ligand is fused to a DNA sequence encoding the modified bouganin protein, resulting in a chimeric DNA molecule. The chimeric DNA sequence is transfected into a host cell that expresses the ligand-bouganin fusion protein. The fusion protein can be recovered from the cell culture and purified using techniques known in the art.

Antibodies having specificity for cell surface proteins such as Ep-CAM and tumor-associated antigen may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody-producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495497 (1975)) as well as other techniques such as the human B-cell hybridoma technique (Kozbor et al., *Immunol. Today* 4:72 (1983)), the EBV-hybridoma technique to produce human monoclonal antibodies (Cole et al., Monoclonal Antibodies in Cancer Therapy Allen R., Bliss, Inc., pages 77-96 (1985)), and screening of combinatorial antibody libraries (Huse et al., *Science* 246:1275 (1989)). Hybridoma cells can be screened immunochemically for production of antibodies specifically reactive with the peptide and the monoclonal antibodies can be isolated.

The term "antibody" as used herein is intended to include monoclonal antibodies and polyclonal antibodies, antibody fragments (e.g. Fab and F(ab')$_2$, and single chain antibodies (scFv)), and chimeric antibodies which also specifically react with a cell surface component. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments. Single chain antibodies combine the antigen-binding regions of an antibody on a single stably folded polypeptide chain. Single chain antibodies can be generated by recombinant technology.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a cell surface antigen (See, for example, Morrison et al., *Proc. Natl Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., E.P. Patent No. 171,496; European Patent No. 173,494, United Kingdom Patent No. GB 2177096B). It is expected that chimeric antibodies would be less immunogenic in a human subject than the corresponding non-chimeric antibody. Chimeric antibodies can be stabilized by the method described in Pluckthun et al., WO 00/61635.

Monoclonal or chimeric antibodies specifically reactive against cell surface components can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g. Teng et al., *Proc. Natl. Acad. Sci. U.S.A.*, 80:7308-7312 (1983); Kozbor et al., *Immunology Today* 4:7279 (1983); Olsson et al., *Meth. Enzymol.*, 92:3-16 (1982), and PCT Publication WO92/06193 or EP 239,400). Humanized antibodies can also be commercially produced (Scotgen Limited, 2 Holly Road, Twickenham, Middlesex, Great Britain.) In addition, monoclonal or chimeric antibodies specifically reactive against cell surface components can be made less immunogenic by reducing their number of potential T-cell epitopes.

Specific antibodies, or antibody fragments, reactive against cell surface components may also be generated by screening expression libraries encoding immunoglobulin genes, or portions thereof, expressed in bacteria with cell surface components. For example, complete Fab fragments, VH regions and Fv regions can be expressed in bacteria using phage expression libraries (See for example Ward et al., *Nature* 341:544-546 (1989); Huse et al., *Science* 246: 1275-1281 (1989); and McCafferty et al., *Nature* 348:552-554 (1990)). Alternatively, a SCID-hu mouse, for example the model developed by Genpharm, can be used to produce antibodies, or fragments thereof.

In all instances where a modified bouganin protein is made in fusion with an antibody sequence it is most desired to use antibody sequences in which T cell epitopes or sequences able to bind MHC class II molecules or stimulate T cells or bind to T cells in association with MHC class II molecules have been removed.

A further embodiment of the present invention, the modified bouganin protein may be linked to a non-antibody protein yet a protein able to direct a specific binding interaction to a particular target cell. Such protein moieties include a variety of polypeptide ligands for which there are specific cell surface receptors and include therefore numerous cytokines, peptide and polypeptide hormones and other biological response modifiers. Prominent examples include such proteins as vascular epithelial growth factor, epidermal growth factor, heregulin, the interleukins, interferons, tumour necrosis factor and other protein and glycoprotein molecules. Fusion proteins of these and other molecules with bouganin of the present invention may be contemplated and may comprise the modified bouganin moiety in either the N-terminal or C-terminal orientation with respect to the protein ligand domain. Equally, chemical cross-linking of the purified ligand to the modified bouganin protein may be contemplated and within the scope of the present invention.

In a further embodiment the modified bouganin protein of the present invention may be used as a complex containing a water soluble polymer such as hydroxypropylmethacrylamide or other polymers where the modified bouganin protein is in covalent attachment to the polymer or in a non-covalent binding interaction with the polymer. Such an embodiment may additionally include an antigen binding domain such as an antibody or a fragment of an antibody in combination with the polymer bouganin complex.

(C) Uses of the Cytotoxins

The modified bouganin proteins of the invention may be used to specifically inhibit or destroy mammalian cells affected by cancer. It is an advantage of the cytotoxins of the invention that they have less immunogenicity, allowing the RIP to enter the cell and effectively kill the cancer cell. Thus, the cytotoxin may be used to specifically target cancer cells. The bouganin, once in the cancer cell, depurinates the major ribosomal RNA, thereby damaging the ribosomes and leading to a cessation of protein synthesis and cell death.

Accordingly, in one embodiment, the invention provides a method of inhibiting or destroying a cancer cell comprising administering a cytotoxin of the invention to an animal in need thereof. The present invention also includes a use of a cytotoxin of the invention to inhibit or destroy a cancer cell. The present invention further includes a use of a cytotoxin of the invention in the manufacture of a medicament to inhibit or destroy a cancer cell. The type of cancer cells that are inhibited or destroyed by a cytotoxin will be determined by the antigen specificity of its antibody portion.

In another embodiment, the invention provides a method of inhibiting or destroying cancer cells comprising the steps of preparing a cytotoxin of the invention and administering the cytotoxin to the cells. The cancer can be any type of cancer, including, but not limited to, colorectal cancer, breast cancer, ovarian cancer, pancreatic cancer, head and neck cancer, bladder cancer, liver cancer, renal cancer, melanomas, gastrointestinal cancer, prostate cancer, small cell and non small cell lung cancer, sarcomas, gliomas, T- and B-cell lymphomas.

The ability of the cytotoxins of the invention to selectively inhibit or destroy animal cancer cells may be readily tested in vitro using animal cancer cell lines. The selective inhibitory effect of the cytotoxins of the invention may be determined, for example, by demonstrating the selective inhibition of cellular proliferation in cancer cells.

Toxicity may be measured based on cell viability, for example the viability of normal and cancerous cell cultures exposed to the cytotoxins may be compared. Cell viability may be assessed by known techniques, such as trypan blue exclusion assays.

In another example, a number of models may be used to test the cytotoxicity of cytotoxins. Thompson, E. W. et al. (*Breast Cancer Res. Treatment* 31:357-370 (1994)) has described a model for the determination of invasiveness of human breast cancer cells in vitro by measuring tumour cell-mediated proteolysis of extracellular matrix and tumour cell invasion of reconstituted basement membrane (collagen, laminin, fibronectin, Matrigel or gelatin). Other applicable cancer cell models include cultured ovarian adenocarcinoma cells (Young, T. N. et al. *Gynecol. Oncol.* 62:89-99 (1996); Moore, D. H. et al. *Gynecol. Oncol.* 65:78-82 (1997)), human follicular thyroid cancer cells (Demeure, M. J. et al., *World J. Surg.* 16:770-776 (1992)), human melanoma (A-2058) and fibrosarcoma (HT-1080) cell lines (Mackay, A. R. et al. *Lab. Invest.* 70:781-783 (1994)), and lung squamous (HS-24) and adenocarcinoma (SB-3) cell lines (Spiess, E. et al. *J. Histochem. Cytochem.* 42:917-929 (1994)). An in vivo test system involving the implantation of tumours and measurement of tumour growth and metastasis in athymic nude mice has also been described (Thompson, E. W. et al., *Breast Cancer Res. Treatment* 31:357-370 (1994); Shi, Y. E. et al., *Cancer Res.* 53:1409-1415 (1993)).

The present invention also relates to a method of treating cancer comprising administering an effective amount of one or more cytotoxins of the present invention to an animal in need thereof. The invention includes a use of a cytotoxin of the invention to treat cancer. The invention further includes a use of a cytotoxin of the invention in the manufacture of a medicament for treating cancer.

The term "animal" includes all members of the animal kingdom, including humans.

The term "treating cancer" or "treat cancer" refers to inhibition of cancer cell replication, inhibition of cancer spread (metastasis), inhibition of tumor growth, reduction of cancer cell number or tumor growth, decrease in the malignant grade of a cancer or improvement of cancer related symptoms.

In a preferred embodiment, the animal is human. In another embodiment, the cancer is selected from the group consisting of colorectal cancer, breast cancer, ovarian cancer, pancreatic cancer, head and neck cancer, bladder cancer, liver cancer, renal cancer, melanomas, gastrointestinal cancer, prostate cancer, small cell and non small cell lung cancer, sarcomas, gliomas and T- and B-cell lymphomas.

Clinical outcomes of cancer treatments using a cytotoxin of the invention are readily discernible by one of skill in the relevant art, such as a physician. For example, standard medical tests to measure clinical markers of cancer may be strong indicators of the treatment's efficacy. Such tests may include, without limitation, physical examination, performance scales, disease markers, 12-lead ECG, tumor measurements, tissue biopsy, cytoscopy, cytology, longest diameter of tumor calculations, radiography, digital imaging of the tumor, vital signs, weight, recordation of adverse events, assessment of infectious episodes, assessment of concomitant medications, pain assessment, blood or serum chemistry, urinalysis, CT scan, and pharmacokinetic analysis. Furthermore, synergistic effects of a combination therapy comprising the cytotoxin and another cancer therapeutic may be determined by comparative studies with patients undergoing monotherapy.

Remission malignant tumors may be evaluated using criteria accepted by the skilled artisan. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2;92(3):205-16.

The effective dose of a specific cytotoxin construct may depend on various factors, including the type of cancer, the size of the tumour, the stage of the cancer, the cytotoxin's toxicity to the patient, the specificity of targeting to cancer cells, as well as the age, weight, and health of the patient.

Cytotoxins comprising the modified bouganin can be administered by i.v. infusion over a period of minutes to hours, depending on the dose and the concentration of the cytotoxin in the infusate.

In one embodiment, the cytotoxin is infused over a period of 3 hours.

In one embodiment, the effective dose by i.v. administration of cytotoxin may range from about 1 to 100 mg/kg/dose. In other embodiments, the dose may range from approximately 2 to 50 mg/kg/dose. In specific embodiments, the dose may be at least approximately 2, 4, 8, 13, 20, 28, 40, 50 mg/kg/dose.

In one embodiment, the single dose is administered approximately every week for approximately 1, 2, 3, 4, 5, or 6 weeks. The single dose can be administered in consecutive weeks or, alternatively, one or more weeks can be skipped. After this cycle, a subsequent cycle may begin approximately 1, 2, 4, 6, or 12 weeks later. The treatment regime may include 1, 2, 3, 4, 5, 6 or more cycles, each cycle being spaced apart by approximately 1, 2, 4, 6, or 12 weeks.

In another embodiment the single dose is administered every month for approximately 1, 2, 3, 4, 5, or 6 consecutive months. After this cycle, a subsequent cycle may begin approximately 1, 2, 4, 6, or 12 months later. The treatment regime may include 1, 2, 3, 4, 5, 6 or more cycles, each cycle being spaced apart by approximately 1, 2, 4, 6, or 12 months.

In a particular non-limiting embodiment, the effective dose of the cytotoxin is between about 1 and 50 mg/kg/tumor/day, wherein the patient is administered a single dose per day. The single dose is administered approximately every day (one or more days may optionally be skipped) for approximately 1, 2, 3, 4, 5, 6 or 7 consecutive days. After this cycle, a subsequent cycle may begin approximately 1, 2, 3, 4, 5, or 6 weeks later. The treatment regime may include 1, 2, 3, 4, 5, 6 or more cycles, each cycle being spaced apart by approximately 1, 2, 3, 4, 5, or 6 weeks.

The injection volume preferably is at least an effective amount, which is appropriate to the type and/or location of the tumor. The maximum injection volume in a single dose may be between about 25% and 75% of tumor volume, for example approximately one-quarter, one-third, or three-quarters of the estimated target tumor volume. In a specific, non-limiting embodiment, the maximum injection volume in a single dose is approximately 30% of the tumor volume.

In another embodiment, the cytotoxin is infused for 3 hours at a rate of 100 cc per hour with a solution containing from 1 to 10 mg cytotoxin/mL. The cytotoxin will be diluted in a suitable physiologically compatible solution.

The effective dose of another cancer therapeutic to be administered together with a cytotoxin during a cycle also varies according to the mode of administration. The one or more cancer therapeutics may be delivered intratumorally, or by other modes of administration. Typically, chemotherapeutic agents are administered systemically. Standard dosage and treatment regimens are known in the art (see, e.g., the latest editions of the Merck Index and the Physician's Desk Reference; NCCN Practice Guidelines in Oncology)).

Combination therapy with a cytotoxin may sensitize the cancer or tumor to administration of an additional cancer therapeutic. Accordingly, the present invention contemplates combination therapies for preventing, treating, and/or preventing recurrence of cancer comprising administering an effective amount of a cytotoxin prior to, subsequently, or concurrently with a reduced dose of a cancer therapeutic. For example, initial treatment with a cytotoxin may increase the sensitivity of a cancer or tumor to subsequent challenge with a dose of cancer therapeutic. This dose is near, or below, the low range of standard dosages when the cancer therapeutic is administered alone, or in the absence of a cytotoxin. When concurrently administered, the cytotoxin may be administered separately from the cancer therapeutic, and optionally, via a different mode of administration.

In another embodiment, a cytotoxin is administered in combination with at least one other immunotherapeutic.

In another embodiment, a cytotoxin is administered in combination with a regimen of radiation therapy. The therapy may also comprise surgery and/or chemotherapy. For example, the cytotoxin may be administered in combination with radiation therapy and cisplatin (Platinol), fluorouracil (5-FU, Adrucil), carboplatin (Paraplatin), and/or paclitaxel (Taxol). Treatment with the cytotoxin may allow use of lower doses of radiation and/or less frequent radiation treatments, which may for example, reduce the incidence of severe sore throat that impedes swallowing function potentially resulting in undesired weight loss or dehydration.

In another embodiment, a cytotoxin is administered in combination with one or more cytokines which include, without limitation, a lymphokine, tumor necrosis factors, tumor necrosis factor-like cytokine, lymphotoxin, interferon, macrophage inflammatory protein, granulocyte monocyte colony stimulating factor, interleukin (including, without limitation, interleukin-1, interleukin-2, interleukin-6, interleukin-12, interleukin-15, interleukin-18), and a variant thereof, including a pharmaceutically acceptable salt thereof.

In yet another embodiment, a cytotoxin is administered in combination with a cancer vaccine including, without limitation, autologous cells or tissues, non-autologous cells or tissues, carcinoembryonic antigen, alpha-fetoprotein, human chorionic gonadotropin, BCG live vaccine, melanocyte lineage proteins, and mutated, tumor-specific antigens.

In yet another embodiment, a cytotoxin is administered in association with hormonal therapy. Hormonal therapeutics include, without limitation, a hormonal agonist, hormonal antagonist (e.g., flutamide, tamoxifen, leuprolide acetate (LUPRON)), and steroid (e.g., dexamethasone, retinoid, betamethasone, cortisol, cortisone, prednisone, dehydrotestosterone, glucocorticoid, mineralocorticoid, estrogen, testosterone, progestin).

In yet another embodiment, a cytotoxin is administered in association with a gene therapy program to treat or prevent cancer.

In yet another embodiment, an Ep-CAM-targeted cytotoxin is administered in combination with one or more agents that increase expression of Ep-CAM in the tumor cells of interest. Ep-CAM expression preferably is increased so that a greater number of Ep-CAM molecules are expressed on the tumor cell surface. For example, the agent may inhibit the normal cycles of Ep-CAM antigen endocytosis. Such combination treatment may improve the clinical efficacy of the Ep-CAM-targeted cytotoxin alone, or with other cancer therapeutics or radiation therapy. In specific, nonlimiting embodiments, the agent which increases Ep-CAM expression in the tumor cells is vinorelbine tartrate (Navelbine) and/or paclitax (Taxol). See, e.g., Thurmond et al., 2003, "Adenocarcinoma cells exposed in vitro to Navelbine or Taxol increase Ep-CAM expression through a novel mechanism." Cancer Immunol Immunother. July;52(7):429-37.

Combination therapy may thus increase the sensitivity of the cancer or tumor to the administered cytotoxin and/or additional cancer therapeutic. In this manner, shorter treatment cycles may be possible thereby reducing toxic events. Accordingly, the invention provides a method for treating or preventing cancer comprising administering to a patient in need thereof an effective amount of a cytotoxin and at least one other cancer therapeutic for a short treatment cycle. The cycle duration may vary according to the specific cancer therapeutic in use. The invention also contemplates continuous or discontinuous administration, or daily doses divided into several partial administrations. An appropriate cycle duration for a specific cancer therapeutic will be appreciated by the skilled artisan, and the invention contemplates the continued assessment of optimal treatment schedules for each cancer therapeutic. Specific guidelines for the skilled artisan are known in the art. See, e.g., Therasse et al., 2000, "New guidelines to evaluate the response to treatment in solid tumors. European Organization for Research and Treatment of Cancer, National Cancer Institute of the United States, National Cancer Institute of Canada," J Natl Cancer Inst. February 2;92(3):205-16.

Alternatively, longer treatment cycles may be desired. Accordingly, the cycle duration may range from approximately 10 to 56, 12 to 48, 14 to 28, 16 to 24, or 18 to 20 days. The cycle duration may vary according to the specific cancer therapeutic in use.

The present invention contemplates at least one cycle, preferably more than one cycle during which a single cancer therapeutic or series of therapeutics is administered. An appropriate total number of cycles, and the interval between cycles, will be appreciated by the skilled artisan. The number of cycles may be 1, 2, 3, 4, 5, 6, 7, 8, 9, 10, 11, 12, 13, 14, 15, 16, 17, 18, 19, 20, or 21 cycles. The interval between cycles may be 1, 2, 3, 4, 5, 6, 7, 8, 9, 10, 11, 12, 13, 14, 15, 16, 17, 18, 19, 20, or 21 days. The invention contemplates the continued assessment of optimal treatment schedules for each cytotoxin and additional cancer therapeutic.

In another embodiment, a process is provided for preparing a pharmaceutical for treating a mammal with cancer comprising the steps of identifying T-cell epitopes of bouganin having reduced propensity for activated T-cells; preparing a cytotoxin of the invention having one or more of the T-cell epitopes and suspending the protein in a pharmaceutically acceptable carrier, diluent or excipient.

The invention also provides a pharmaceutical composition for treating a mammal with cancer comprising a cytotoxin of the invention and a pharmaceutically acceptable carrier, diluent or excipient.

The cytotoxins of the invention may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, intramuscular, etc.), oral administration, inhalation, transdermal administration (such as topical cream or ointment, etc.), or suppository applications. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The pharmaceutical compositions may be used in methods for treating animals, including mammals, preferably humans, with cancer. It is anticipated that the compositions will be particularly useful for treating patients with colorectal cancer, breast cancer, ovarian cancer, pancreatic cancer, head and neck cancer, bladder cancer, gastrointestinal cancer, prostate cancer, small cell and non small cell lung cancer, sarcomas, gliomas, T- and B-cell lymphomas. The dosage and type of cytotoxin to be administered will depend on a variety of factors which may be readily monitored in human subjects. Such factors include the etiology and severity (grade and stage) of neoplasia.

Pharmaceutical compositions adapted for direct administration include, without limitation, lyophilized powders or aqueous or non-aqueous sterile injectable solutions or suspensions, which may further contain antioxidants, buffers, bacteriostats and solutes that render the compositions substantially isotonic with the blood of an intended recipient. Other components that may be present in such compositions include water, alcohols, polyols, glycerin and vegetable oils, for example. Extemporaneous injection solutions and suspensions may be prepared from sterile powders, granules and tablets. Cytotoxin may be supplied, for example but not by way of limitation, as a lyophilized powder which is reconstituted with sterile water or saline prior to administration to the patient.

Pharmaceutical compositions of the invention may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy) propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

In another embodiment, a pharmaceutical composition comprises a cytotoxin and one or more additional cancer therapeutics, optionally in a pharmaceutically acceptable carrier.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylarnino ethanol, histidine, procaine, etc.

In as far as this invention relates to modified bouganin, compositions containing such modified bouganin proteins or fragments of modified bouganin proteins and related compositions should be considered within the scope of the invention. A pertinent example in this respect could be development of peptide mediated tolerance induction strategies wherein one or more of the disclosed peptides is administered to a patient with immunotherapeutic intent. Accordingly, synthetic peptides molecules, for example one of more of comprising all or part of any of the epitope regions R1-R3 as defined above. Such peptides are considered embodiments of the invention.

In a further aspect of the present invention relates to methods for therapeutic treatment of humans using the modified bouganin compositions. For administration to an individual, any of the modified compositions would be produced to be preferably at least 80% pure and free of pyrogens and other contaminants.

The present invention also provides a kit comprising an effective amount of a cytotoxin, optionally, in combination with one or more other cancer therapeutics, together with instructions for the use thereof to treat the cancer.

(D) T-cell Epitope Peptides

An additional embodiment of the invention is a T-cell epitope peptide. In an example, the T-cell epitope peptide is able to evoke a stimulation index of greater than 1.8 in a T-cell assay, more preferably greater than 2.0. The T-cell epitope peptide of the invention is able to bind MHC class II.

In an embodiment of the invention the T-cell epitope peptide comprises at least 9 consecutive amino acid residues from any of the sequences of R1, R2 or R3 (above). In another embodiment, the T-cell epitope peptide sequence has greater than 90% amino acid identity with any one of the peptide sequences R1, R2 or R3; more preferably the T-cell epitope peptide has greater than 80% amino acid identity with any one of the peptide sequences R1, R2 or R3.

The term "peptide" as used herein is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acids, whereas an "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited.

Another embodiment of the invention is the use of the T-cell epitope peptides of the invention to make the modified bouganin proteins of the invention and modified T-cell epitope peptides.

A further embodiment of the invention is a modified T-cell epitope peptide that is modified such that the modified T-cell epitope peptide has reduced propensity to activate human T cells than the non-modified T-cell epitope peptide. In an example, the modified T-cell epitope peptides of the invention contains modifications such that when tested in a T-cell assay evokes a reduced stimulation index in comparison to the non-modified T-cell epitope peptide.

In an embodiment of the invention the modified T-cell epitope peptide has the following sequence:

AKX$^1$DRKX$^2$LX$^3$LGVX$^4$KL wherein at least one of X$^1$, X$^2$, X$^3$, and X$^4$ is modified from the non-modified sequence, as follows:
X$^1$ is T or A or Q;
X$^2$ is G or A;
X$^3$ is Q or G; and
X$^4$ is N or D or T or A or R or Q or E or G or H or K or S (SEQ ID NO:8).

In another embodiment of the invention the modified T-cell epitope peptide has the following sequence:

LGVX$^4$KLEFSIEAIHG wherein X$^4$ is N or D or T or A or R or Q or E or G or H or K or S (SEQ ID NO:9).

In a further embodiment of the invention the modified T-cell epitope peptide has the following sequence:

NGQEX$^5$AKFFLIVIQM wherein X$^5$ is Q or A (SEQ ID NO:10).

The invention also provides nucleic acid molecules encoding the T-cell epitope peptides or modified T-cell epitope peptides of the invention.

The following figures, sequence listings and examples are provided to aid the understanding of the present invention. It is understood that modifications can be made in the procedures set forth without departing from the spirit of the invention.

The following non-limiting examples are illustrative of the present invention:

EXAMPLES

Example 1

Method of Mapping Epitopes in Bouganin using Naïve Human T-cell Proliferation Assays Peptides covering the sequence of the mature bouganin protein, as described by Den Hartog et al [ibid] were synthesized. The length of each peptide is 15 amino acids, and successive peptides overlap by 12 residues. The sequence of these peptides and their numbering is indicated in TABLE 1.

The peptides were used in T-cell proliferation assays with PBMCs (peripheral blood mononuclear cells) from naïve donors (i.e. no known sensitization to bouganin). 20 donor PBMC were selected to get an optimal coverage of MHC class II allotypes. The allotypic coverage is in excess of 85%. The HLA-DR allotypes are shown in TABLE 2.

PBMCs were stimulated with individual peptides in triplicate cultures for 7 days before proliferation was assessed by $^3$H-thymidine ($^3$H-Thy) incorporation. All peptides were tested at two different concentrations (1 µM and 5 µM). Stimulation indices (S.I.) were calculated as the amount of $^3$H incorporated, divided by the amount of $^3$H incorporated in mock-stimulated control cells.

Buffy coats from human blood stored for less than 12 hours were obtained from the National Blood Service (Addenbrooks Hospital, Cambridge, UK). Ficoll-paque was obtained from Amersham Pharmacia Biotech (Amersham, UK). Serum free AIM V media for the culture of primary human lymphocytes and containing L-glutamine, 50 µg/ml streptomycin, 10 µg/ml gentomycin and 0.1% human serum albumin was from Gibco-BRL (Paisley, UK). Synthetic peptides were obtained from Eurosequence (Groningen, The Netherlands) and Babraham Technix (Cambridge, UK).

Erythrocytes and leukocytes were separated from plasma and platelets by gentle centrifugation of buffy coats. The top phase (containing plasma and platelets) was removed and discarded. Erythrocytes and leukocytes were diluted 1:1 in phosphate buffered saline (PBS) before layering onto 15 ml ficoll-paque (Amersham Pharmacia, Amersham UK). Centrifugation was done according to the manufacturers recommended conditions and PBMCs were harvested from the serum+PBS/ficoll paque interface. PBMCs were mixed with PBS (1:1) and collected by centrifugation. The supernatant was removed and discarded and the PBMC pellet resuspended in 50ml PBS. Cells were again pelleted by centrifugation and the PBS supernatant discarded. Cells were resuspended using 50 ml AIM V media and at this point counted and viability assessed using trypan blue dye exclusion. Cells were again collected by centrifugation and the supernatant discarded. Cells were resuspended for cryogenic storage at a density of $3\times10^7$ per ml. The storage medium was 90% (v/v) heat inactivated AB human serum (Sigma, Poole, UK) and 10% (v/v) DMSO (Sigma, Poole, UK). Cells were transferred to a regulated freezing container (Sigma) and placed at $-70°$ C. overnight. When required for use, cells were thawed rapidly in a water bath at 37° C. before transferring to 10 ml pre-warmed AIM V medium.

PBMC were stimulated with protein and peptide antigens in a 96 well flat bottom plate at a density of $2\times10^5$ PBMC per well. PBMC were incubated for 7 days at 37° C. before pulsing with $^3$H-Thy (Amersham-Pharmacia, Amersham, UK). Two control peptides termed C-32 and C-49 that have previously been shown to be immunogenic and a potent whole protein non-recall antigen Keyhole Limpet Hemocyanin (KLH) were used in each donor assay. C-32=sequence PKYVKQNTLKLAT from Flu haemagglutinin residues 307-319 (SEQ ID NO:127). C-49=sequence KVVDQIK-KISKPVQH from Chlamydia HSP 60 (SEQ ID NO:128).

Peptides were dissolved in DMSO to a final concentration of 10 mM, these stock solutions were then diluted 1/500 in AIM V media (final concentration 20 µM). Peptides were added to a flat bottom 96 well plate to give a final concentration of 1 and 5 µM in 100 µl. The viability of thawed PBMC's was assessed by trypan blue dye exclusion, cells were then resuspended at a density of $2\times10^6$ cells/ml, and 100 µl ($2\times10^5$ PBMC/well) was transferred to each well containing peptides. Triplicate well cultures were assayed at each peptide concentration. Plates were incubated for 7 days in a humidified atmosphere of 5% $CO^2$ at 37° C. Cells were pulsed for 18-21 hours with 1 µCi $^3$H-Thy/well before harvesting onto filter mats. CPM values were determined using a Wallac microplate beta top plate counter (Perkin Elmer). Results were expressed as stimulation indices, derived by division of the proliferation score (e.g. counts per minute of radioactivity) measured to the test peptide by the score measured in cells not contacted with a test peptide.

Compilation of the results of the above assay indicates the presence of four T cell epitopes, corresponding to peptides 41, 44 and 50 in the mature, processed region of the protein and peptide 88 in the unprocessed form. Since the epitope in peptide 88 is not part of the mature protein, it is ignored under the scheme of the present invention.

For peptide 41 (termed epitope region R1) there were four responsive donors to this peptide; donors 4, 5, 10 and 11. The S.I.s for these at 5 µM are 3.6, 4.9, 2.1 and 2.0 respectively.

For peptide 44 (termed epitope region R2). There are two responsive donors to this peptide; donors 4 (S.I.=3.5) and 11 (S.I.=2.3). Neighboring peptides 43 and 45 induced lower level T cell proliferation since both these peptides overlap by 12 amino acids with peptide 44.

For peptide 50 there were 2 responsive donors to this peptide; donors 4 (S.I.=2.9) and 14 (S.I.=2.0). Peptide 51 induced lower level T cell proliferation in donor 14 (S.I.>1.9).

The tissue types for all PBMC samples were assayed using a commercially available reagent system (Dynal, Wirral, UK). Assays were conducted in accordance with the suppliers recommended protocols and standard ancillary reagents and agarose electrophoresis systems. The allotypic specificities of each of the responsive donor samples is given in TABLE 2.

Example 2

Cloning of Bouganin from *Bougainvillea spectabilis*

Total RNA was extracted from the leaves of *Bougainvillea spectabilis* using the 'SV Total RNA Isolation System and protocols provided by the supplier (Promega, Southampton, UK). Fresh leaf tissue was ground to a fine powder under liquid nitrogen, and approximately 50 mg of ground tissue was used for the RNA isolation. RNA quality and quantity was checked by visualization on a 1% agarose gel, and the bouganin gene was amplified from the total RNA using the 'Access RT-PCR System' (Promega) using approximately 1 µg of RNA per reaction and with the gene specific primers OL1032 and OL1033. Primer sequences are given in TABLE 3 below. This reaction generated a 1242 bp fragment encompassing the native leader sequence and the full-length bouganin sequence. This fragment was cloned into the pGEM-T Easy vector (Promega), following kit instructions, and designated pBou1. The sequence was confirmed by DNA sequencing.

The bouganin gene was transferred into the pET21a (Novagen, Nottingham, UK) by PCR cloning using the pBou1 plasmid as a template. A pelB (pectate lyase) leader sequence was added to the 5' end, and a sequence encoding a 6x histidine tag was added to the 3' end of the bouganin coding sequence. The pelB leader was amplified from vector pPMI-his [Molloy, P. et al, (1995) *J. Applied Bacteriology*, 78: 359-365] using primer OL1322 (incorporating an Nde1 site) and primer OL1067. The bouganin-his fragment was amplified from pBou1 using OL1068 and OL1323 (incorporating a Not1 site). The pelB leader was fused in frame to the bouganin-his fragment using overlap PCR, and the resulting fragment cloned into pGEM-T Easy (Promega). Following sequence confirmation the pelB-bouganin-his fragment was cloned as a Nde1-Not1 fragment into Nde1-Not1 digested pET21a. This clone was designated pBou32.

Example 3

Construction of Mutant Bouganin Proteins

A number of modified (mutant) bouganin proteins were designed using data provided by the T-cell epitope mapping procedure and use of software able to simulate the binding of peptides with human MHC class II binding groove. This latter approach is described in detail elsewhere [WO 02/069232]. Variant genes were constructed and the mutant proteins tested for functional activity. In general, "single mutant" proteins containing one amino acid substitution each were first constructed and tested, then genes for active modified proteins combined to produce multiply substituted modified proteins.

Mutant genes were constructed using an overlap PCR procedure in which the mutant amino acid codon becomes introduced into the gene by use of a mutant in "overlap primer". The scheme is well understood in the art and is described in detail elsewhere [Higuchi, et al (1900) *Nucl. Acids Res.* 16:7351]. A total of 37 single mutant modified proteins were constructed and tested for retained functional activity. In addition, a negative control modified protein containing a substitution Y70A was also constructed and tested in all assays. One of the 37 "single mutant" modified proteins in fact contained two directly adjacent substitutions (E151T and I152E) and is counted herein as a single mutant. The substitutions tested and the corresponding activity values are given in TABLE 4.

A total of 11 multiple substitution modified proteins were constructed and tested for retained activity. The substitutions tested and the corresponding activity values are given in TABLE 5.

TABLE 6 describes the sequences of the substitution modified proteins. TABLE 7 lists some specific sequences.

In all instances, proteins were purified and tested according to the procedures outlined in examples 4 and 5 below.

Example 4

Expression of and Purification of Bouganin Protein

The plasmid pBou32 was transformed into BL21(DE3) (Novagen) competent cells following manufacturers instructions, and selected on LB (Invitrogen, Paisley, UK) plates containing 50 µg/ml carbenicillin. A fresh colony from this transformation was used to inoculate 5 ml 2×YT (Invitrogen) broth, without antibiotic, and this was grown with shaking at 250 rpm at 37° C. until OD600=1.5-2.0. The culture was then centrifuged at 2500 rpm for 15 minutes at room temperature, and the cells resuspended in 5 ml fresh 2×YT plus 1 mM IPTG. This culture was incubated at 30° C. with shaking at 300 rpm for 1.5 hours and the cells collected by centrifugation and the supernatant discarded.

The cell pellet was resuspended in 1 ml of PEB2 (50 mM Tris-HCl pH8, 20% sucrose, 1 mg/ml lysozyme, 1× Complete Protease Inhibitor Tablet (Roche, Lewes, UK), and incubated on ice for 1 hour with gentle mixing. The cell debris was centrifuged at 14,000 rpm at 4° C. and the pellet discarded. The resulting supernatant is now referred to as the 'periplasmic fraction'. Bouganin protein was purified from the periplasmic fraction by nickel affinity column chromatography using commercially available "spin column" and the manufacturer's instructions (Qiagen, Crawley, UK). The resulting material was dialyzed against 4 liters of phosphate buffered saline (0.138M NaCl, 0.0027M KCl, pH 7.4) overnight at 4° C. using a 10000 molecular weight cut-off 'Slide-A-Lyzer' (Pierce, Chester, UK). Following dialysis, the protein concentration was estimated using the Micro BCA Assay Kit (Pierce), and samples stored at −20° C.

Bouganin protein concentration was further determined using an ELISA based assay system. Briefly, antiserum against bouganin was generated (Genovac, Freiburg, Germany), through the genetic immunization of two rats with a plasmid expressing bouganin. For the ELISA, recombinant bouganin is captured onto Ni-agarose coated plates via its His-tag and subsequently detected with the rat antiserum and a secondary HRP-conjugated anti-rat Fc antibody (Sigma, Poole, UK). As a standard, a large preparation of the wild-type bouganin expressed in *E. coli* and quantitated using the total protein assay was used in each determination.

Example 5

Assay of Bouganin Activity

The activity of the wild-type and modified (mutant) bouganin proteins was tested by measuring their ability to inhibit protein synthesis in a cell-free protein synthesis assay.

A mixture of 10 µl TNT Coupled Transcription/Translation mix (Promega), 20 µM methionine, 120 ng pT7 luciferase DNA (Promega) and serial dilutions of WT and mutant bouganin protein in a final volume of 12.5 µl were incubated at 30° C. for one hour, after which the reaction was stopped by addition of 100 µl "SteadyGlow" luciferase assay reagent (Promega). The luciferase activity was measured using a Wallac luminescence counter. Active bouganin protein is detected as a decrease in measured luciferase activity. Each modified bouganin protein was tested in at least 5 concentrations, with each data point in duplicate. Positive and negative controls were included in each experiment.

Results for single mutant proteins are shown in TABLE 4. Results for multiple mutant modified bouganin proteins are shown in TABLE 5. In each instance results are expressed relative to wild-type protein activity. All assays were conducted with the inclusion of an inactive mutant bouganin protein with a Y70A substitution.

Figure 1:
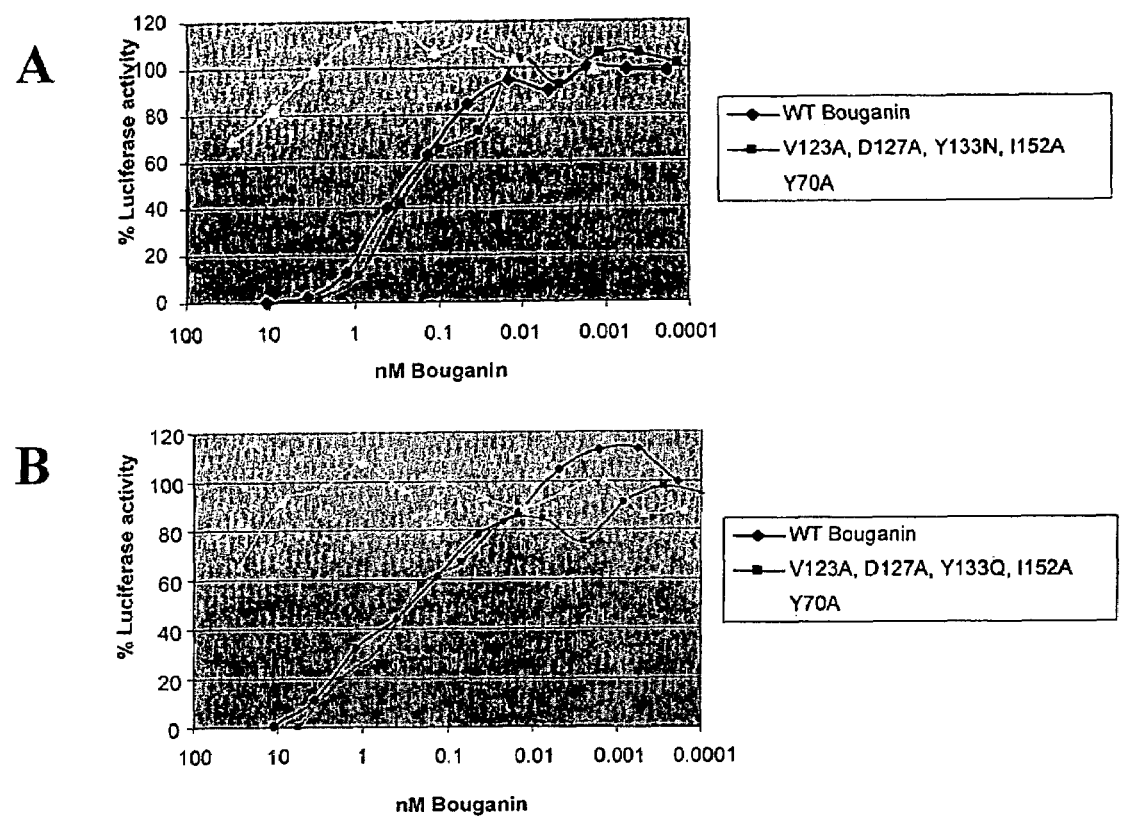

In addition, luciferase assay results may be plotted showing % luciferase activity relative to control versus protein concentration of added bouganin. Examples of such plots are shown in FIG. 1 depicting the results as determined for two different multiple mutant bouganin proteins.

Example 6

Assay of Variant Bouganin Sequences for Loss of T-cell Epitopes

The multiple modified protein designated Bou156 was selected for further testing using an immunogenicity assay. This variant contains the substitutions V123A, D127A, Y133N and I152A. Immunogenicity testing involves use of live cells that may be damaged by testing using whole bouganin protein, therefore these assays were conducted using synthetic peptides comprising the substitutions incorporated into variant Bou156. The peptides tested are listed in TABLE 8. The assays were conducted according to the procedures described in example 1 (above) using a PBMC donor pool of 20 individuals. Peptides were tested in triplicate for each donor sample at a two different final peptide concentrations (1 µM and 5µM).

The results are expressed as SI per peptide per donor sample and are shown in FIG. 2. Del-41 is peptide sequence AKADRKALELGVNKL (SEQ ID NO:29). Del-44 is peptide sequence LGVNKLEFSIEAIHG (SEQ ID NO:30). Del-50 is peptide sequence NGQEAAKFFLIVIQM (SEQ ID NO:31). None of the modified peptides induced a T cell response in any of the donors (S.I.<2). In contrast an immunogenic control peptide stimulated T cells of 6 donors (S.I.>2).

Example 7

VB6-845: Recombinant Engineering of an Ep-CAM-specific Fab Antibody for Optimal Delivery of De-immunized Bouganin (De-bouganin)

For this example and Example 8, the de-immunized bouganin used is Bou156.

Tumor-targeting cytotoxins are composed of the variable region of an antibody linked to a bacterial, fungal or plant toxin. The present study illustrates that the deimmunized bouganin constructs of the invention, comprising deimmunized bouganin linked to a targeting moiety have reduced immunogenicity, while still retaining their biological activity. TABLE 12 demonstrates the binding of the Ep-CAM antibody to several types of tumours and thus shows that it can be used to treat these types of cancers.

Figure 3C:
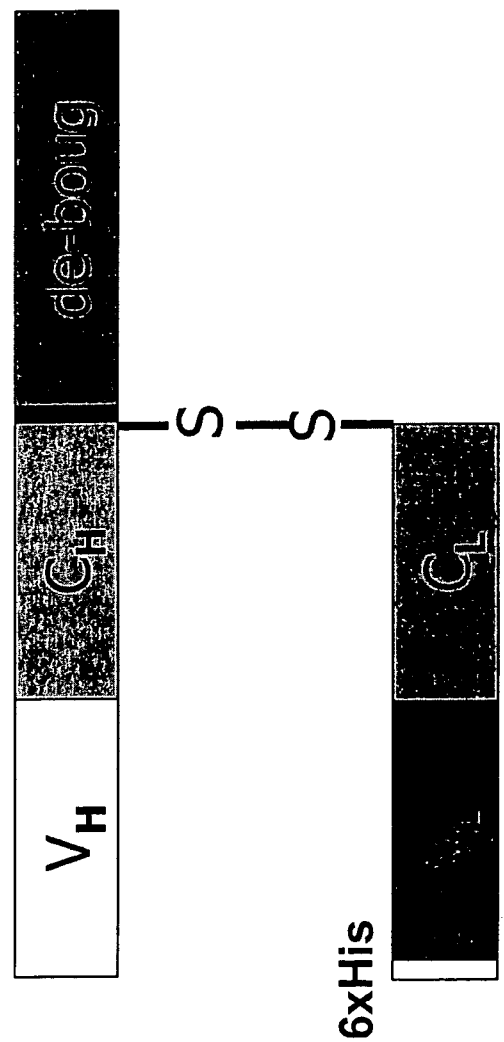
FIG. 3C illustrates the assembled VB6-845 protein without the pelB sequences.

De-immunized Bouqanin Construct: Ep-CAM Directed Targeting Moiety Linked to De-bouganin VB5-845, a Fab version of an anti-Ep-CAM scFv antibody, was genetically linked to a de-immunized form of bouganin (de-bouganin), Bou 156, a potent, plant-derived, type I ribosome-inactivating protein (RIP), to create the antibody-toxin construct VB6-845. FIG. 3 illustrates the construct VB6-845. FIG. 3A illustrates dicistronic unit of the pro-VB6-845, with pelB leader sequences. The amino acid sequence (SEQ ID NO:16) and nucleic acid coding sequence (SEQ ID NO:15) are provided in FIG. 3B. FIG. 3C illustrates the assembled VB6-845 protein, which is described below in more detail. Testing of this construct, illustrate that the construct retained its biological activity (cytoxicity) and the specificity of the targeting moiety (Ep-CAM antibody).

Orientation of the De-immunized Boucianin Construct

To determine the optimal antibody-de-bouganin orientation, several forms of a dicistronic expression unit were generated, expressed and tested for potency.

Figure 4:
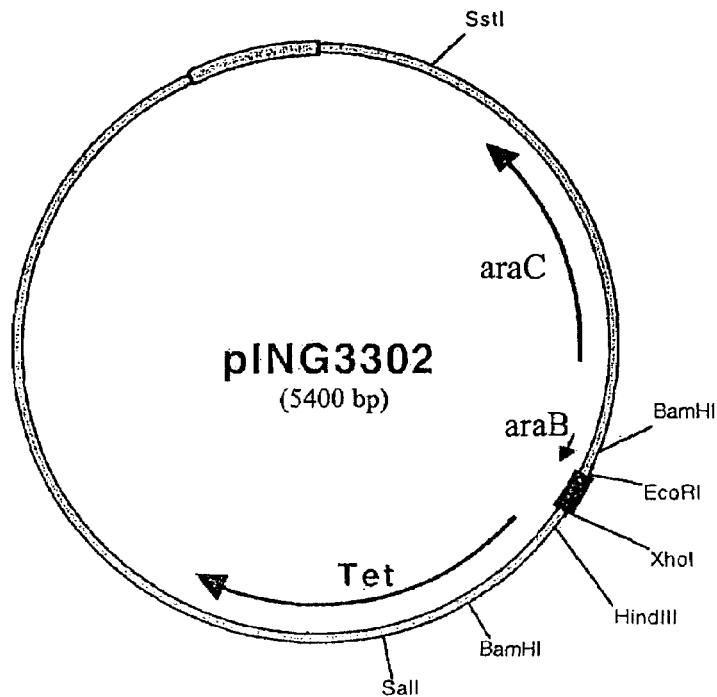
FIG. 4 illustrates the map of the expression vector pING3302. Inserts of the examples were ligated in 3302 vector using EcoRI and XhoI restriction sites.

In each case, the dicistronic unit was cloned into the pING3302 vector (FIG. 4) under the control of the arabinose—inducible araBAD promoter and transformed in E104 E. coli. Upon induction, the presence of the pelB leader sequence directed the secretion of the Fab-de-bouganin fusion protein into the culture supernatant. The cleavable linker enabled the de-bouganin to cleave from the targeting moiety and exert its biological activity. In one embodiment the linker is a furin linker, although a person skilled in the art would appreciate that other cleavable linkers could be suitable. Preferred linkers could be selected based on target specificity, and environment. A sample of the constructs made and tested are as follows:

FIG. 3: VB6-845, wherein the de-bouganin (Bou156) is linked to the C-terminus of the CH domain via a furin linker. FIG. 3A illustrates the dicistronic unit of the pro-sequences, FIG. 3B illustrates the nucleic acid coding sequence (SEQ ID NO:15) and the amino acid sequence of the pro-sequences (SEQ ID NO:16) and FIG. 3C illustrates the assembled VB6-845 protein without the pelB sequences.

Figure 5A:
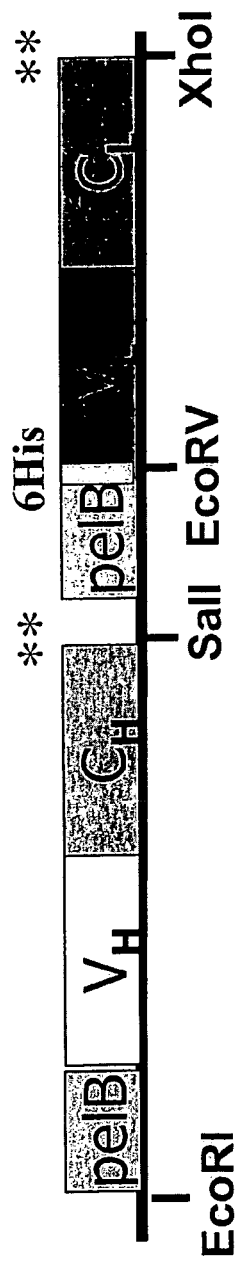
FIG. 5A illustrates the dicistronic unit encoding the pro-sequences.
Figure 5C:
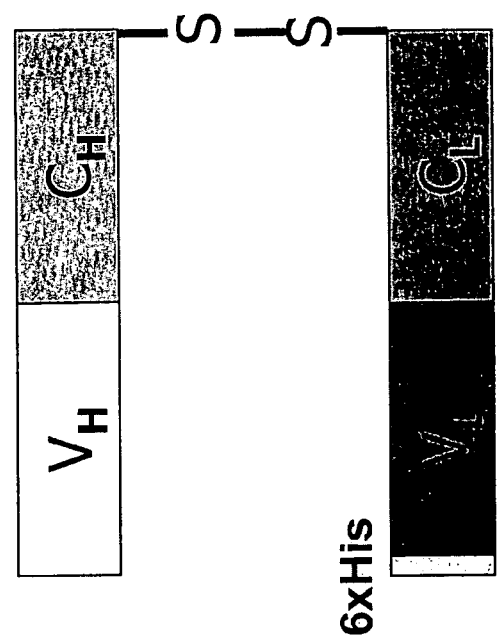
FIG. 5C illustrates the assembled VB5-845 protein without the pelB sequences.

FIG. 5 illustrates the control Fab anti-Ep-CAM construct without the plant toxin, de-bouganin (VB5-845). FIG. 5A illustrates the dicistronic unit of the pro-sequences, FIG. 5B illustrates the nucleic acid coding sequence (SEQ ID NO:17) and the amino acid sequence of the pro-sequences (SEQ ID NO:18) and FIG. 5C illustrates the assembled VB6 845 protein without the pelB sequences.

Figure 6A:
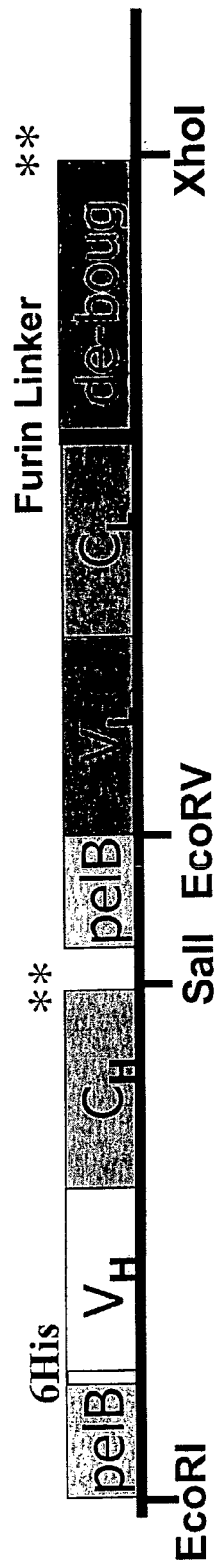
FIG. 6A illustrates the dicistronic units encoding the pro-sequences.
Figure 6C:
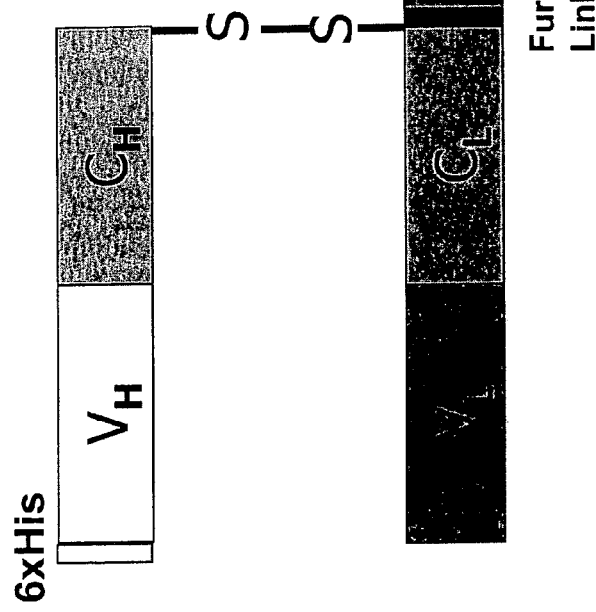
FIG. 6C illustrates the assembled VB6-845-C$_L$-de-bouganin protein without the pelB sequences.

FIG. 6 illustrates the Fab anti-Ep-CAM de-bouganin construct, VB6-845-$C_L$-de-bouganin, wherein the Bou156 is linked at the C-terminus of the $C_L$ domain. FIG. 6A illustrates the dicistronic unit of the pro-sequences, FIG. 6B illustrates the nucleic acid coding sequence (SEQ ID NO:19) and the amino acid sequence of the pro-sequences (SEQ ID NO:20) and FIG. 6C illustrates the assembled VB6-845-$C_L$-de-bouganin protein without the pelB sequences.

FIG. 7 illustrates the Fab anti Ep-CAM, de-bouganin construct, VB6-845-$NV_H$-de-bouganin, wherein Bou156 is linked to the N terminus of the $V_H$ domain. FIG. 7A illustrates the dicistronic units of the pro-sequences, FIG. 7B illustrates the nucleic acid coding sequence (SEQ ID NO:21) and the amino acid sequence of the pro-sequences (SEQ ID NO:22) and FIG. 7C illustrates the assembled VB6-845-$NV_H$-de-bouganin protein without the pelB sequences.

FIG. 8 illustrates the Fab anti-Ep-CAM construct VB6-845-$NV_L$-de-bouganin, wherein Bou156 is linked to the N-terminus of the $V_L$ domain. FIG. 8A illustrates the dicistronic unit of the pro-sequences, FIG. 8B illustrates the nucleic acid coding sequence (SEQ ID NO:23) and the amino acid sequence of the pro-sequences (SEQ ID NO:24) and FIG. 8C illustrates the assembled VB6-845-$NV_L$-de-bouganin protein without the pelB sequences.

Figure 9:
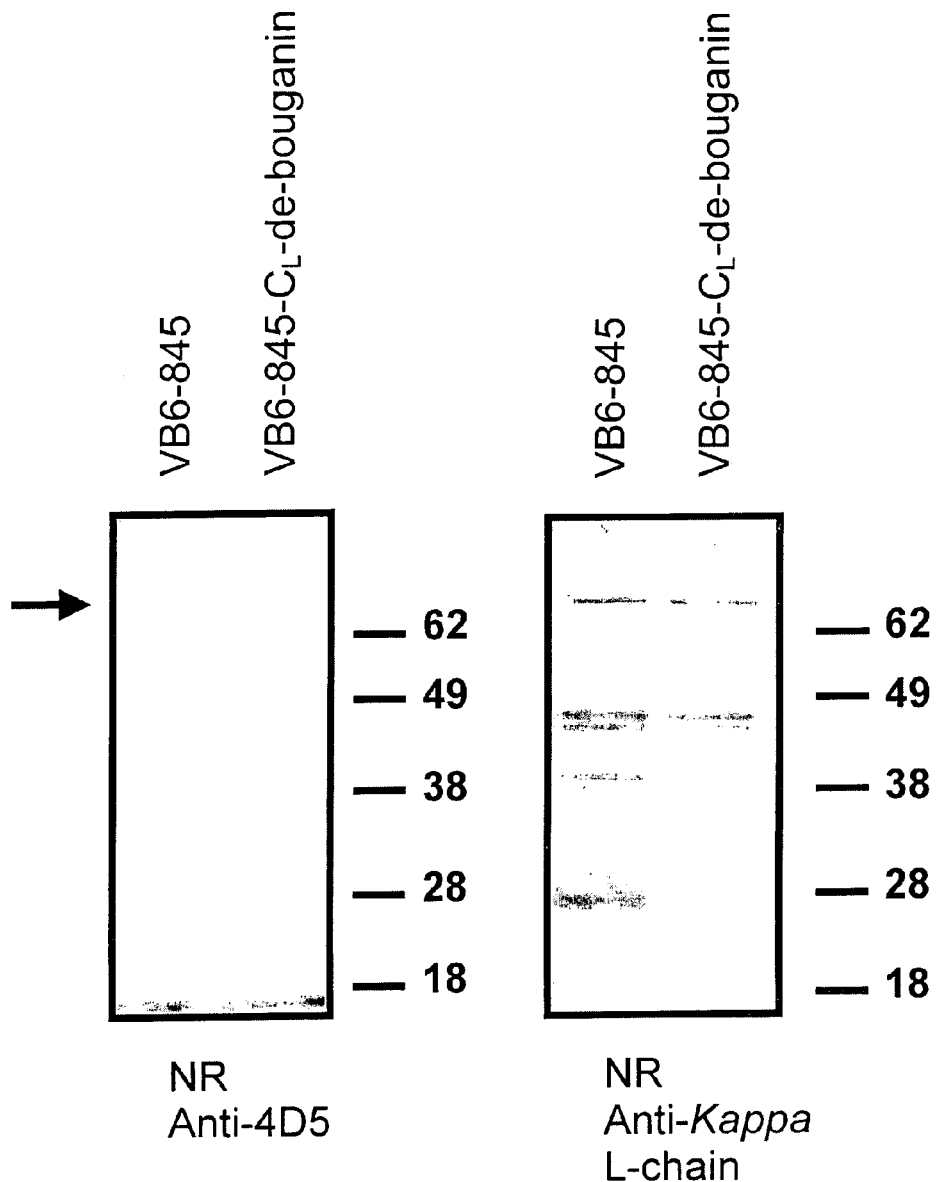
FIG. 9 is a Western Blot illustrating the expression of VB6-845 (construct of FIG. 3) and VB6-845-CL-de-bouganin (Bou156) (construct of FIG. 6) in the supernatant of induced E104 cells at lab-scale.

In one embodiment, the de-bouganin molecule is linked to the C-terminal end of the heavy or light chains. The optimal configuration comprised a pelB leader sequence adjacent to $V_H$-$C_H$ domain with an N-terminal histidine affinity tag as the first unit. Immediately following was the second unit comprising the pelB-$V_L$-$C_L$ domain linked to de-bouganin by a protease-sensitive linker. (FIG. 6) For constructs where de-bouganin was re-positioned to the N-terminal end, Western-blot analysis showed no detectable product and only C-terminal linked de-bouganin (constructs of FIGS. 3 and 6) yielded an intact soluble protein (FIG. 9), with good binding properties to Ep-CAM-positive cell lines, as illustrated in the reactivity tests detected by flow cytometry. In the Western Blot analysis, FIG. 9 illustrates the expression of VB6-845 and VB6-845 CL-de-bouganin in the supernatant of induced E104 cells at lab scale. An aliquot of the supernatant, 16 microlitres, under non-reducing conditions, was loaded on a SDS-PAGE acrylamide gel and analysed by Western Blot using either a rabbit polyclonal anti-4D5 antibody, followed by a goat anti-rabbit (1/2000), or a goat anti-human Kappa-light chain-HRP antibody (1/1000), to confirm the identity and size of the recombinant protein. The arrow indicates the full-length VB6-845 (construct of FIG. 3) and VB6-845-CL-de-bouganin (construct of FIG. 6). Western blotting of non-induced E104 culture supernatant revealed no corresponding bands demonstrating the specificity of the antibodies (not shown).

Figure 10A:
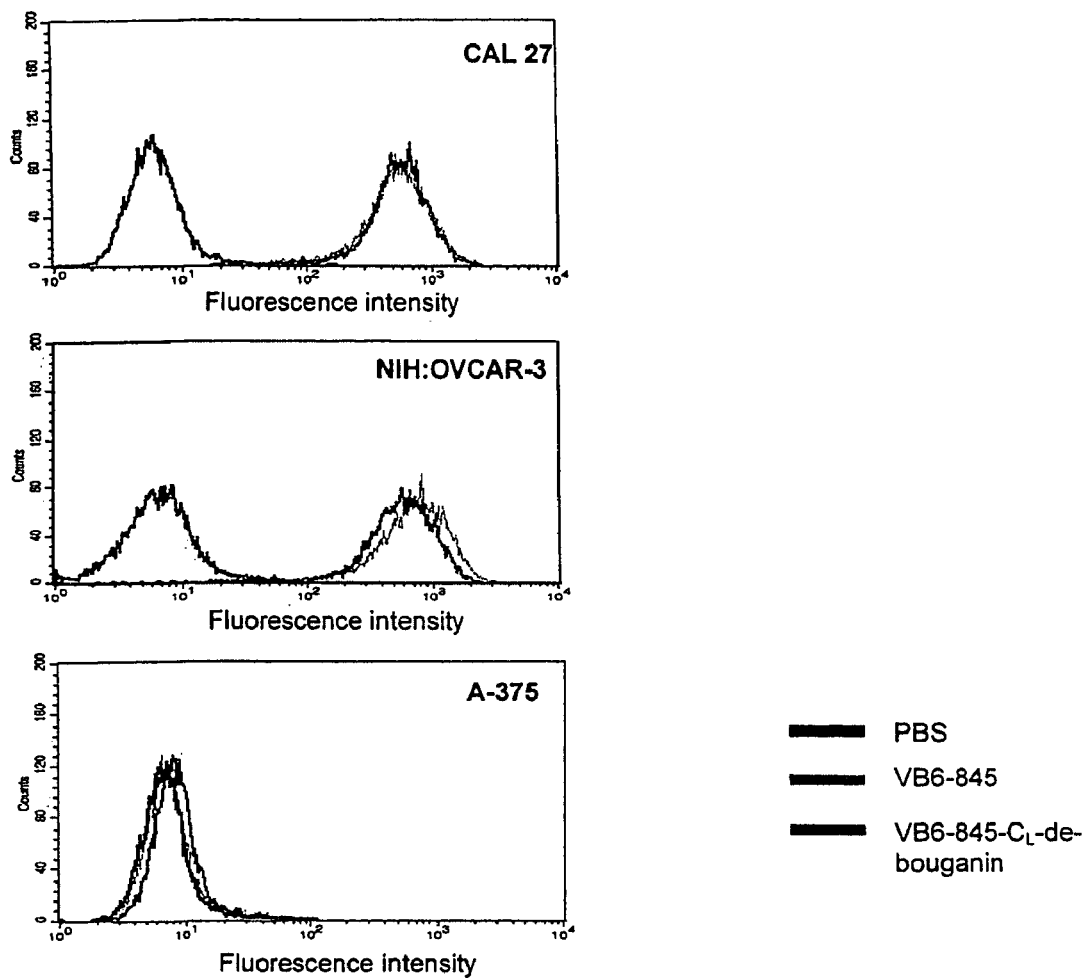
Figure 10B:
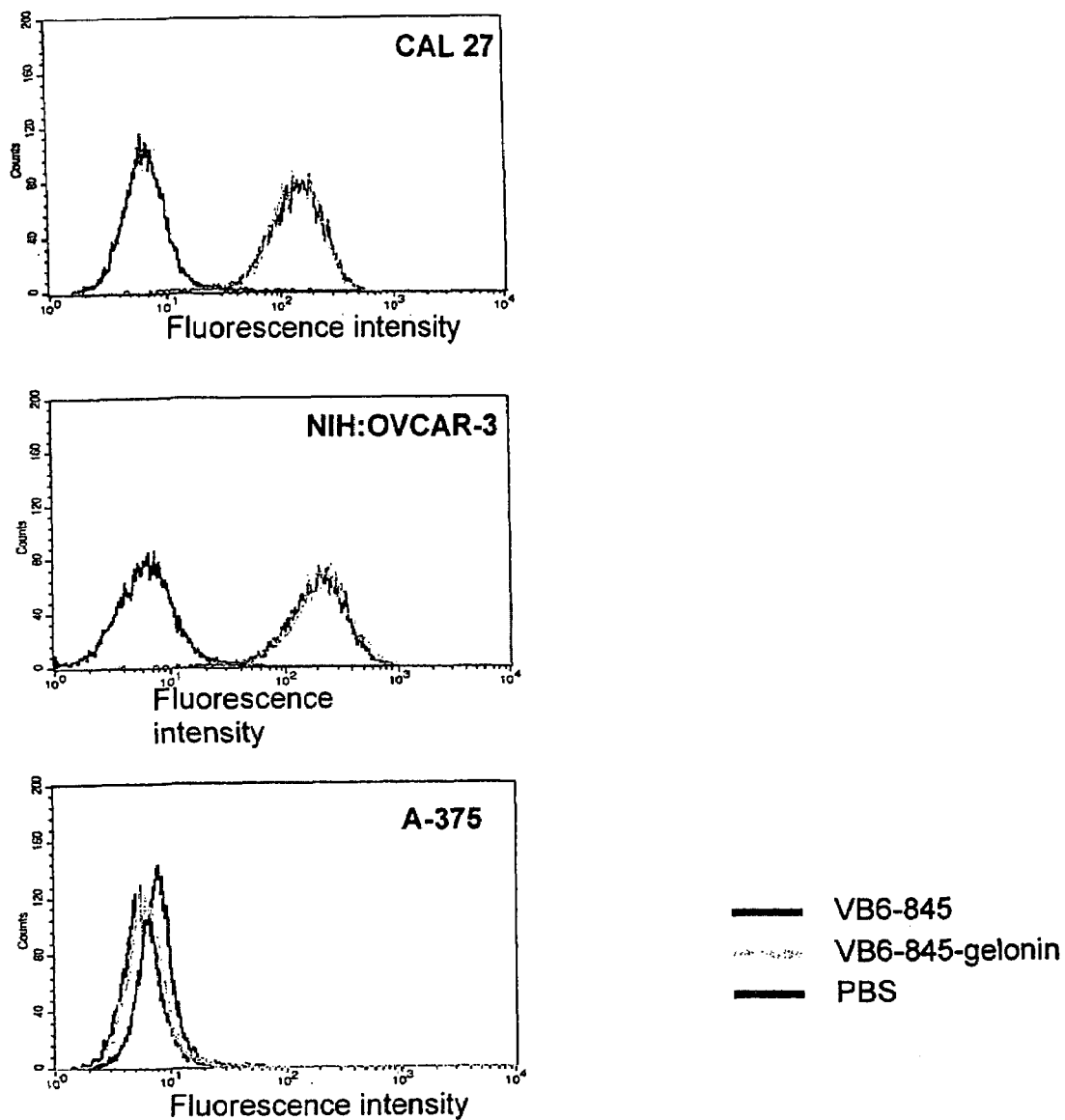
FIG. 10B, illustrates the results of the same tests conducted with VB6-845 (construct of FIG. 3) and VB6-845-gelonin (construct of FIG. 14C) and control (PBS).

The results of the reactivity tests with VB6-845 (FIG. 3) and VB6-845-CL-de-bouganin (FIG. 6) to Ep-CAM positive cell lines CAL 27 and NIH:OVCAR-3 as compared to a control (Ep-CAM-negative cell line, A-375) is illustrated in FIG. 10A. The results were comparable to the same reactivity tests conducted with another anti-Ep-CAM construct VB6-845-gelonin, wherein the de-bouganin is replaced with another plant toxin, gelonin (See FIG. 14C showing its amino acid sequence (SEQ ID NO:26) and nucleic acid sequence(SEQ ID NO:25) The results of the reactivity test with the gelonin construct are illustrated in FIG. 10B. The addition of a second de-bouganin domain in the molecule with the optimal orientation did not yield product.

The flow cytometry tests were conducted by incubating the constructs or control with $0.45 \times 10^6$ cells for an hour on ice. After washing, cell surface bound constructs were detected with a rabbit anti-bouganin (for FIG. 10A) or mouse anti-His tag (FIG. 10B) for an hour on ice. The cells were washed and incubated with FITC-conjugated sheep anti-rabbit IgG (FIG. 10A) and FITC-conjugated sheep anti-mouse (IgG) (FIG. 10B) for 30 minutes on ice. Subsequently the cells were washed, resuspended in PBS 5% FCS containing propidium iodide for assessment of antibody binding by flow cytometry. No shift in median fluorescence was detected following incubation with VB6-845 and VB6-845-CL-de-bouganin with A-375. In contrast, a marked shift in median fluorescence was observed with Ep-CAM positive cell lines, CAL 27 and NIH:OVCAR-3 (FIG. 10A). As stated above, the results with VB6-845 were similar with the gelonin construct (FIG. 10B).

Ep-CAM Specificity

A competition assay of VB6-845 (construct of FIG. 3) with Proxinium™, a scFv format of VB6-845, but containing *Pseudomonas* exotoxin A, demonstrated that the Ep-CAM specificity of VB6-845 was unaltered when engineered into a Fab format. (FIG. 11)

Figure 11:
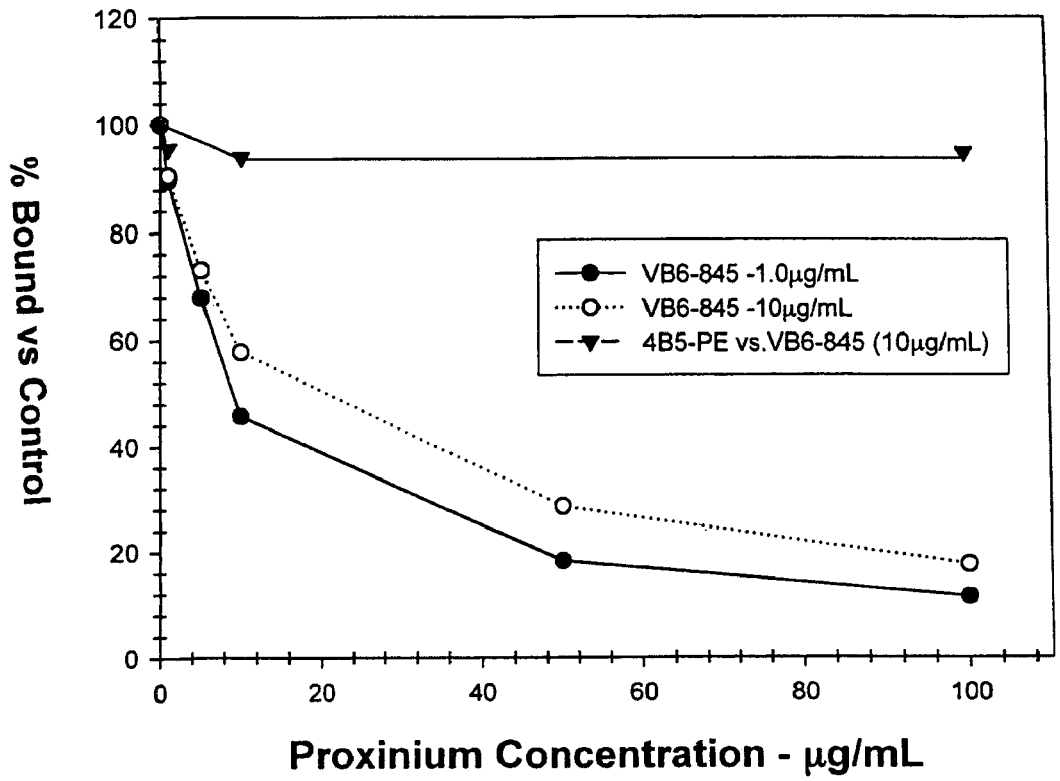
FIG. 11 is a graph illustrating the results of the competition assay-VB6-845 and Proxinium™ in NIH:OVCAR-3 cells and as described in Example 7.

FIG. 11 illustrates the flow cytometry results of the competition assay, with VB6-845 at 1 and 10 µg/mL and increased concentration of Proxinium™, ranging from 0 to 100 µg/mL, were incubated with NIH:OVCAR-3 cells (Ep-CAM positive tumour cell line). After 1 hour incubation at 4° C., cells were washed and bound VB6-845 was detected with a biotinylated rabbit anti-bouganin followed by streptavidin-cychrome. The same experiment was performed with 4B5-PE which is used as a negative control. The reaction conditions were as indicated on FIG. 11.

Potency (Biological Activity)

Figure 12:
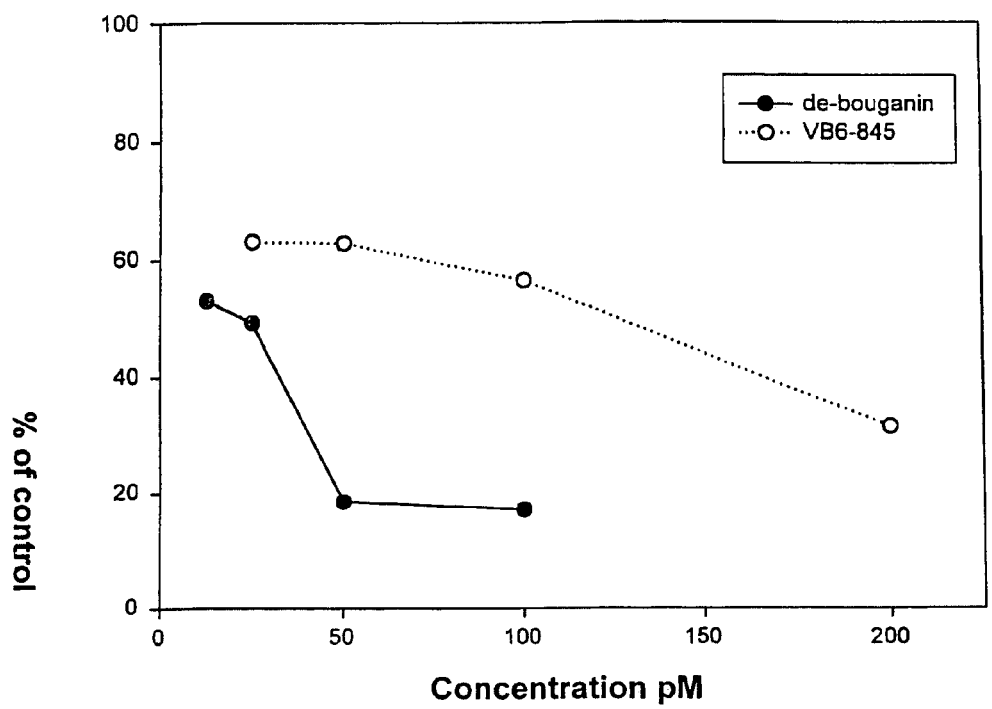
FIG. 12 is a graph illustrating the results of the cell free assay of Example 7.
Figure 13A:
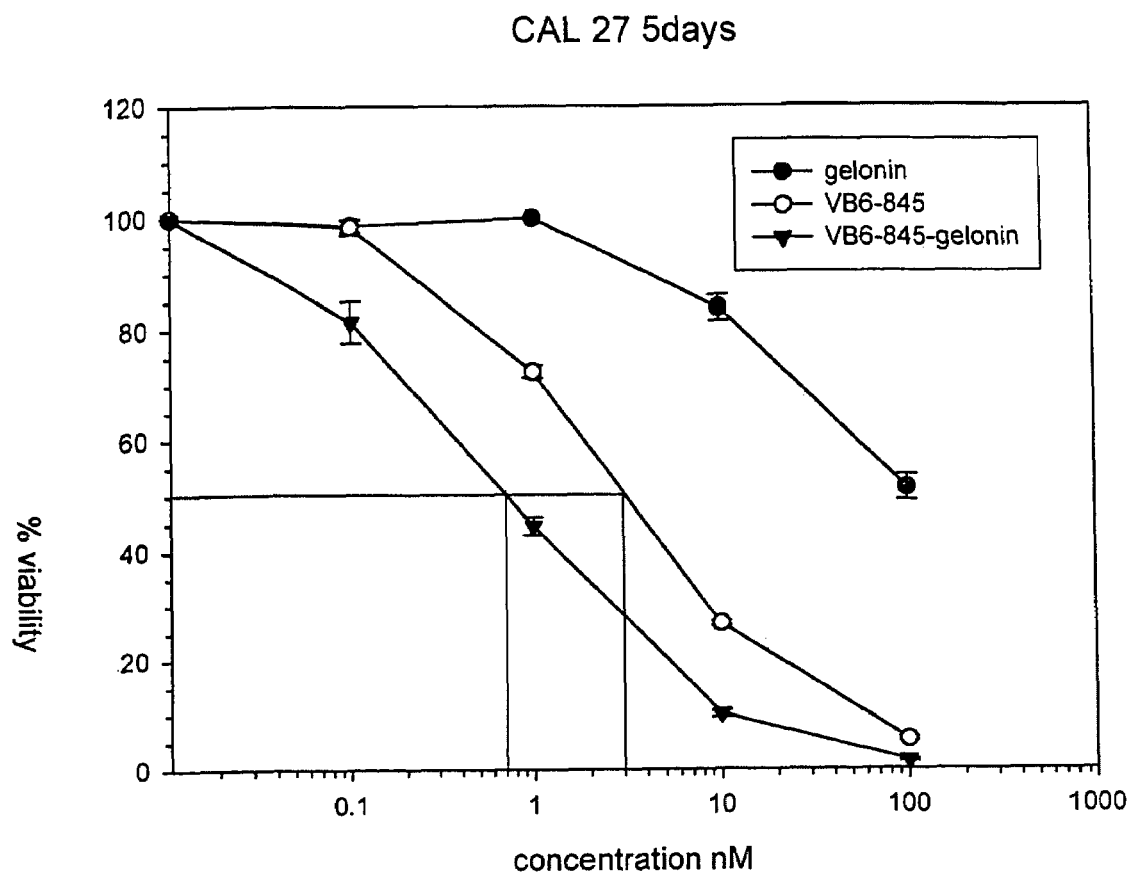
FIG. 13 illustrates the results of the MTS cytotoxicity assay of Example 8 comparing the cytoxocity of VB6-845 (construct of FIG. 3), VB6-845-CL-de-bouganin (construct of FIG. 6) and de-bouganin (Bou156) in CAL 27 (FIG. 13A) and NIH:OVCAR3 (FIG. 13B) cells.
Figure 13B:
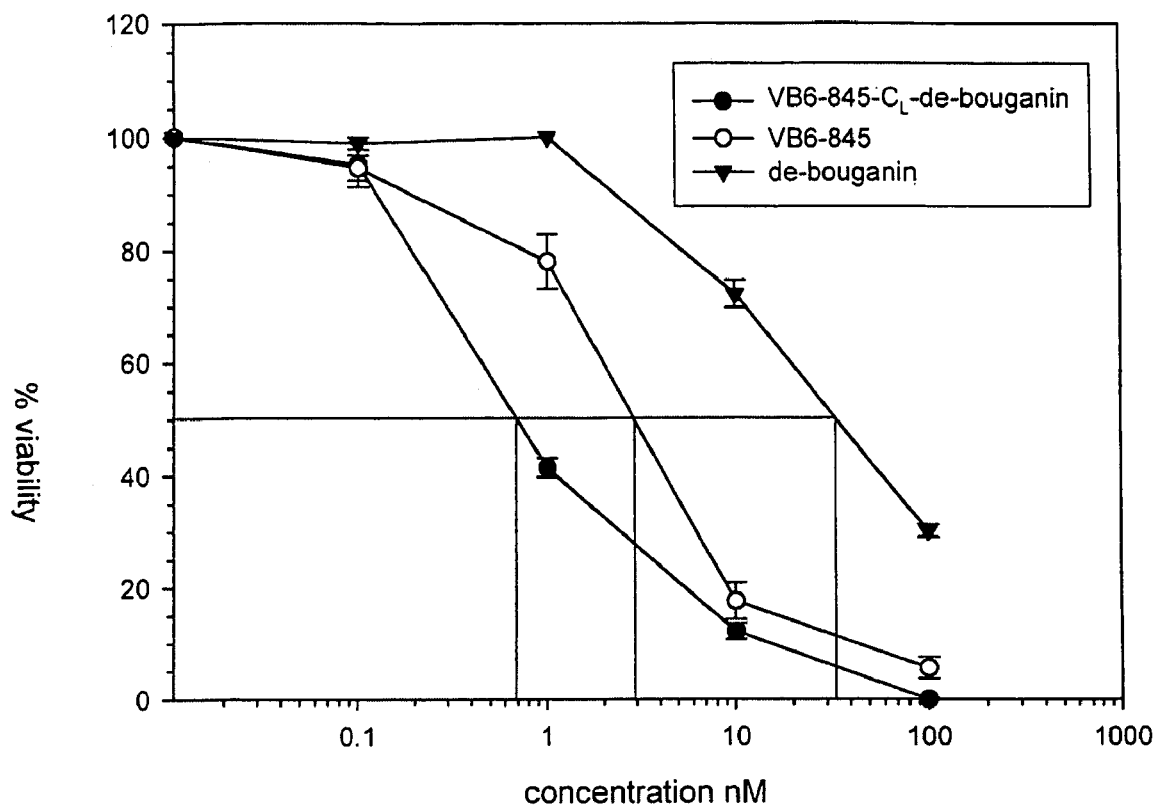

In addition, cell-free (FIG. 12) and MTS (FIG. 13 A and B) assays demonstrated that de-bouganin retained its potency when conjugated to the Fab fragment. In FIG. 12, the purified VB6-845 and de-bouganin proteins, at various concentrations, were incubated at 30° C. 90 minutes with the following mixture:

| | |
|---|---|
| Flexi Rabbit reticulocyte Lysate | 35 µL |
| Amino acid mixture, minus leucine | 1 µL |
| $^3$H-Leucine | 5 µL |
| Potassium Chloride | 1.4 µL |
| RNasin | 1 µL |
| Luciferase control RNA, 1 mg/mL | 1 µL |
| To a final volume of 50 µL | |

After the translation reaction is completed a sample of 2 µL is taken, mixed with 98 µL of 1M NaOH/2% $H_2O_2$ and incubated at 37° C. for 10 minutes. The translated protein is precipitated with the addition of ice-cold 25% TCA/2% casamino acids and incubated on ice for 30 minutes. The precipitate is then collected on a Whatman GF/C glass fiber filter (pre-wet with 5% cold TCA) by centrifugation at 8000 rpm 5 minutes. The filter is rinsed 3 times with ice-cold 5% TCA and once with acetone. After the filter is dry, scintillation mixture is added and the counts are determined in a liquid scintillation counter. The MTS assay used to measure potency was conducted using standard technique known in the art, and as more fully described below in Example 8. Using the Ep-CAN-positive cell lines, CAL 27 and NIH: OVCAR-3, the $IC_{50}$ of VB6-845 was 3 to 4 nM and 2 to 3 nN, respectively. In the case of VB6-845-$C_L$-de-bouganin, the potency was measured at 1 to 2 nN for CAL 27 and 0.6 to 0.7 nM versus NIH:OVCAR-3. The development of Fab anti-Ep-CAM construct, comprising a human tumor targeting antibody fragment linked to a de-immunized bouganin should permit repeat systemic administration of this drug and hence yield greater clinical benefit.

Harvesting of the Constructs

The constructs can be isolated from the cell cultures by techniques known in the art. For instance, if a His tag is placed at the N-terminal of the peptide construct, the Fab-bouganin protein can be purified using a $Ni^{2+}$-chelating capture method. As an example the following protocol can be used.

Conducting fed batch fermentation of VB6-845 variants performed in a 15 L CHEMAP fermenter using TB medium. At an $OD_{600}$ of 20 (mid-log), the culture is induced with a mixture of feed and inducer containing 50% glycerol and 200 g/l L-arabinose. At 30 hours post induction, the culture is harvested, centrifuged at 8000 rpm for 30 min and VB6-845 variants purified using CM sepharose and Metal-Charged Chelating sepharose columns followed by a size exclusion column. Briefly, the supernatant is concentrated and diafiltered against 20 mM sodium phosphate pH 6.9±0.1. The diafiltered concentrated supernatant is then applied onto a CM sepharose column equilibrated with 20 mM sodium phosphate, 25 mM NaCl pH 6.9±0.1. The column is washed with 20 mM sodium phosphate, 25 mM NaCl pH 6.9±0.1, bound VB6-845 is subsequently eluted with 20 mM sodium phosphate, 150 mM NaCl pH 7.5±0.1. The CM sepharose eluate is adjusted to contain a final concentration of 0.25% Triton-X100 and applied to a charged chelating sepharose column. The chelating sepharose column is then washed with 3 different wash buffers starting with 20 mM sodium phosphate, 150 mM NaCl, 0.25% triton-X100 pH 7.5±0.1 followed by 20 mM sodium phosphate, 150 mM NaCl pH 7.5±0.1 and followed by 20 mM sodium phosphate, 150 mM NaCl, 10 mM imidazole pH 7.5±0.1. The bound VB6-845 is then eluted with 20 mM sodium phosphate, 150 mM NaCl, 250 mM imidazole pH 7.5±0.1 and collected in 2 mL fractions. The absorbance at $A_{280}$ is determined for each fraction and the fractions with material pooled are applied onto a size exclusion column S200 in order to obtain a purity of >80%. In one embodiment, to increase the protein purity and remove endotoxin, the pooled SEC fraction is diluted 5-fold with 20 mM $NaPO_4$, pH 7.5 and passed though a Q-sepharose 15 ml fast flow column equilibrated with 20 mM $NaPO_4$, 25 mM NaCl pH 7.5 at a flow rate of about 5 ml/min. After application of the sample through the column, the column is washed with 10 CV of equilibration buffer and the wash is pooled with the initial Q-sepharose flow through. The effluent is concentrated to ~10-fold through the use of a 30 kDa MWCO membrane (Sartorius hydrosart membrane] to achieve a final concentration of 7.5 mg/ml. Tween-80 is then added to a final concentration of 0.1%. The final product is sterile filtered and stored at −80° C. Samples at each steps of the process are analyzed by Western blot after immunoblotting with the anti-4D5 antibody. Purity is confirmed by colloidal blue staining. The level of expression of VB6-845 variants is determined by Western Blot analysis and ELISA.

Example 8

Functional and Biological Characterization of VB6-845, a Recombinant Ep-CAM-specific Fab Antibody Genetically-linked with De-immunized Bouganin (De-douganin)

Chemotherapeutics are highly cytotoxic agents that often represent the standard of care in the treatment of many of the solid tumor cancers. The cytotoxic action of these drugs targets rapidly dividing cells, both normal and tumor, thus creating a variety of adverse clinical side-effects. VB6-845 is a Fab antibody linked to a de-immunized form of the plant-derived toxin bouganin. Unlike chemotherapeutics which lack defined tumor-target specificity, VB6-845 restricts its cytolytic effect to Ep-CAM-positive tumor targets alone. In this study, flow cytometry analysis and cytotoxicity were measured to assess the potency and selectivity of VB6-845.

Flow Cytometry

The tumour cell lines used in this study were purchase from ATCC and were propagated following ATCC's recommendations except for the cell lines C-41, TOV-112D which were grown in RPMI 1640 or DMEM supplemented with 10% FCS, respectively. Tumor cells were harvested at 60-70% confluence with viability over 90%. The human normal mammary epithelial cells (HMEC) were purchased from CAMBREX and maintained in specified media according to the procedure provided by CAMBREX. The cells were harvested at 70% confluence with viability over 90%.

The gynaecological cell lines from endometrial ovarian and cervical cancer indications were tested for VB6-845 binding on flow cytometry (Table 9). Ten microgram/mL of VB6-845 was added to each cell line ($3 \times 10^5$ cells) and incubated for 2 h at 4° C. A-375 and CAL 27 were used as negative and positive cell line controls, respectively. After washing off the unbound material, a mouse monoclonal anti-Histidine antibody (Amersham Pharmacia, Cat # 27471001) diluted 1/800 in PBS containing 10% FCS was added and incubated for a further 1 hr at 4° C. Subsequently, FITC-labeled anti-mouse IgG (The Binding Site, Cat# AF271) diluted 1/100 in PBS-10% FCS was added and incubated for 30 min. at 4° C. Finally, the cells were analyzed on a FACS Calibur following propidium iodide staining to gate out the dead cells.

Cytotoxicity

Figure 14A:
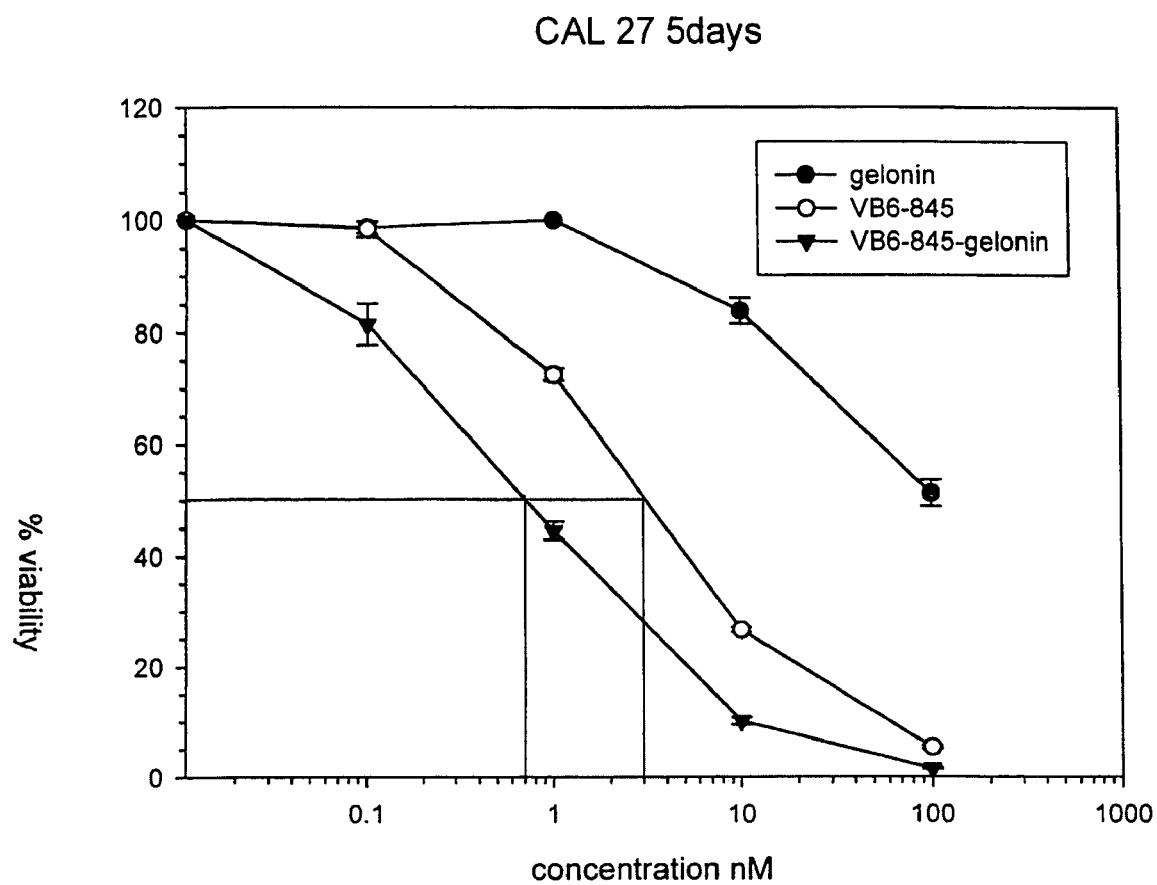
FIGS. 14A and B illustrate the results of the MTS cytotoxicity assay of Example 8 comparing the cytoxocity of VB6-845 (construct of FIG. 3), VB6-845-gelonin (construct of FIG. 14C) and gelonin in CAL 27 (FIG. 14A) and NIH:OVCAR3 (FIG. 14B) cells.
Figure 14B:
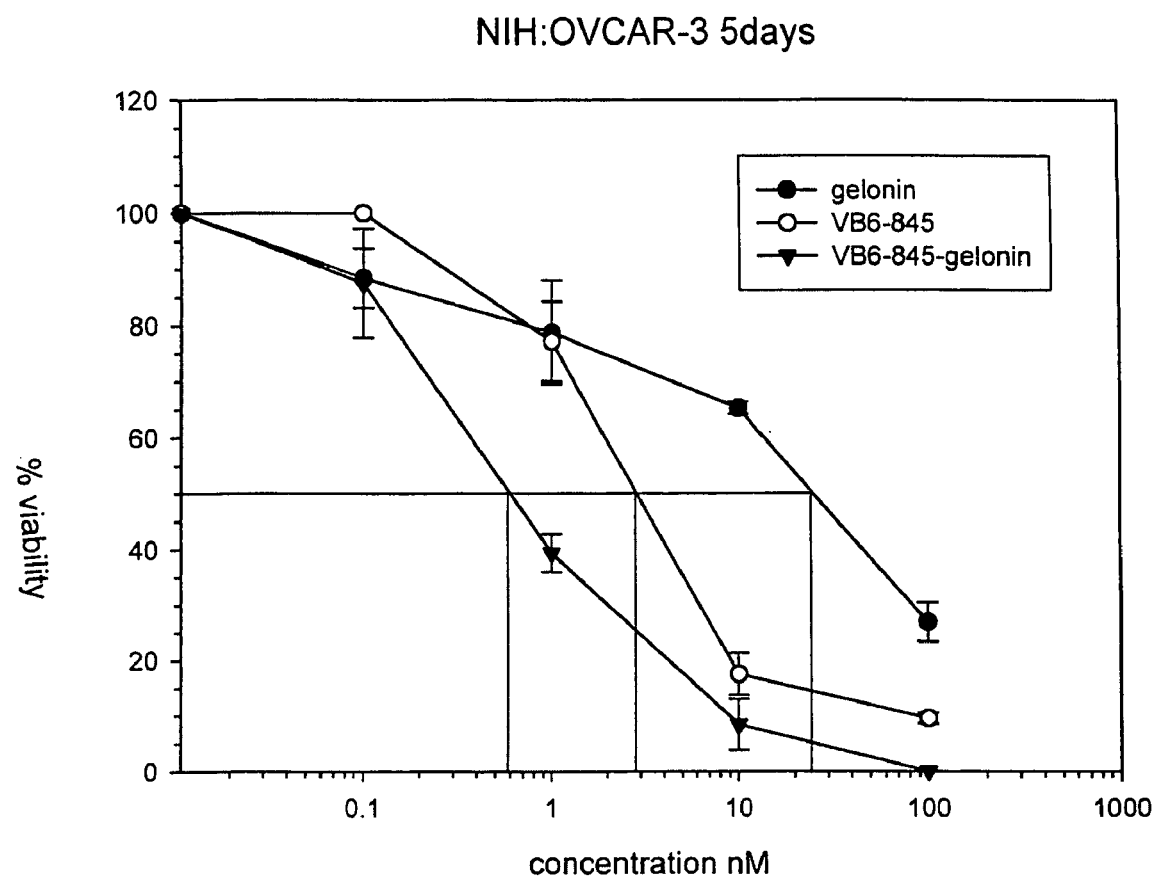
FIG. 14C illustrates the nucleic acid coding sequence (SEQ ID NO:25) and the amino acid sequence (SEQ ID NO:26) of the VB6-845-gelonin construct.

The level of killing for VB6-845 in the cells listed in the flow cytometry study is as indicated in Table 10, indicated that the construct retained its de-bouganin cytotoxicity activity against Ep-CAM-positive cell lines. The cytotoxicity was comparable to another Fab VB6-845 variant containing a different plant-derived toxin, gelonin. (FIG. 14) FIG. 14A compares the cytotoxicity of gelonin, Fab anti-Ep-CAM-gelonin construct (VB6-845-Gelonin) and the Fab anti-Ep-CAM-de-bouganin (Bou156) construct (VB6-845) in CAL 27 (FIG. 14A) and NIH:OVCAR-3 cells (FIG. 14B). The nucleic acid and amino acid sequence of the VB6-845-gelonin construct is illustrate in FIG. 14C.

To study the specificity and selectivity of VB6-845 (Construct of FIG. 3), the cytotoxic activity of VB6-845 (90% pure) was tested against Ep-CAM-positive (NIH:OVCAR-3) and Ep-CAM-negative (HMEC, DAUDI, A-375) cell lines (Table 11) along with 17 chemotherapeutic drugs (LKB Laboratories Inc.).

The MTS assay was preformed using standard techniques known in the art. More particularly, 50 microlitres of cells ($2 \times 10^4$ cells/ml) were seeded per well and plates were incubated at 37° C. under 5% $CO_2$ for 2 hr. Then 50 microlitres of spiked drug (i.e. construct to be tested or control) was added to the culture medium at increasing concentrations. Culture medium, with or without cells, was used as positive and negative controls, respectively. The plates were left at 37° C. under 5% $CO_2$ for 5 days. At day 5, the inhibition of cell proliferation was evaluated by adding 20 microlitres of MTS reagent (Promega, Cat# G5430). The plates were further incubated at 37° C. under 5% $CO_2$ for 2 hr and ODs were read at 490 nm using the plate reader spetrophotometer. Background values were subtracted from the sample values obtained for each concentration and the results were expressed as a percent of viable cells. The $IC_{50}$ values for each drug were calculated for each cell line.

When assayed for cytotoxicity against NIH:OVCAR-3, an Ep-CAM-positive ovarian carcinoma, using a panel of standard chemotherapeutic agents, VB6-845 was shown to be more potent than 12 of the 17 drugs tested. (Table 11) Though 5 chemotherapeutics were more cytotoxic, they were also shown to be far more toxic in that they lacked any cell-specific killing. Of the five recommended chemotherapeutic agents for the treatment of ovarian cancer (Paclitaxel, Carboplatin, Cisplatin, Doxorubicin and Topotecan), only two (Paclitaxel and Topotecan) were more cytotoxic. While VB6-845 demonstrated highly potent cytolytic activity in the range of of 1 to 2 nM, the potent killing was restricted exclusively to the Ep-CAM-positive tumor cell line NIH:OVCAR-3. Although some killing of Ep-CAM-negative cell lines was exhibited with VB6-845, the cytotoxic effect was at least 220-fold and at most >1000-fold less toxic. VB6-845 thus represents a potent antibody-directed treatment alternative to chemotherapeutics that when combined with the lower toxicity profile, holds much promise in the treatment of many different types of solid tumors.

Example 9

VB6-011: Recombinant Engineering of a Tumor-associated Antigen-specific Fab Antibody for Optimal Delivery of De-immunized Bouganin (De-bouganin)

Tumor-targeting cytotoxins are composed of the variable region of an antibody linked to a bacterial, fungal or plant toxin. The present study illustrates that the deimmunized bouganin constructs of the invention, comprising deimmunized bouganin linked to a targeting moiety have reduced immunogenicity, while still retaining their biological activity. TABLE 13 demonstrates the binding of the tumor-associated antigen antibody to several types of tumours and thus shows that it can be used to treat these types of cancers.

De-immunized Bouganin Construct: Tumor-associated Antigen Directed Targeting Moiety Linked to De-bouganin The H11 antibody, a monoclonal antibody recognizing tumor-associated antigen, was genetically linked to a de-immunized form of bouganin (de-bouganin), Bou156, a potent, plant-derived, type I ribosome-inactivating protein (RIP), to create the antibody-toxin construct VB6-011. FIG. 15 illustrates the nucleic acid coding sequence and amino acid sequence. Testing of this construct, illustrates that the construct retained its biological activity (cytoxicity).

Potency (Biological Activity)

Figure 16:
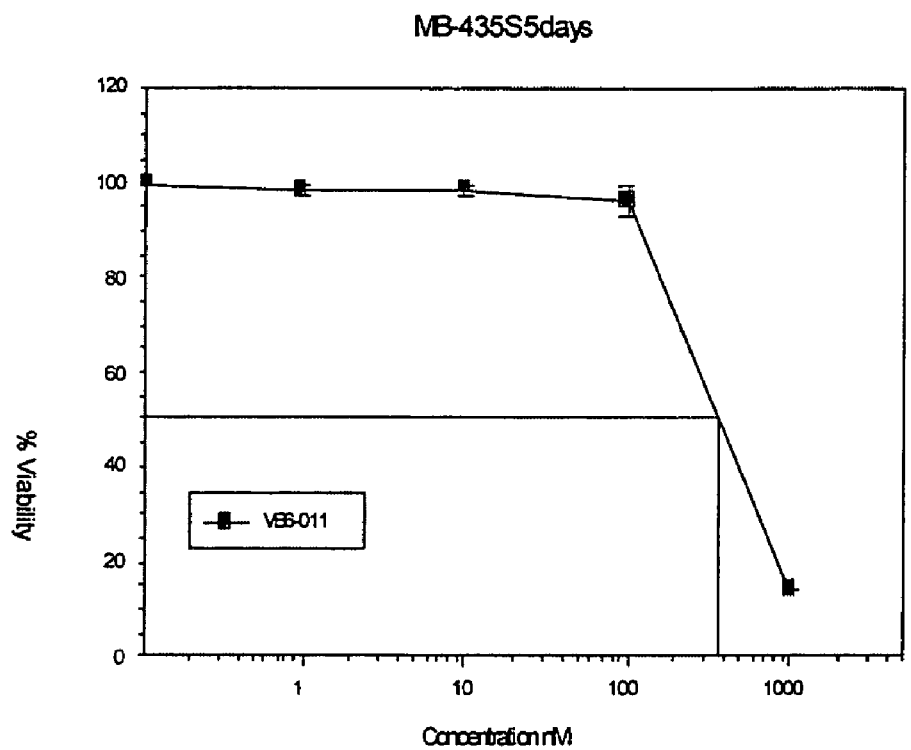
FIG. 16 illustrates the results of the MTS cytotoxicity assay of Example 9 showing the cytotoxicity of VB6-011 in MB-435S cells.

MTS assay demonstrated that de-bouganin retained its potency when conjugated to the Fab fragment (FIG. 16). The MTS assay used to measure potency was conducted using standard technique known in the art, and as more fully described in Example 8.

Cytotoxicity

To study the specificity and selectivity of VB6-011, the cytotoxic activity was tested against MB-435S cells. The MTS assay was performed using standard techniques known in the art. More particularly, 50 microlitres of cells ($2\times10^4$ cells/ml) were seeded per well and plates were incubated at 37° C. under 5% $CO_2$ for 2 hr. Then 50 microlitres of spiked drug (i.e. construct to be tested or control) was added to the culture medium at increasing concentrations. Culture medium, with or without cells, was used as positive and negative controls, respectively. The plates were left at 37° C. under 5% $CO_2$ for 5 days. At day 5, the inhibition of cell proliferation was evaluated by adding 20 microlitres of MTS reagent (Promega, Cat# G5430). The plates were further incubated at 37° C. under 5% $CO_2$ for 2 hr and ODs were read at 490 nm using the plate reader spectrophotometer. Background values were subtracted from the sample values obtained for each concentration and the results were expressed as a percent of viable cells. Results show that the IC50 value of VB6-011 is 350 nM.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Peptide # | Position of first amino acid | SEQ ID NO | Sequence | Peptide # | Position of first amino acid | SEQ ID NO | Sequence |
|---|---|---|---|---|---|---|---|
| 1 | 1 | 32 | YNTVSFNLGEAYEYP | 46 | 136 | 77 | EFSIEAIHGKTINGQ |
| 2 | 4 | 33 | VSFNLGEAYEYPTFI | 47 | 139 | 78 | IEAIHGKTINGQEIA |
| 3 | 7 | 34 | NLGEAYEYPTFIQDL | 48 | 142 | 79 | IHGKTINGQEIAKFF |
| 4 | 10 | 35 | EAYEYPTFIQDLRNE | 49 | 145 | 80 | KTINGQEIAKFFLIV |
| 5 | 13 | 36 | EYPTFIQDLRNELAK | 50 | 148 | 81 | NGQEIAKFFLIVIQM |
| 6 | 16 | 37 | TFIQDLRNELAKGTP | 51 | 151 | 82 | EIAKFFLIVIQMVSE |
| 7 | 19 | 38 | QDLRNELAKGTFVCQ | 52 | 154 | 83 | KFFLIVIQMVSEAAR |
| 8 | 22 | 39 | RNELAKGTPVCQLPV | 53 | 157 | 84 | LIVIQMVSEAARFKY |
| 9 | 25 | 40 | LAKGTPVCQLPVTLQ | 54 | 160 | 85 | IQMVSEAARFKYIET |
| 10 | 28 | 41 | GTPVCQLPVTLQTIA | 55 | 163 | 86 | VSEAARFKYIETEVV |
| 11 | 31 | 42 | VCQLPVTLQTIADDK | 56 | 166 | 87 | AARFKYIETEVVDRG |
| 12 | 34 | 43 | LPVTLQTIADDKRFV | 57 | 169 | 88 | FKYIETEVVDRGLYG |
| 13 | 37 | 44 | TLQTIADDKRFVLVD | 58 | 172 | 89 | IETEVVDRGLYGSFK |
| 14 | 40 | 45 | TIADDKRFVLVDITT | 59 | 175 | 90 | EVVDRGLYGSFKPNF |
| 15 | 43 | 46 | DDKRFVLVDITTTSK | 60 | 178 | 91 | DRGLYGSWKPNFKVL |
| 16 | 46 | 47 | RFVLVDITTTSKKTV | 61 | 181 | 92 | LYGSFKPNFKVLNLE |
| 17 | 49 | 48 | LVDITTTSKKTVKVA | 62 | 184 | 93 | SFKPNFKVLNLENNW |
| 18 | 52 | 49 | ITTTSKKTVKVAIDV | 63 | 187 | 94 | PNFKVLNLENNWGDI |
| 19 | 55 | 50 | TSKKTVKVAIDVTDV | 64 | 190 | 95 | KVLNLENNWGDISDA |
| 20 | 58 | 51 | KTVKVAIDVTDVYVV | 65 | 193 | 96 | NLENNWGDISDAIHK |
| 21 | 61 | 52 | KVAIDVTDVYVVGYQ | 66 | 196 | 97 | NNWGDISDAIHKSSP |
| 22 | 64 | 53 | IDVTDVYVVGYQDKW | 67 | 199 | 98 | GDISDAIHKSSPQCT |
| 23 | 67 | 54 | TDVYVVGYQDKWDGK | 68 | 202 | 99 | SDAIHKSSPQCTTIN |
| 24 | 70 | 55 | YVVGYQDKWDGKDRA | 69 | 205 | 100 | IHKSSPQCTTINPAL |
| 25 | 73 | 56 | GYQDKWDGKDRAVFL | 70 | 208 | 101 | SSPQCTTINPALQLI |
| 26 | 76 | 57 | DKWDGKDRAVFLDKV | 71 | 211 | 102 | QCTTINPALQLISPS |
| 27 | 79 | 58 | DGKDRAVFLDKVPTV | 72 | 214 | 103 | TINPALQLISPSNDP |
| 28 | 82 | 59 | DRAVFLDKVPTVATS | 73 | 217 | 104 | PALQLISPSNDPWVV |

TABLE 1-continued

| Peptide # | Position of first amino acid | SEQ ID NO | Sequence | Peptide # | Position of first amino acid | SEQ ID NO | Sequence |
|---|---|---|---|---|---|---|---|
| 29 | 85 | 60 | VFLDKVPTVATSKLF | 74 | 220 | 105 | QLISPSNDPWVVNKV |
| 30 | 88 | 61 | DKVPTVATSKLFPGV | 75 | 223 | 106 | SPSNDPWVVNKVSQI |
| 31 | 91 | 62 | PTVATSKLFPGVTNR | 76 | 226 | 107 | NDPWVVNKVSQISPD |
| 32 | 94 | 63 | ATSKLFPGVTNRVTL | 77 | 229 | 108 | WVVNKVSQISPDMGI |
| 33 | 97 | 64 | KLFPGVTNRVTLTFD | 78 | 232 | 109 | NKVSQISPDMGILKF |
| 34 | 100 | 65 | PGVTNRVTLTFDGSY | 79 | 235 | 110 | SQISPDMGILKFKSS |
| 35 | 103 | 66 | TNRVTLTFDGSYQKL | 80 | 238 | 111 | SPDMGILKFKSSKLT |
| 36 | 106 | 67 | VTLTFDGSYQKLVNA | 81 | 240 | 112 | MGILKFKSSKLTQFA |
| 37 | 109 | 68 | TFDGSYQKLVNAAKV | 82 | 243 | 113 | LKFKSSKLTQFATMI |
| 38 | 112 | 69 | GSYQKLVNAAKVDRK | 83 | 246 | 114 | KSSKLTQFATMIRSA |
| 39 | 115 | 70 | QKLVNAAKVDRKDLE | 84 | 249 | 115 | KLTQFATMIRSAIVE |
| 40 | 118 | 71 | VNAAKVDRKDLELGV | 85 | 252 | 116 | QFATMIRSAIVEDLD |
| 41 | 121 | 72 | AKVDRKDLELGVYKL | 86 | 255 | 117 | TMIRSAIVEDLDGDE |
| 42 | 124 | 73 | DRKDLELGVYKLEFS | 87 | 258 | 118 | RSAIVEDLDGDELEI |
| 43 | 127 | 74 | DLELGVYKLEFSIEA | 88 | 261 | 119 | IVEDLDGDELEILEP |
| 44 | 130 | 75 | LGVYKLEFSIEAIHG | 89 | 264 | 120 | DLDGDELEILEPNIA |
| 45 | 133 | 76 | YKLEFSIEAIHGKTI | | | | |

Bouganin sequence peptides. The underlined residues are not present in the mature protein

TABLE 2

| Donor No | Donor storage code | Allotype |
|---|---|---|
| 1 | BC63 | DRB1*04, DRB1*07, DRB4*01 |
| 2 | BC86 | DRB1*04, DRB1*15, DRB5 |
| 3 | BC90 | DRB1*07, DRB1*15, DRB4*01, DRB5 |
| 4 | BC134 | DRB1*01, DRB1*03, DRB3 |
| 5 | BC167 | DRB1*01, DRB1*07 and DRB4*01 |
| 6 | BC216 | DRB1*14, DRB1*15, DRB3, DRB5 |
| 7 | BC217 | DRB1*04, DRB1*12, DRB3, DRB4*01 |
| 8 | BC233 | DRB1*04, DRB1*11 and DRB3, DRB4*01 |
| 9 | BC241 | DRB1*07, DRB1*11, DRB3, DRB4*01 |
| 10 | BC246 | DRB1*01, DRB1*13 and DRB3 |
| 11 | BC262 | DRB1*03, DRB1*07, DRB3, DRB4*01 |
| 12 | BC292 | DRB1*07, DRB1*13, DRB3, DRB4*01 |
| 13 | BC293 | DRB1*04, DRB1*10, DRB4*01 |
| 14 | BC231 | DRB1*03 or DRB1*03, DRB1*13 and DRB3 |
| 15 | BC301 | DRB1*07, DRB1*14, DRB3 |
| 16 | BC326 | DRB1*03, DRB1*15, DRB3, DRB5 |
| 17 | BC316 | DRB1*13, DRB1*15, DRB3, DRB5 |
| 18 | BC321 | DRB1*01, DRB1*15, DRB5 |
| 19 | BC382 | DRB1*04, DRB1*08, DRB4*01 |
| 20 | BC336 | DRB1*01, DRB1*11, DRB3 |

MHC Allotypes of PBMC donors

TABLE 3

| Primer | SEQ ID NO | Sequence |
|---|---|---|
| OL1032 | 121 | CATTACAAACGTCTACCAAGTTT |
| OL1033 | 122 | TTACAAAAGTAGATAAGTAATGTG |
| OL1322 | 123 | GATATACATATGAAATACCTATTGCCTACG |
| OL1067 | 124 | TGACACAGTGTTGTACGCTGGTTGGGCAGCGAGTAA |
| OL1068 | 125 | GCTGCCCAACCAGCGTACAACACTGTGTCATTTAAC |
| OL1323 | 126 | CGAGTGCGGCCGCTCAATGGTGATGGTGATGGTGT |

Sequences of primers used in the construction of the WT bouganin gene

TABLE 4

Single substitution bouganin variants constructed and tested.

| Mutation | Nucleotide Mutations | Activity in luciferase assay* | Clone ID** |
|---|---|---|---|
| Negative control | | | |
| Y70A | TAT - GCT | -- | BouY70A |
| Epitope Region R1 (peptide 41) | | | |
| V123T | GTG - ACG | +/- | Bou2 |

TABLE 4-continued

Single substitution bouganin variants constructed and tested.

| Mutation | Nucleotide Mutations | Activity in luciferase assay* | Clone ID** |
|---|---|---|---|
| V123A | GTG - GCT | ++ | Bou3 |
| V123D | GTG - GAT | -- | — |
| V123E | GTG - GAA | -- | — |
| V123G | GTG - GGC | -- | — |
| V123H | GTG - CAC | -- | — |
| V123K | GTG - AAG | -- | — |
| V123N | GTG - AAC | -- | — |
| V123P | GTG - CCT | -- | — |
| V123Q | GTG - CAA | ++ | Bou4 |
| V123R | GTG - AGA | -- | — |
| V123S | GTG - TCA | -- | — |
| D127G | GAT - GGC | ++ | Bou5 |
| D127A | GAT - GCT | ++ | Bou6 |
| E129K | GAA - AAG | -- | — |
| E129R | GAA - AGA | -- | — |
| E129Q | GAA - CAA | +/- | Bou7 |
| E129G | GAA - GGC | ++ | Bou8 |
| Epitope Region R2 (peptide 44) | | | |
| Y133P | TAC - CCC | -- | — |
| Y133N | TAC - AAC | ++ | Bou9 |
| Y133T | TAC - ACA | ++ | Bou10 |
| Y133A | TAC - GCT | ++ | Bou11 |
| Y133R | TAC - AGA | ++ | Bou12 |
| Y133D | TAC - GAT | ++ | Bou13 |
| Y133E | TAC - GAA | +/- | Bou14 |
| Y133Q | TAC - CAA | ++ | Bou15 |
| Y133G | TAC - GGC | ++ | Bou16 |
| Y133H | TAC - CAC | ++ | Bou17 |
| Y133K | TAC - AAG | ++ | Bou18 |
| Y133S | TAC - TCA | ++ | Bou19 |
| Epitope Region R3 (peptide 50) | | | |
| E151T | GAGATA - ACGGAA | -- | — |
| I152E | | | |
| I152Q | ATA - CAA | ++ | Bou20 |
| I152A | ATA - GCA | ++ | Bou21 |
| I152E | ATA - GAA | -- | — |
| F155P | TTC - CCA | -- | — |
| F155H | TTC - CAC | -- | — |
| I158P | ATT - CCA | -- | — |

*Activity in Luciferase assay:
++ = same or higher than WT protein.
+ = within 2-fold of WT activity.
+/- = within 3-fold of WT activity.
-- = less than one-third of WT activity.
WT = Wild-type protein.
**Clone ID. Designations for functionally active variants only.

TABLE 5

Multiple substitution bouganin variants constructed and tested.

| Clone ID | Epitope Region R1 (peptide 41) | Epitope Region R2 (peptide 44) | Epitope Region R3 (peptide 51) | Activity in luciferase assay |
|---|---|---|---|---|
| Bou143 | V123Q | Y133Q | I152Q | ++ |
| Bou144 | V123A | Y133N | I152A | ++ |
| Bou145 | V123A | Y133Q | I152A | ++ |
| Bou146 | V123A | D127G | | ++ |
| Bou147 | V123A | D127A | | ++ |
| Bou148 | V123Q | D127G | | ++ |
| Bou149 | V123Q | D127A | | ++ |
| Bou150 | V123Q | E129G | | + |
| Bou151 | V123A | E129G | | + |
| Bou156 | V123A | D127A | Y133N | I152A | ++ |
| Bou157 | V123A | D127A | Y133Q | I152A | ++ |

*Activity in Luciferase assay:
++ = same or higher than WT protein.
+ = within 2-fold of WT activity.
+/- = within 3-fold of WT activity.
-- = less than one-third of WT activity.
WT = Wild-type protein.

TABLE 6

| Clone ID | Substitution(s)* | Protein |
|---|---|---|
| Bou32 | WT | SEQ ID No 1 |
| Bou156 | V123A, D127A, Y133N, I152A | SEQ ID No 13 |
| Bou157 | V123A, D127A, Y133Q, I152A | SEQ ID No 14 |
| Bou143 | V123Q, Y133Q, I152Q | SEQ ID No 150 |
| Bou144 | V123A, Y133N, I152A | SEQ ID No 151 |
| Bou145 | V123A, Y133Q, I152A | SEQ ID No 152 |
| Bou146 | V123A, D127G | SEQ ID No 153 |
| Bou147 | V123A, D127A | SEQ ID No 154 |
| Bou148 | V123Q, D127G | SEQ ID No 155 |
| Bou149 | V123Q, D127A | SEQ ID No 156 |
| Bou150 | V123Q, E129G | SEQ ID No 157 |
| Bou151 | V123A, E129G | SEQ ID No 158 |
| Bou2 | V123T | SEQ ID No 130 |
| Bou3 | V123A | SEQ ID No 131 |
| Bou4 | V123Q | SEQ ID No 132 |
| Bou5 | D127G | SEQ ID No 133 |
| Bou6 | D127A | SEQ ID No 134 |
| Bou7 | E129Q | SEQ ID No 135 |
| Bou8 | E129G | SEQ ID No 136 |
| Bou9 | Y133N | SEQ ID No 137 |
| Bou10 | Y133T | SEQ ID No 138 |
| Bou11 | Y133A | SEQ ID No 139 |
| Bou12 | Y133R | SEQ ID No 140 |
| Bou13 | Y133D | SEQ ID No 141 |
| Bou14 | Y133E | SEQ ID No 142 |
| Bou15 | Y133Q | SEQ ID No 143 |
| Bou16 | Y133G | SEQ ID No 144 |
| Bou17 | Y133H | SEQ ID No 145 |
| Bou18 | Y133K | SEQ ID No 146 |
| Bou19 | Y133S | SEQ ID No 147 |
| Bou20 | I152Q | SEQ ID No 148 |
| Bou21 | I152A | SEQ ID No 149 |

*The numbering commences from residue 1 of the bouganin reading frame and therefore excludes a PeIB leader sequence included in most constructs.

TABLE 7

SEQ ID No 1
Protein
YNTVSFNLGEAYEYPTFIQDLRNELAKGTPVCQLPVTLQTIADDKRFVLVDITTTSKKTVKVAIDVTDVY

VVGYQDKWDGKDRAVFLDKVPTVATSKLFPGVTNRVTLTFDGSYQKLVNAAKVDRKDLELGVYKLEFSIE

AIHGKTINGQEIAKFFLIVIQMVSEAARFKYIETEVVDRGLYGSFKPNFKVLNLENNWGDISDAIHKSSP

QCTTINPALQLISPSNDPWVVNKVSQISPDMGILKFKSSK

SEQ ID No 13
Protein
YNTVSFNLGEAYEYPTFIQDLRNELAKGTPVCQLPVTLQTIADDKRFVLVDITTTSKKTVKVAIDVTDVY

VVGYQDKWDGKDRAVFLDKVPTVATSKLFPGVTNRVTLTFDGSYQKLVNAAKADRKALELGVNKLEFSIE

AIHGKTINGQEAAKFFLIVIQMVSEAARFKYIETEVVDRGLYGSFKPNFKVLNLENNWGDISDAIHKSSP

QCTTINPALQLISPSNDPWVVNKVSQISPDMGILKFKSSK

TABLE 8

Modified and WT peptides of Bouganin further tested in T cell assays.

| Peptide number | Position of first amino acid within bouganin | Sequence* | SEQ ID NO |
|---|---|---|---|
| DeI-41 | 121-135 | AKADRKALELGVNKL | 29 |
| DeI-44 | 130-144 | LGVNKLEFSIEAIHG | 30 |
| DeI-50 | 149-163 | NGQEAAKFFLIVIQM | 31 |

*Substituted (mutant) residue underlined.

TABLE 9

VB6-845 binding to gynecological cell lines by flow cytometry
Results are expressed as fold-increase in MF ± SEM.

| Indication | Cell lines | VB6-845 (fold increase MF ± SEM) |
|---|---|---|
| Endometrial | HEC-1-A | 42.3 ± 0.9 |
|  | RL95-2 | 4.9 ± 0.7 |
|  | SK-UT-1 | 1.1 ± 0.1 |
| Ovarian | NIH: OVCAR-3 | 33.6 ± 6.0 |
|  | SK-OV-3 | 4.3 ± 1.0 |
|  | TOV-112G | 1.1 ± 0.1 |
| Cervical | HT-3 | 29.1 ± 1.2 |
|  | C-4 I | 6.8 ± 0.6 |
|  | C-33A | 1.1 ± 0.0 |
| Melanoma | A-375 | 1.1 ± 0.1 |

TABLE 10

VB6-845-mediated Cytotoxicity by MTS assay

| Indication | Cell line | $IC_{50}$ nM VB6-845 70% pure |
|---|---|---|
| Endometrial | HEC-1-A | 43 |
|  | KLE | >100 |
|  | RL95-2 | 100 |
| Ovarian | NIH-OVCAR-3 | 3.4 |
|  | Caov-3 | 1.3 |
|  | SK-OV-3 | >100 |
| Cervical | MS751 | 0.43 |
|  | HT-3 | 23 |
|  | ME-180 | 37 |
|  | C-4 I | 1.7 |
| Melanoma | A-375 | >100 |

TABLE 11

Specificity and selectivity of VB6-845 Versus Chemotherapeutics

| | $IC_{50}$ nM | | | |
|---|---|---|---|---|
| | NIH: OVCAR-3 | A-375 | DAUDI | HMEC |
| Paclitaxel | $<10^{-6}$ | $4.9 \times 10^{-6}$ | $<10^{-6}$ | $<10^{-6}$ |
| Docetaxel | $<10^{-6}$ | $<10^{-6}$ | $<10^{-6}$ | $<10^{-6}$ |
| Vincristine | $4.4 \times 10^{-6}$ | $<10^{-6}$ | $<10^{-6}$ | $<10^{-6}$ |
| Vinblastine Sulfate | $1.1 \times 10^{-6}$ | $<10^{-6}$ | $<10^{-6}$ | $<10^{-6}$ |
| Topotecan | 0.071 | 1.5 | 0.009 | 4.1 |
| VB6-845 (90% pure) | 1 | >1000 | >1000 | 220 |
| Doxorubicin | 3 | 2.8 | $16 \times 10^{-6}$ | 16 |
| Mitomycin C | 28 | 14 | 2.8 | 50 |
| Bleomycin Sulfate | 30 | 170 | 22 | 600 |
| Bleomycin A5 | 150 | 290 | 130 | 1000 |
| Irinotecan | 180 | 900 | 190 | 1000 |
| Etoposide | 210 | 280 | 1.7 | 600 |
| Methotrexate | >1000 | 6 | 3.6 | 41 |
| Chlorambucil | >1000 | >1000 | >1000 | >1000 |
| Fluorouracil | >1000 | >1000 | >1000 | >1000 |
| Cyclophosphamide | >1000 | >1000 | >1000 | >1000 |
| Cisplatin | >1000 | >1000 | >1000 | >1000 |
| Carboplatin | >1000 | >1000 | >1000 | >1000 |

TABLE 12

VB6-845 Tumor Cell Indications

| INDICATIONS | N[1] | Binding for scFv 845 (IgG)[2] |
|---|---|---|
| Gastric | 3 | 148.9 |
| Ovarian | 2 | 84.1 |
| Esophageal | 3 | 72.4 |
| Bladder | 14 | 59.6 |
| Prostate | 5 | 50.1 |

TABLE 12-continued

VB6-845 Tumor Cell Indications

| INDICATIONS | N[1] | Binding for scFv 845 (IgG)[2] |
|---|---|---|
| Cervical | 3 | 37.5 |
| Endometrial | 1 | 23.8 |
| Lung | 3 | 16.4 |
| Head and Neck | 2 | 11.4 |
| Kidney | 3 | 9.4 |
| Pancreas | 3 | 5.5 |
| Melanoma | 3 | 1.6 |

[1]N indicates the number of cell lines tested per indication.
[2]Mean fold-increase in median fluorescence over the control antibody from all cell lines in each indication.

TABLE 13

VB6-011 Tumor Cell Indications

| INDICATIONS | N[1] | Binding for mAb 011 (IgG)[2] |
|---|---|---|
| Breast | 3 | 16.9 |
| Prostate | 3 | 15.1 |
| Melanoma | 3 | 14.0 |
| Lung | 3 | 13.1 |
| Ovarian | 2 | 11.1 |
| Colon | 3 | 8.7 |
| Kidney | 3 | 6.9 |
| Liver | 2 | 6.5 |
| Pancreas | 3 | 4.2 |
| Head and Neck | 2 | 2.9 |

[1]N indicates the number of cell lines tested per indication.
[2]Values indicate the mean calculated from the sum of the mean fold increase in median fluorescence over the control antibody from all cell lines in each indication. A zero value would mean no measurable reactivity relative to the control activity

We claim:

1. A modified bouganin protein having reduced propensity to elicit an immune response as compared to non-modified bouganin protein (SEQ ID NO: 1), wherein the amino acid sequence of the modified bouganin protein comprises:

```
                                    (SEQ ID NO: 11)
YNTVSFNLGEAYEYPTFIQDLRNELAKGTPVCQLPVTLQTIADDKRFVLV

DITTTSKKTVKVAIDVTDVYVVGYQDKWDGKDRAVFLDKVPTVATSKLFP

GVTNRVTLTFDGSYQKLVNAAKX¹DRKX²LX³LGVX⁴KLEFSIEAIHGKT

INGQEX⁵AKFFLIVIQMVSEAARFKYIETEVVDRGLYGSFKPNFKVLNLE

NNWGDISDAIHKSSPQCTTINPALQLISPSNDPWVVNKVSQISPDMGILK

FKSSK
``` wherein $X^1$ through $X^5$ can be any amino acid, provided that the amino acid sequence of the modified bouganin protein is not identical to the non-modified bouganin protein (SEQ ID NO: 1), wherein said modified bouganin protein inhibits protein synthesis on ribosomes.

2. The modified bouganin according to claim 1 wherein:

$X^1$ is T or A or Q;

$X^2$ is G or A;

$X^3$ is Q or G;

$X^4$ is N or D or T or A or R or Q or E or G or H or K or S; and $X^5$ is Q or A (SEQ ID NO: 12).

3. The modified bouganin protein according to claim 1 wherein the modified bouganin comprises the following sequence:

```
                                                    (SEQ ID NO: 13)
YNTVSFNLGEAYEYPTFIQDLRNELAKGTPVCQLPVTLQTIADDKRFV

LVDITTTSKKTVKVAIDVTDVYVVGYQDKWDGKDRAVFLDKVPTVAT

SKLFPGVTNRVTLTFDGSYQLVNAAKADRKALELGVNKLEFSIEAIH

GKTINGQEAAKFFLIVIQMVSEAARFKYIETEVVDRGLYGSFKPNFKVL

NLENNWGDISDAIHKSSPQCTTINPALQLISPSNDPWVVNKVSQISPD

MGILKFKSSK.
```

4. A cytotoxin comprising
(a) a targeting moiety attached to;
(b) the modified bouganin protein according to claim 1.

5. A cytotoxin comprising
(a) a ligand that binds to a cancer cell attached to;
(b) the modified bouganin protein according to claim 1.

6. The cytotoxin of claim 5, wherein the ligand is an antibody or antibody fragment that binds to the cancer cell.

7. The cytotoxin of claim 6, wherein the antibody or antibody fragment binds to Ep-CAM on the surface of the cancer cell.

8. The cytotoxin of claim 7, wherein the antibody or antibody fragment that binds to Ep-CAM is a humanized antibody or antibody fragment that binds to the extracellular domain of human Ep-CAM and comprises complementarity determining region sequences derived from a MOC-31 antibody.

9. The cytotoxin of claim 7, wherein the variable region of the cancer-binding ligand attached to the modified bouganin protein is 4D5MOCB.

10. The cytotoxin of claim 6, wherein the antibody or antibody fragment binds to a tumor-associated antigen on the surface of the cancer cell.

11. A pharmaceutical composition comprising the cytotoxin according to claim 4 and a pharmaceutically acceptable carrier, diluent or excipient.

12. The modified bouganin protein according to claim 1, wherein said immune response is T cell activity.

13. The modified bouganin protein according to claim 6, wherein the modified bouganin is selected from the group consisting of:
wherein $X^1$ is T, $X^2$ is D, $X^3$ is E, $X^4$ is Y, and $X^5$ is I (SEQ ID NO: 130);
wherein $X^1$ is A, $X^2$ is D, $X^3$ is E, $X^4$ is Y, and $X^5$ is I (SEQ ID NO: 131);
wherein $X^1$ is Q, $X^2$ is D, $X^3$ is E, $X^4$ is Y, and $X^5$ is I (SEQ ID NO: 132);
wherein $X^1$ is V, $X^2$ is G, $X^3$ is E, $X^4$ is Y, and $X^5$ is I (SEQ ID NO: 133);
wherein $X^1$ is V, $X^2$ is A, $X^3$ is E, $X^4$ is Y, and $X^5$ is I (SEQ ID NO: 134);
wherein $X^1$ is V, $X^2$ is D, $X^3$ is Q, $X^4$ is Y, and $X^5$ is I (SEQ ID NO: 135);
wherein $X^1$ is V, $X^2$ is D, $X^3$ is G, $X^4$ is Y, and $X^5$ is I (SEQ ID NO: 136);
wherein $X^1$ is V, $X^2$ is D, $X^3$ is E, $X^4$ is N, and $X^5$ is I (SEQ ID NO: 137);
wherein $X^1$ is V, $X^2$ is D, $X^3$ is E, $X^4$ is T, and $X^5$ is I (SEQ ID NO: 138);
wherein $X^1$ is V, $X^2$ is D, $X^3$ is E, $X^4$ is A, and $X^5$ is I (SEQ ID NO: 139);
wherein $X^1$ is V, $X^2$ is D, $X^3$ is E, $X^4$ is R, and $X^5$ is I (SEQ ID NO: 140);
wherein $X^1$ is V, $X^2$ is D, $X^3$ is E, $X^4$ is D, and $X^5$ is I (SEQ ID NO: 141);
wherein $X^1$ is V, $X^2$ is D, $X^3$ is E, $X^4$ is E, and $X^5$ is I (SEQ ID NO: 142);
wherein $X^1$ is V, $X^2$ is D, $X^3$ is E, $X^4$ is Q, and $X^5$ is I (SEQ ID NO: 143);
wherein $X^1$ is V, $X^2$ is D, $X^3$ is E, $X^4$ is G, and $X^5$ is I (SEQ ID NO: 144);
wherein $X^1$ is V, $X^2$ is D, $X^3$ is E, $X^4$ is H, and $X^5$ is I (SEQ ID NO: 145);
wherein $X^1$ is V, $X^2$ is D, $X^3$ is E, $X^4$ is K, and $X^5$ is I (SEQ ID NO: 146);
wherein $X^2$ is V, $X^2$ is D, $X^3$ is E, $X^4$ is V, and $X^5$ is I (SEQ ID NO: 147);
wherein $X^1$ is V, $X^2$ is D, $X^3$ is E, $X^4$ is y, and $X^5$ is Q (SEQ ID NO: 148);
wherein $X^1$ is V, $X^2$ is D, $X^3$ is E, $X^4$ is Y, and $X^5$ is A (SEQ ID NO: 149);
wherein $X^1$ is Q, $X^2$ is D, $X^3$ is E, $X^4$ is Q, and $X^5$ is Q (SEQ ID NO: 150);
wherein $X^1$ is A, $X^2$ is D, $X^3$ is E, $X^4$ is N, and $X^5$ is A (SEQ ID NO: 151);
wherein $X^1$ is A, $X^2$ is D, $X^3$ is E, $X^4$ is Q, and $X^5$ is A (SEQ ID NO: 152);
wherein $X^1$ is A, $X^2$ is G, $X^3$ is E, $X^4$ is Y, and $X^5$ is I (SEQ ID NO: 153);
wherein $X^1$ is A, $X^2$ is A, $X^3$ is E, $X^4$ is Y, and $X^5$ is I (SEQ ID NO: 154);
wherein $X^1$ is Q, $X^2$ is G, $X^3$ is E, $X^4$ is y, and $X^5$ is I (SEQ ID NO: 155);
wherein $X^1$ is Q, $X^2$ is A, $X^3$ is E, $X^4$ is Y, and $X^5$ is I (SEQ ID NO: 156);
wherein $X^1$ is Q, $X^2$ is D, $X^3$ is G, $X^4$ is y, and $X^5$ is I (SEQ ID NO: 157);
wherein $X^1$ is A, $X^2$ is D, $X^3$ is G, $X^4$ is Y, and $X^5$ is I (SEQ ID NO: 158); and
wherein $X^1$ is A, $X^2$ is A, $X^3$ is E, $X^4$ is Q, and $X^5$ is A (SEQ ID NO: 14).

14. A cytotoxin comprising
(a) a targeting moiety attached to;
(b) the modified bouganin protein according to claim 13.

15. A cytotoxin comprising
(a) a targeting moiety attached to;
(b) the modified bouganin protein according to claim 3.

16. A cytotoxin comprising
(a) a ligand that binds to a cancer cell attached to;
(b) the modified bouganin protein according to claim 13.

17. A cytotoxin comprising
(a) a ligand that binds to a cancer cell attached to;
(b) the modified bouganin protein according to claim 3.

18. A pharmaceutical composition comprising the cytotoxin according to claim 14 and a pharmaceutically acceptable carrier, diluent or excipient.

19. A pharmaceutical composition comprising the cytotoxin according to claim 15 and a pharmaceutically acceptable carrier, diluent or excipient.

* * * * *

UNITED STATES PATENT AND TRADEMARK OFFICE
CERTIFICATE OF CORRECTION

PATENT NO.        : 7,339,031 B2                                      Page 1 of 1
APPLICATION NO.   : 11/084080
DATED             : March 4, 2008
INVENTOR(S)       : Matthew Baker et al.

It is certified that error appears in the above-identified patent and that said Letters Patent is hereby corrected as shown below:

In claim 13 at column 135, line 41, "claim 6" should read --claim 1--;

In claim 13 at column 136, line 15, "wherein $X^2$ is V" should read --wherein $X^1$ is V-- and "$X^4$ is V" should read --$X^4$ is S--;

In claim 13 at column 136, line 32, "$X^4$ is y" should read --$X^4$ is Y--; and In claim 13 at column 136, line 36, "$X^4$ is y" should read --$X^4$ is Y--.

Signed and Sealed this
Third Day of January, 2012

David J. Kappos
*Director of the United States Patent and Trademark Office*

```
                       SEQUENCE LISTING

<160> NUMBER OF SEQ ID NOS: 129

<210> SEQ ID NO 1
<211> LENGTH: 250
<212> TYPE: PRT
<213> ORGANISM: Bougainvillea spectabilis Wild

<400> SEQUENCE: 1

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Val Asp Arg Lys Asp Leu
        115                 120                 125

Glu Leu Gly Val Tyr Lys Leu Glu Phe Ser Ile Glu Ala Ile His Gly
    130                 135                 140

Lys Thr Ile Asn Gly Gln Glu Ile Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
```

-continued

```
                195                 200                 205
Ser Pro Gln Cys Thr Thr Ile Asn Pro Ala Leu Gln Leu Ile Ser Pro
    210                 215                 220
Ser Asn Asp Pro Trp Val Val Asn Lys Val Ser Gln Ile Ser Pro Asp
225                 230                 235                 240
Met Gly Ile Leu Lys Phe Lys Ser Ser Lys
                245                 250

<210> SEQ ID NO 2
<211> LENGTH: 15
<212> TYPE: PRT
<213> ORGANISM: Bougainvillea spectabilis

<400> SEQUENCE: 2

Ala Lys Val Asp Arg Lys Asp Leu Glu Leu Gly Val Tyr Lys Leu
1               5                   10                  15

<210> SEQ ID NO 3
<211> LENGTH: 15
<212> TYPE: PRT
<213> ORGANISM: Bougainvillea spectabilis

<400> SEQUENCE: 3

Leu Gly Val Tyr Lys Leu Glu Phe Ser Ile Glu Ala Ile His Gly
1               5                   10                  15

<210> SEQ ID NO 4
<211> LENGTH: 15
<212> TYPE: PRT
<213> ORGANISM: Bougainvillea spectabilis

<400> SEQUENCE: 4

Asn Gly Gln Glu Ile Ala Lys Phe Phe Leu Ile Val Ile Gln Met
1               5                   10                  15

<210> SEQ ID NO 5
<211> LENGTH: 15
<212> TYPE: PRT
<213> ORGANISM: Bougainvillea spectabilis
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 5

Ala Lys Xaa Asp Arg Lys Xaa Leu Xaa Leu Gly Val Xaa Lys Leu
1               5                   10                  15

<210> SEQ ID NO 6
<211> LENGTH: 15
<212> TYPE: PRT
<213> ORGANISM: Bougainvillea spectabilis
<220> FEATURE:
<221> NAME/KEY: misc_feature
<222> LOCATION: (4)..(4)
```

```
<223> OTHER INFORMATION: Xaa can be any naturally occurring amino acid

<400> SEQUENCE: 6

Leu Gly Val Xaa Lys Leu Glu Phe Ser Ile Glu Ala Ile His Gly
1               5                   10                  15

<210> SEQ ID NO 7
<211> LENGTH: 15
<212> TYPE: PRT
<213> ORGANISM: Bougainvillea spectabilis
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Asn Gly Gln Glu Xaa Ala Lys Phe Phe Leu Ile Val Ile Gln Met
1               5                   10                  15

<210> SEQ ID NO 8
<211> LENGTH: 15
<212> TYPE: PRT
<213> ORGANISM: Bougainvillea spectabilis
<220> FEATURE:
<221> NAME/KEY: MISC_FEATURE
<222> LOCATION: (3)..(3)
<223> OTHER INFORMATION: Xaa can be T or A or Q
<220> FEATURE:
<221> NAME/KEY: MISC_FEATURE
<222> LOCATION: (7)..(7)
<223> OTHER INFORMATION: Xaa can be G or A
<220> FEATURE:
<221> NAME/KEY: MISC_FEATURE
<222> LOCATION: (9)..(9)
<223> OTHER INFORMATION: Xaa can be Q or G
<220> FEATURE:
<221> NAME/KEY: MISC_FEATURE
<222> LOCATION: (13)..(13)
<223> OTHER INFORMATION: Xaa can be N or D or T or A or R or Q or E or G
      or H or K or S

<400> SEQUENCE: 8

Ala Lys Xaa Asp Arg Lys Xaa Leu Xaa Leu Gly Val Xaa Lys Leu
1               5                   10                  15

<210> SEQ ID NO 9
<211> LENGTH: 15
<212> TYPE: PRT
<213> ORGANISM: Bougainvillea spectabilis
<220> FEATURE:
<221> NAME/KEY: MISC_FEATURE
<222> LOCATION: (4)..(4)
<223> OTHER INFORMATION: Xaa can be N or D or T or A or R or Q or E or G
      or H or K or S

<400> SEQUENCE: 9

Leu Gly Val Xaa Lys Leu Glu Phe Ser Ile Glu Ala Ile His Gly
1               5                   10                  15

<210> SEQ ID NO 10
<211> LENGTH: 15
<212> TYPE: PRT
<213> ORGANISM: Bougainvillea spectabilis
<220> FEATURE:
<221> NAME/KEY: MISC_FEATURE
<222> LOCATION: (5)..(5)
<223> OTHER INFORMATION: Xaa can be Q or A

<400> SEQUENCE: 10

Asn Gly Gln Glu Xaa Ala Lys Phe Phe Leu Ile Val Ile Gln Met
```

-continued

<210> SEQ ID NO 11
<211> LENGTH: 250
<212> TYPE: PRT
<213> ORGANISM: Bougainvillea spectabilis
<220> FEATURE:
<221> NAME/KEY: misc_feature
<222> LOCATION: (123)..(123)
<223> OTHER INFORMATION: Xaa can be any naturally occurring amino acid
<220> FEATURE:
<221> NAME/KEY: misc_feature
<222> LOCATION: (127)..(127)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (152)..(152)
<223> OTHER INFORMATION: Xaa can be any naturally occurring amino acid

<400> SEQUENCE: 11

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Xaa Asp Arg Lys Xaa Leu
        115                 120                 125

Xaa Leu Gly Val Xaa Lys Leu Glu Phe Ser Ile Glu Ala Ile His Gly
    130                 135                 140

Lys Thr Ile Asn Gly Gln Glu Xaa Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250

<210> SEQ ID NO 12
<211> LENGTH: 250
<212> TYPE: PRT
<213> ORGANISM: Bougainvillea spectabilis
<220> FEATURE:
<221> NAME/KEY: MISC_FEATURE
<222> LOCATION: (123)..(123)
<223> OTHER INFORMATION: Xaa can be T or A or Q
<220> FEATURE:
<221> NAME/KEY: MISC_FEATURE
<222> LOCATION: (127)..(127)
<223> OTHER INFORMATION: Xaa can be G or A
<220> FEATURE:
<221> NAME/KEY: MISC_FEATURE
<222> LOCATION: (129)..(129)
<223> OTHER INFORMATION: Xaa can be Q or G
<220> FEATURE:
<221> NAME/KEY: MISC_FEATURE
<222> LOCATION: (133)..(133)
<223> OTHER INFORMATION: Xaa can be N or D or T or A or R or Q or E or G
     or H or K or S
<220> FEATURE:
<221> NAME/KEY: MISC_FEATURE
<222> LOCATION: (152)..(152)
<223> OTHER INFORMATION: Xaa can be Q or A

<400> SEQUENCE: 12

Tyr Asn Thr Val Ser Phe Asn Leu Gly Glu Ala Tyr Glu Tyr Pro Thr
 1               5                  10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Xaa Asp Arg Lys Xaa Leu
        115                 120                 125

Xaa Leu Gly Val Xaa Lys Leu Glu Phe Ser Ile Glu Ala Ile His Gly
    130                 135                 140

Lys Thr Ile Asn Gly Gln Glu Xaa Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250

<210> SEQ ID NO 13
<211> LENGTH: 250

```
<212> TYPE: PRT
<213> ORGANISM: Bougainvillea spectabilis

<400> SEQUENCE: 13

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Asn Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250

<210> SEQ ID NO 14
<211> LENGTH: 250
<212> TYPE: PRT
<213> ORGANISM: Bougainvillea spectabilis

<400> SEQUENCE: 14

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Tyr Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95
```

```
Lys Leu Phe Pro Gly Val Thr Asn Arg Val Thr Leu Thr Phe Asp Gly
            100                 105                 110

Ser Tyr Gln Lys Leu Val Asn Ala Ala Lys Ala Asp Arg Lys Ala Leu
        115                 120                 125

Glu Leu Gly Val Gln Lys Leu Glu Phe Ser Ile Glu Ala Ile His Gly
    130                 135                 140

Lys Thr Ile Asn Gly Gln Glu Ala Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
            245                 250

<210> SEQ ID NO 15
<211> LENGTH: 2404
<212> TYPE: DNA
<213> ORGANISM: Artificial Sequence
<220> FEATURE:
<223> OTHER INFORMATION: VB6-845

<400> SEQUENCE: 15
gaattcctgc aggtctatgg aacgataaat gcccatgaaa attctatttc aaggagacag      60
tcataatgaa atacctattg cctacggcag ccgctggatt gttattactc gctgcccaac     120
cagcgatggc ggaagtacag ctggttcagt ccggcccggg tcttgttcaa ccgggtggtt     180
ccgttcgtat ctcttgcgct gcttctggtt acacgttcac caactacggc atgaactggg     240
tcaaacaggc tccgggtaaa ggcctggaat ggatgggctg atcaacacc tacaccggtg      300 aatccaccta cgctgactcc ttcaaaggtc gcttcacttt ctccctcgac acaagtgcta     360
gtgctgcata cctccaaatc aactcgctgc gtgcagagga tacagcagtc tattactgcg     420
cccgtttcgc tatcaaaggt gactactggg tcaaggcac gctgctgacc gtttcctcgg      480
ctagcaccaa aggcccatcg tcttcccccc tggcaccctc ctccaagagc acctctgggg     540
gcacagcggc cctgggctgc ctggtcaagg actacttccc cgaaccggtg acggtgtcgt     600
ggaactcagg cgccctgacc agcggcgtgc acaccttccc ggctgtccta cagtcctcag     660
gactctactc cctcagcagc gtggtgaccg tgccctccag cagcttgggc acccagacct     720
acatctgcaa cgtgaatcac aagcccagca caccaaggt ggacaagaaa gttgagccca      780 atcttgtac aggcacagg cagcccagag ctgggagca gctctacaac accgtgtcat        840
ttaaccttgg agaagcttat gagtacccca ctttttataca agatttgcgc aatgaattgg    900
ctaagggcac accagtatgt caacttccag tgacactaca accatagcc gatgacaagc      960 gatttgttct agttgatatc actacgacct cgaagaaaac agttaaggtt gctatagatg    1020
tgacagatgt gtatgttgtg ggttatcaag acaaatggga tggcaaagat cgagctgttt    1080
tccttgacaa ggttcctact gttgcaacta gtaaacttt cccagggtg actaatcgtg      1140 taacgttaac atttgatggc agctatcaga aacttgtgaa tgctgccaaa gctgatagaa    1200
```

-continued

```
aggctctcga actgggggtt aacaaattgg aattttccat tgaagcaatc catggtaaaa    1260
cgataaatgg tcaagaggca gccaagttct ttcttattgt catccaaatg gtttcagagg    1320
cagctcggtt caaatatatt gagactgagg tggttgatag aggattatat ggatcattca    1380
aacctaattt taaagtattg aacttggaga acaattgggg cgacatctct gatgccattc    1440
acaaatcatc cccacaatgt accactatta atccggcact tcagttgata agcccctcaa    1500
atgacccatg ggttgtaaat aaagtgagtc aaattagtcc cgatatgggt atccttaagt    1560
ttaaaagctc caaatagtga tctagagtcg acctgcaggt ctatggaacg ataaatgccc    1620
atgaaaattc tatttcaagg agacagtcat aatgaaatac ctattgccta cggcagccgc    1680
tggattgtta ttactcgctg cccaaccagc gatggcgcac catcatcacc atcacgatat    1740
ccagatgacc cagtccccgt cctccctgag tgcttctgtt ggtgaccgtg ttaccatcac    1800
ctgccgttcc accaaatccc tcctgcactc aacggtatc acctaccttt attggtatca    1860
acagaaaccg ggtaaagctc cgaaacttct gatctaccag atgtccaacc tggcttccgg    1920
tgttccgtct cgtttctcca gttctggttc tggtaccgac ttcaccctga ccatctcttc    1980
tctgcagccg gaagacttcg ctacctacta ctgcgctcag aacctggaaa tcccgcgtac    2040
cttcggtcag ggtaccaaag ttgaacttaa gcgcactgtg gctgcaccat ctgtcttcat    2100
cttcccgcca tctgatgagc agttgaaatc tggaactgcc tctgttgtgt gcctgctgaa    2160
taacttctat cccagagagg ccaaagtaca gtggaaggtg gataacgccc tccaatcggg    2220
taactcccag gagagtgtca cagagcagga cagcaaggac agcacctaca gcctcagcag    2280
caccctgacg ctgagcaaag cagactacga gaaacacaaa gtctacgcct gcgaagtcac    2340
ccatcagggc ctgagctcgc ccgtcacaaa gagcttcaac aggggagagt gttagtagct    2400
cgag                                                                 2404
```

<210> SEQ ID NO 16
<211> LENGTH: 750
<212> TYPE: PRT
<213> ORGANISM: Artificial Sequence
<220> FEATURE:
<223> OTHER INFORMATION: VB6-845

<400> SEQUENCE: 16

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Gln Ser Gly Pro Gly
            20                  25                  30

Leu Val Gln Pro Gly Gly Ser Val Arg Ile Ser Cys Ala Ala Ser Gly
        35                  40                  45

Tyr Thr Phe Thr Asn Tyr Gly Met Asn Trp Val Lys Gln Ala Pro Gly
    50                  55                  60

Lys Gly Leu Glu Trp Met Gly Trp Ile Asn Thr Tyr Thr Gly Glu Ser
65                  70                  75                  80

Thr Tyr Ala Asp Ser Phe Lys Gly Arg Phe Thr Phe Ser Leu Asp Thr
                85                  90                  95

Ser Ala Ser Ala Ala Tyr Leu Gln Ile Asn Ser Leu Arg Ala Glu Asp
            100                 105                 110

Thr Ala Val Tyr Tyr Cys Ala Arg Phe Ala Ile Lys Gly Asp Tyr Trp
        115                 120                 125

Gly Gln Gly Thr Leu Leu Thr Val Ser Ser Ala Ser Thr Lys Gly Pro
    130                 135                 140
```

-continued

```
Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Thr Arg His Arg Gln Pro Arg Gly Trp Glu Gln Leu Tyr Asn Thr
                245                 250                 255

Val Ser Phe Asn Leu Gly Glu Ala Tyr Glu Tyr Pro Thr Phe Ile Gln
            260                 265                 270

Asp Leu Arg Asn Glu Leu Ala Lys Gly Thr Pro Val Cys Gln Leu Pro
        275                 280                 285

Val Thr Leu Gln Thr Ile Ala Asp Asp Lys Arg Phe Val Leu Val Asp
    290                 295                 300

Ile Thr Thr Thr Ser Lys Lys Thr Val Lys Val Ala Ile Asp Val Thr
305                 310                 315                 320

Asp Val Tyr Val Val Gly Tyr Gln Asp Lys Trp Asp Gly Lys Asp Arg
                325                 330                 335

Ala Val Phe Leu Asp Lys Val Pro Thr Val Ala Thr Ser Lys Leu Phe
            340                 345                 350

Pro Gly Val Thr Asn Arg Val Thr Leu Thr Phe Asp Gly Ser Tyr Gln
        355                 360                 365

Lys Leu Val Asn Ala Ala Lys Ala Asp Arg Lys Ala Leu Glu Leu Gly
    370                 375                 380

Val Asn Lys Leu Glu Phe Ser Ile Glu Ala Ile His Gly Lys Thr Ile
385                 390                 395                 400

Asn Gly Gln Glu Ala Ala Lys Phe Phe Leu Ile Val Ile Gln Met Val
                405                 410                 415

Ser Glu Ala Ala Arg Phe Lys Tyr Ile Glu Thr Glu Val Val Asp Arg
            420                 425                 430

Gly Leu Tyr Gly Ser Phe Lys Pro Asn Phe Lys Val Leu Asn Leu Glu
        435                 440                 445

Asn Asn Trp Gly Asp Ile Ser Asp Ala Ile His Lys Ser Ser Pro Gln
    450                 455                 460

Cys Thr Thr Ile Asn Pro Ala Leu Gln Leu Ile Ser Pro Ser Asn Asp
465                 470                 475                 480

Pro Trp Val Val Asn Lys Val Ser Gln Ile Ser Pro Asp Met Gly Ile
                485                 490                 495

Leu Lys Phe Lys Ser Ser Lys Met Lys Tyr Leu Leu Pro Thr Ala Ala
            500                 505                 510

Ala Gly Leu Leu Leu Leu Ala Ala Gln Pro Ala Met Ala His His
        515                 520                 525

His His His Asp Ile Gln Met Thr Gln Ser Pro Ser Ser Leu Ser Ala
    530                 535                 540

Ser Val Gly Asp Arg Val Thr Ile Thr Cys Arg Ser Thr Lys Ser Leu
545                 550                 555                 560
```

-continued

```
Leu His Ser Asn Gly Ile Thr Tyr Leu Tyr Trp Tyr Gln Gln Lys Pro
            565                 570                 575
Gly Lys Ala Pro Lys Leu Leu Ile Tyr Gln Met Ser Asn Leu Ala Ser
        580                 585                 590
Gly Val Pro Ser Arg Phe Ser Ser Gly Ser Gly Thr Asp Phe Thr
    595                 600                 605
Leu Thr Ile Ser Ser Leu Gln Pro Glu Asp Phe Ala Thr Tyr Tyr Cys
610                 615                 620
Ala Gln Asn Leu Glu Ile Pro Arg Thr Phe Gly Gln Gly Thr Lys Val
625                 630                 635                 640
Glu Leu Lys Arg Thr Val Ala Ala Pro Ser Val Phe Ile Phe Pro Pro
            645                 650                 655
Ser Asp Glu Gln Leu Lys Ser Gly Thr Ala Ser Val Val Cys Leu Leu
        660                 665                 670
Asn Asn Phe Tyr Pro Arg Glu Ala Lys Val Gln Trp Lys Val Asp Asn
    675                 680                 685
Ala Leu Gln Ser Gly Asn Ser Gln Glu Ser Val Thr Glu Gln Asp Ser
690                 695                 700
Lys Asp Ser Thr Tyr Ser Leu Ser Ser Thr Leu Thr Leu Ser Lys Ala
705                 710                 715                 720
Asp Tyr Glu Lys His Lys Val Tyr Ala Cys Glu Val Thr His Gln Gly
            725                 730                 735
Leu Ser Ser Pro Val Thr Lys Ser Phe Asn Arg Gly Glu Cys
        740                 745                 750

<210> SEQ ID NO 17
<211> LENGTH: 1618
<212> TYPE: DNA
<213> ORGANISM: Artificial Sequence
<220> FEATURE:
<223> OTHER INFORMATION: VB5-845

<400> SEQUENCE: 17
gaattcctgc aggtctatgg aacgataaat gcccatgaaa attctatttc aaggagacag      60
tcataatgaa ataccattg cctacggcag ccgctggatt gttattactc gctgcccaac     120
cagcgatggc ggaagtacag ctggttcagt ccggcccggg tcttgttcaa ccgggtggtt     180
ccgttcgtat ctcttgcgct gcttctggtt acacgttcac caactacggc atgaactggg     240
tcaaacaggc tccgggtaaa ggcctggaat ggatgggctg atcaacacc tacaccggtg     300
aatccaccta cgctgactcc ttcaaaggtc gcttcacttt ctccctcgac acaagtgcta     360
gtgctgcata cctccaaatc aactcgctgc gtgcagagga tacagcagtc tattactgcg     420
cccgtttcgc tatcaaaggt gactactggg gtcaaggcac gctgctgacc gtttcctcgg     480
ctagcaccaa aggcccatcg gtcttccccc tggcaccctc ctccaagagc acctctgggg     540
gcacagcggc cctgggctgc ctggtcaagg actacttccc cgaaccggtg acggtgtcgt     600
ggaactcagg cgccctgacc agcggcgtgc acaccttccc ggctgtccta cagtcctcag     660
gactctactc cctcagcagc gtggtgaccg tgccctccag cagcttgggc acccagacct     720
acatctgcaa cgtgaatcac aagcccagca acaccaaggt ggacaagaaa gttgagccca     780
aatcttgtta gtgatctaga gtcgacctgc aggtctatgg aacgataaat gcccatgaaa     840
attctatttc aaggagacag tcataatgaa ataccattg cctacggcag ccgctggatt     900
gttattactc gctgcccaac cagcgatggc gcaccatcat caccatcacg atatccagat     960
gacccagtcc ccgtcctccc tgagtgcttc tgttggtgac cgtgttacca tcacctgccg    1020
```

-continued

```
ttccaccaaa tccctcctgc actccaacgg tatcacctac ctttattggt atcaacagaa    1080
accgggtaaa gctccgaaac ttctgatcta ccagatgtcc aacctggctt ccggtgttcc    1140
gtctcgtttc tccagttctg gttctggtac cgacttcacc ctgaccatct cttctctgca    1200
gccggaagac ttcgctacct actactgcgc tcagaacctg gaaatcccgc gtaccttcgg    1260
tcagggtacc aaagttgaac ttaagcgcac tgtggctgca ccatctgtct tcatcttccc    1320
gccatctgat gagcagttga aatctggaac tgcctctgtt gtgtgcctgc tgaataactt    1380
ctatcccaga gaggccaaag tacagtggaa ggtggataac gccctccaat cgggtaactc    1440
ccaggagagt gtcacagagc aggacagcaa ggacagcacc tacagcctca gcagcaccct    1500
gacgctgagc aaagcagact acgagaaaca caaagtctac gcctgcgaag tcacccatca    1560
gggcctgagc tcgcccgtca caaagagctt caacagggga gagtgttagt agctcgag     1618
```

<210> SEQ ID NO 18
<211> LENGTH: 488
<212> TYPE: PRT
<213> ORGANISM: Artificial Sequence
<220> FEATURE:
<223> OTHER INFORMATION: VB5-845

<400> SEQUENCE: 18

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Gln Ser Gly Pro Gly
            20                  25                  30

Leu Val Gln Pro Gly Gly Ser Val Arg Ile Ser Cys Ala Ala Ser Gly
        35                  40                  45

Tyr Thr Phe Thr Asn Tyr Gly Met Asn Trp Val Lys Gln Ala Pro Gly
    50                  55                  60

Lys Gly Leu Glu Trp Met Gly Trp Ile Asn Thr Tyr Thr Gly Glu Ser
65                  70                  75                  80

Thr Tyr Ala Asp Ser Phe Lys Gly Arg Phe Thr Phe Ser Leu Asp Thr
                85                  90                  95

Ser Ala Ser Ala Ala Tyr Leu Gln Ile Asn Ser Leu Arg Ala Glu Asp
            100                 105                 110

Thr Ala Val Tyr Tyr Cys Ala Arg Phe Ala Ile Lys Gly Asp Tyr Trp
        115                 120                 125

Gly Gln Gly Thr Leu Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Met Lys Tyr Leu Leu Pro Thr Ala Ala Ala Gly Leu Leu Leu Leu
                245                 250                 255
```

Ala Ala Gln Pro Ala Met Ala His His His His His Asp Ile Gln
                260                 265                 270

Met Thr Gln Ser Pro Ser Ser Leu Ser Ala Ser Val Gly Asp Arg Val
            275                 280                 285

Thr Ile Thr Cys Arg Ser Thr Lys Ser Leu Leu His Ser Asn Gly Ile
        290                 295                 300

Thr Tyr Leu Tyr Trp Tyr Gln Gln Lys Pro Gly Lys Ala Pro Lys Leu
305                 310                 315                 320

Leu Ile Tyr Gln Met Ser Asn Leu Ala Ser Gly Val Pro Ser Arg Phe
                325                 330                 335

Ser Ser Ser Gly Ser Gly Thr Asp Phe Thr Leu Thr Ile Ser Ser Leu
            340                 345                 350

Gln Pro Glu Asp Phe Ala Thr Tyr Tyr Cys Ala Gln Asn Leu Glu Ile
        355                 360                 365

Pro Arg Thr Phe Gly Gln Gly Thr Lys Val Glu Leu Lys Arg Thr Val
370                 375                 380

Ala Ala Pro Ser Val Phe Ile Phe Pro Pro Ser Asp Glu Gln Leu Lys
385                 390                 395                 400

Ser Gly Thr Ala Ser Val Val Cys Leu Leu Asn Asn Phe Tyr Pro Arg
                405                 410                 415

Glu Ala Lys Val Gln Trp Lys Val Asp Asn Ala Leu Gln Ser Gly Asn
            420                 425                 430

Ser Gln Glu Ser Val Thr Glu Gln Asp Ser Lys Asp Ser Thr Tyr Ser
        435                 440                 445

Leu Ser Ser Thr Leu Thr Leu Ser Lys Ala Asp Tyr Glu Lys His Lys
450                 455                 460

Val Tyr Ala Cys Glu Val Thr His Gln Gly Leu Ser Ser Pro Val Thr
465                 470                 475                 480

Lys Ser Phe Asn Arg Gly Glu Cys
                485

<210> SEQ ID NO 19
<211> LENGTH: 2404
<212> TYPE: DNA
<213> ORGANISM: Artificial Sequence
<220> FEATURE:
<223> OTHER INFORMATION: VB6-845-CL-de-bouganin

<400> SEQUENCE: 19
gaattcctgc aggtctatgg aacgataaat gcccatgaaa attctatttc aaggagacag      60
tcataatgaa ataccttttg cctacggcag ccgctggatt gttattactc gctgcccaac     120
cagcgatggc gcaccatcat caccatcacg aagtacagct ggttcagtcc ggcccgggtc     180
ttgttcaacc gggtggttcc gttcgtatct cttgcgctgc ttctggttac acgttcacca     240
actacggcat gaactgggtc aaacaggctc cgggtaaagg cctggaatgg atgggctgga     300
tcaacaccta caccggtgaa ccacctacg ctgactcctt caaaggtcgc ttcactttct     360
ccctcgacac aagtgctagt gctgcatacc tccaaatcaa ctcgctgcgt gcagaggata     420
cagcagtcta ttactgcgcc cgtttcgcta tcaaaggtga ctactggggt caaggcacgc     480
tgctgaccgt ttcctcggct agcaccaaag gcccatcggt cttccccctg gcaccctcct     540
ccaagagcac ctctgggggc acagcggccc tgggctgcct ggtcaaggac tacttccccg     600
aaccggtgac ggtgtcgtgg aactcaggcg ccctgaccag cggcgtgcac accttcccgg     660
ctgtcctaca gtcctcagga ctctactccc tcagcagcgt ggtgaccgtg ccctccagca     720

```
gcttgggcac ccagacctac atctgcaacg tgaatcacaa gcccagcaac accaaggtgg    780
acaagaaagt tgagcccaaa tcttgttagt gatctagagt cgacctgcag gtctatggaa    840
cgataaatgc ccatgaaaat tctatttcaa ggagacagtc ataatgaaat acctattgcc    900
tacggcagcc gctggattgt tattactcgc tgcccaacca gcgatggcgg atatccagat    960
gacccagtcc ccgtcctccc tgagtgcttc tgttggtgac cgtgttacca tcacctgccg   1020
ttccaccaaa tccctcctgc actccaacgg tatcacctac ctttattggt atcaacagaa   1080
accgggtaaa gctccgaaac ttctgatcta ccagatgtcc aacctggctt ccggtgttcc   1140
gtctcgtttc tccagttctg gttctggtac cgacttcacc ctgaccatct cttctctgca   1200
gccggaagac ttcgctacct actactgcgc tcagaacctg gaaatcccgc gtaccttcgg   1260
tcagggtacc aaagttgaac ttaagcgcac tgtggctgca ccatctgtct tcatcttccc   1320
gccatctgat gagcagttga atctggaaac tgcctctgtt gtgtgcctgc tgaataactt   1380
ctatcccaga gaggccaaag tacagtggaa ggtggataac gccctccaat cgggtaactc   1440
ccaggagagt gtcacagagc aggacagcaa ggacagcacc tacagcctca gcagcaccct   1500
gacgctgagc aaagcagact acgagaaaca caaagtctac gcctgcgaag tcacccatca   1560
gggcctgagc tcgcccgtca caaagagctt caacagggga gagtgtacca ggcacaggca   1620
gcccagaggc tgggagcagc tctacaacac cgtgtcattt aaccttggag aagcttatga   1680
gtaccccact tttatacaag atttgcgcaa tgaattggct aagggcacac cagtatgtca   1740
acttccagtg acactacaaa ccatagccga tgacaagcga tttgttctag ttgatatcac   1800
tacgacctcg aagaaaacag ttaaggttgc tatagatgtg acagatgtgt atgttgtggg   1860
ttatcaagac aaatgggatg gcaaagatcg agctgttttc cttgacaagg ttcctactgt   1920
tgcaactagt aaactttttc cagggtgac taatcgtgta acgttaacat tgatggcag   1980
ctatcagaaa cttgtgaatg ctgccaaagc tgatagaaag gctctcgaac tgggggttaa   2040
caaattggaa ttttccattg aagcaatcca tggtaaaacg ataaatggtc aagaggcagc   2100
caagttcttt cttattgtca tccaaatggt ttcagaggca gctcggttca atatattga   2160
gactgaggtg gttgatagag gattatatgg atcattcaaa cctaatttta agtattgaa   2220
cttggagaac aattggggcg acatctctga tgccattcac aaatcatccc cacaatgtac   2280
cactattaat ccggcacttc agttgataag cccctcaaat gacccatggg ttgtaaataa   2340
agtgagtcaa attagtcccg atatgggtat ccttaagttt aaaagctcca aatagtagct   2400
cgag                                                                2404
```

<210> SEQ ID NO 20
<211> LENGTH: 750
<212> TYPE: PRT
<213> ORGANISM: Artificial Sequence
<220> FEATURE:
<223> OTHER INFORMATION: VB6-845-CL-de-bouganin

<400> SEQUENCE: 20

Met Lys Tyr Leu Leu Pro Thr Ala Ala Gly Leu Leu Leu Leu Ala
1               5                   10                  15

Ala Gln Pro Ala Met Ala His His His His His His Glu Val Gln Leu
                20                  25                  30

Val Gln Ser Gly Pro Gly Leu Val Gln Pro Gly Gly Ser Val Arg Ile
            35                  40                  45

Ser Cys Ala Ala Ser Gly Tyr Thr Phe Thr Asn Tyr Gly Met Asn Trp
        50                  55                  60

```
Val Lys Gln Ala Pro Gly Lys Gly Leu Glu Trp Met Gly Trp Ile Asn
 65                  70                  75                  80

Thr Tyr Thr Gly Glu Ser Thr Tyr Ala Asp Ser Phe Lys Gly Arg Phe
                 85                  90                  95

Thr Phe Ser Leu Asp Thr Ser Ala Ser Ala Ala Tyr Leu Gln Ile Asn
            100                 105                 110

Ser Leu Arg Ala Glu Asp Thr Ala Val Tyr Tyr Cys Ala Arg Phe Ala
        115                 120                 125

Ile Lys Gly Asp Tyr Trp Gly Gln Gly Thr Leu Leu Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Met Lys Tyr Leu Leu Pro Thr Ala Ala
                245                 250                 255

Ala Gly Leu Leu Leu Leu Ala Ala Gln Pro Ala Met Ala Asp Ile Gln
            260                 265                 270

Met Thr Gln Ser Pro Ser Ser Leu Ser Ala Ser Val Gly Asp Arg Val
        275                 280                 285

Thr Ile Thr Cys Arg Ser Thr Lys Ser Leu Leu His Ser Asn Gly Ile
    290                 295                 300

Thr Tyr Leu Tyr Trp Tyr Gln Gln Lys Pro Gly Lys Ala Pro Lys Leu
305                 310                 315                 320

Leu Ile Tyr Gln Met Ser Asn Leu Ala Ser Gly Val Pro Ser Arg Phe
                325                 330                 335

Ser Ser Ser Gly Ser Gly Thr Asp Phe Thr Leu Thr Ile Ser Ser Leu
            340                 345                 350

Gln Pro Glu Asp Phe Ala Thr Tyr Tyr Cys Ala Gln Asn Leu Glu Ile
        355                 360                 365

Pro Arg Thr Phe Gly Gln Gly Thr Lys Val Glu Leu Lys Arg Thr Val
    370                 375                 380

Ala Ala Pro Ser Val Phe Ile Phe Pro Pro Ser Asp Glu Gln Leu Lys
385                 390                 395                 400

Ser Gly Thr Ala Ser Val Val Cys Leu Leu Asn Asn Phe Tyr Pro Arg
                405                 410                 415

Glu Ala Lys Val Gln Trp Lys Val Asp Asn Ala Leu Gln Ser Gly Asn
            420                 425                 430

Ser Gln Glu Ser Val Thr Glu Gln Asp Ser Lys Asp Ser Thr Tyr Ser
        435                 440                 445

Leu Ser Ser Thr Leu Thr Leu Ser Lys Ala Asp Tyr Glu Lys His Lys
    450                 455                 460

Val Tyr Ala Cys Glu Val Thr His Gln Gly Leu Ser Ser Pro Val Thr
465                 470                 475                 480
```

```
Lys Ser Phe Asn Arg Gly Glu Cys Thr Arg His Arg Gln Pro Arg Gly
            485                 490                 495

Trp Glu Gln Leu Tyr Asn Thr Val Ser Phe Asn Leu Gly Glu Ala Tyr
            500                 505                 510

Glu Tyr Pro Thr Phe Ile Gln Asp Leu Arg Asn Glu Leu Ala Lys Gly
            515                 520                 525

Thr Pro Val Cys Gln Leu Pro Val Thr Leu Gln Thr Ile Ala Asp Asp
            530                 535                 540

Lys Arg Phe Val Leu Val Asp Ile Thr Thr Thr Ser Lys Lys Thr Val
545                 550                 555                 560

Lys Val Ala Ile Asp Val Thr Asp Val Tyr Val Val Gly Tyr Gln Asp
            565                 570                 575

Lys Trp Asp Gly Lys Asp Arg Ala Val Phe Leu Asp Lys Val Pro Thr
            580                 585                 590

Val Ala Thr Ser Lys Leu Phe Pro Gly Val Thr Asn Arg Val Thr Leu
            595                 600                 605

Thr Phe Asp Gly Ser Tyr Gln Lys Leu Val Asn Ala Ala Lys Ala Asp
            610                 615                 620

Arg Lys Ala Leu Glu Leu Gly Val Asn Lys Leu Glu Phe Ser Ile Glu
625                 630                 635                 640

Ala Ile His Gly Lys Thr Ile Asn Gly Gln Glu Ala Ala Lys Phe Phe
            645                 650                 655

Leu Ile Val Ile Gln Met Val Ser Glu Ala Ala Arg Phe Lys Tyr Ile
            660                 665                 670

Glu Thr Glu Val Val Asp Arg Gly Leu Tyr Gly Ser Phe Lys Pro Asn
            675                 680                 685

Phe Lys Val Leu Asn Leu Glu Asn Asn Trp Gly Asp Ile Ser Asp Ala
            690                 695                 700

Ile His Lys Ser Ser Pro Gln Cys Thr Thr Ile Asn Pro Ala Leu Gln
705                 710                 715                 720

Leu Ile Ser Pro Ser Asn Asp Pro Trp Val Val Asn Lys Val Ser Gln
            725                 730                 735

Ile Ser Pro Asp Met Gly Ile Leu Lys Phe Lys Ser Ser Lys
            740                 745                 750
```

<210> SEQ ID NO 21
<211> LENGTH: 2404
<212> TYPE: DNA
<213> ORGANISM: Artificial Sequence
<220> FEATURE:
<223> OTHER INFORMATION: VB6-845-NVH-de-bouganin

<400> SEQUENCE: 21

```
gaattcctgc aggtctatgg aacgataaat gcccatgaaa attctatttc aaggagacag    60
tcataatgaa ataccattg cctacggcag ccgctggatt gttattactc gctgcccaac    120
cagcgatggc gtacaacacc gtgtcattta accttggaga agcttatgag taccccactt    180
ttatacaaga tttgcgcaat gaattggcta agggcacacc agtatgtcaa cttccagtga    240
cactacaaac catagccgat gacaagcgat tgttctagt tgatatcact acgacctcga    300
agaaaacagt taaggttgct atagatgtga cagatgtgta tgttgtgggt tatcaagaca    360
aatgggatgg caaagatcga gctgtttcc ttgacaaggt tcctactgtt gcaactagta    420
aactttccc aggggtgact aatcgtgtaa cgttaacatt tgatggcagc tatcagaaac    480
ttgtgaatgc tgccaaagct gatagaaagg ctctcgaact gggggttaac aaattggaat    540
```

```
tttccattga agcaatccat ggtaaaacga taaatggtca agaggcagcc aagttctttc    600
ttattgtcat ccaaatggtt tcagaggcag ctcggttcaa atatattgag actgaggtgg    660
ttgatagagg attatatgga tcattcaaac ctaattttaa agtattgaac ttggagaaca    720
attggggcga catctctgat gccattcaca aatcatcccc acaatgtacc actattaatc    780
cggcacttca gttgataagc ccctcaaatg acccatgggt tgtaaataaa gtgagtcaaa    840
ttagtcccga tatgggtatc cttaagttta aaagctccaa aaccaggcac aggcagccca    900
gaggctggga gcagctcgaa gtacagctgg ttcagtccgg cccgggtctt gttcaaccgg    960
gtggttccgt tcgtatctct tgcgctgctt ctggttacac gttcaccaac tacggcatga   1020
actgggtcaa acaggctccg ggtaaaggcc tggaatggat gggctggatc aacacctaca   1080
ccggtgaatc cacctacgct gactccttca aggtcgctt cactttctcc ctcgacacaa    1140
gtgctagtgc tgcataccte caaatcaact cgctgcgtgc agaggataca gcagtctatt   1200
actgcgcccg tttcgctatc aaaggtgact actggggtca aggcacgctg ctgaccgttt   1260
cctcggctag caccaaaggc ccatcggtct tccccctggc accctcctcc aagagcacct   1320
ctgggggcac agcggccctg ggctgcctgg tcaaggacta cttccccgaa ccggtgacgg   1380
tgtcgtggaa ctcaggcgcc ctgaccagcg gcgtgcacac cttcccggct gtcctacagt   1440
cctcaggact ctactccctc agcagcgtgg tgaccgtgcc ctccagcagc ttgggcaccc   1500
agacctacat ctgcaacgtg aatcacaagc ccagcaacac caaggtggac aagaaagttg   1560
agcccaaatc ttgttagtga tctagagtcg acctgcaggt ctatggaacg ataaatgccc   1620
atgaaaattc tatttcaagg agacagtcat aatgaaatac ctattgccta cggcagccgc   1680
tggattgtta ttactcgctg cccaaccagc gatggcgcac catcatcacc atcacgatat   1740
ccagatgacc cagtccccgt cctccctgag tgcttctgtt ggtgaccgtg ttaccatcac   1800
ctgccgttcc accaaatccc tcctgcactc caacggtatc acctaccttt attggtatca   1860
acagaaaccg ggtaaagctc cgaaacttct gatctaccag atgtccaacc tggcttccgg   1920
tgttccgtct cgtttctcca gttctggttc tggtaccgac ttcaccctga ccatctcttc   1980
tctgcagccg aagacttcg ctacctacta ctgcgctcag aacctggaaa tcccgcgtac   2040
cttcggtcag ggtaccaaag ttgaacttaa gcgcactgtg gctgcaccat ctgtcttcat   2100
cttcccgcca tctgatgagc agttgaaatc tggaactgcc tctgttgtgt gcctgctgaa   2160
taacttctat cccagagagg ccaaagtaca gtggaaggtg gataacgccc tccaatcggg   2220
taactcccag gagagtgtca cagagcagga cagcaaggac agcacctaca gcctcagcag   2280
caccctgacg ctgagcaaag cagactacga gaaacacaaa gtctacgcct gcgaagtcac   2340
ccatcagggc ctgagctcgc ccgtcacaaa gagcttcaac ggggagagt gttagtagct   2400
cgag                                                                2404
```

<210> SEQ ID NO 22
<211> LENGTH: 750
<212> TYPE: PRT
<213> ORGANISM: Artificial Sequence
<220> FEATURE:
<223> OTHER INFORMATION: VB6-845-NVH-de-bouganin

<400> SEQUENCE: 22

```
Met Lys Tyr Leu Leu Pro Thr Ala Ala Ala Gly Leu Leu Leu Leu Ala
1               5                   10                  15

Ala Gln Pro Ala Met Ala Tyr Asn Thr Val Ser Phe Asn Leu Gly Glu
            20                  25                  30
```

-continued

Ala Tyr Glu Tyr Pro Thr Phe Ile Gln Asp Leu Arg Asn Glu Leu Ala
         35                  40                  45

Lys Gly Thr Pro Val Cys Gln Leu Pro Val Thr Leu Gln Thr Ile Ala
 50                  55                  60

Asp Asp Lys Arg Phe Val Leu Val Asp Ile Thr Thr Ser Lys Lys
 65                  70                  75                  80

Thr Val Lys Val Ala Ile Asp Val Thr Asp Val Tyr Val Val Gly Tyr
                 85                  90                  95

Gln Asp Lys Trp Asp Gly Lys Asp Arg Ala Val Phe Leu Asp Lys Val
             100                 105                 110

Pro Thr Val Ala Thr Ser Lys Leu Phe Pro Gly Val Thr Asn Arg Val
             115                 120                 125

Thr Leu Thr Phe Asp Gly Ser Tyr Gln Lys Leu Val Asn Ala Ala Lys
         130                 135                 140

Ala Asp Arg Lys Ala Leu Glu Leu Gly Val Asn Lys Leu Glu Phe Ser
145                 150                 155                 160

Ile Glu Ala Ile His Gly Lys Thr Ile Asn Gly Gln Glu Ala Ala Lys
                 165                 170                 175

Phe Phe Leu Ile Val Ile Gln Met Val Ser Glu Ala Ala Arg Phe Lys
             180                 185                 190

Tyr Ile Glu Thr Glu Val Val Asp Arg Gly Leu Tyr Gly Ser Phe Lys
         195                 200                 205

Pro Asn Phe Lys Val Leu Asn Leu Glu Asn Asn Trp Gly Asp Ile Ser
     210                 215                 220

Asp Ala Ile His Lys Ser Ser Pro Gln Cys Thr Thr Ile Asn Pro Ala
225                 230                 235                 240

Leu Gln Leu Ile Ser Pro Ser Asn Asp Pro Trp Val Val Asn Lys Val
                 245                 250                 255

Ser Gln Ile Ser Pro Asp Met Gly Ile Leu Lys Phe Lys Ser Ser Lys
             260                 265                 270

Thr Arg His Arg Gln Pro Arg Gly Trp Glu Gln Leu Glu Val Gln Leu
         275                 280                 285

Val Gln Ser Gly Pro Gly Leu Val Gln Pro Gly Gly Ser Val Arg Ile
     290                 295                 300

Ser Cys Ala Ala Ser Gly Tyr Thr Phe Thr Asn Tyr Gly Met Asn Trp
305                 310                 315                 320

Val Lys Gln Ala Pro Gly Lys Gly Leu Glu Trp Met Gly Trp Ile Asn
                 325                 330                 335

Thr Tyr Thr Gly Glu Ser Thr Tyr Ala Asp Ser Phe Lys Gly Arg Phe
             340                 345                 350

Thr Phe Ser Leu Asp Thr Ser Ala Ser Ala Ala Tyr Leu Gln Ile Asn
         355                 360                 365

Ser Leu Arg Ala Glu Asp Thr Ala Val Tyr Tyr Cys Ala Arg Phe Ala
     370                 375                 380

Ile Lys Gly Asp Tyr Trp Gly Gln Gly Thr Leu Leu Thr Val Ser Ser
385                 390                 395                 400

Ala Ser Thr Lys Gly Pro Ser Val Phe Pro Leu Ala Pro Ser Ser Lys
                 405                 410                 415

Ser Thr Ser Gly Gly Thr Ala Ala Leu Gly Cys Leu Val Lys Asp Tyr
             420                 425                 430

Phe Pro Glu Pro Val Thr Val Ser Trp Asn Ser Gly Ala Leu Thr Ser
         435                 440                 445

```
Gly Val His Thr Phe Pro Ala Val Leu Gln Ser Ser Gly Leu Tyr Ser
        450                 455                 460

Leu Ser Ser Val Val Thr Val Pro Ser Ser Leu Gly Thr Gln Thr
465                 470                 475                 480

Tyr Ile Cys Asn Val Asn His Lys Pro Ser Asn Thr Lys Val Asp Lys
                485                 490                 495

Lys Val Glu Pro Lys Ser Cys Met Lys Tyr Leu Leu Pro Thr Ala Ala
            500                 505                 510

Ala Gly Leu Leu Leu Leu Ala Ala Gln Pro Ala Met Ala His His His
        515                 520                 525

His His His Asp Ile Gln Met Thr Gln Ser Pro Ser Ser Leu Ser Ala
530                 535                 540

Ser Val Gly Asp Arg Val Thr Ile Thr Cys Arg Ser Thr Lys Ser Leu
545                 550                 555                 560

Leu His Ser Asn Gly Ile Thr Tyr Leu Tyr Trp Tyr Gln Gln Lys Pro
                565                 570                 575

Gly Lys Ala Pro Lys Leu Leu Ile Tyr Gln Met Ser Asn Leu Ala Ser
            580                 585                 590

Gly Val Pro Ser Arg Phe Ser Ser Gly Ser Gly Thr Asp Phe Thr
        595                 600                 605

Leu Thr Ile Ser Ser Leu Gln Pro Glu Asp Phe Ala Thr Tyr Tyr Cys
        610                 615                 620

Ala Gln Asn Leu Glu Ile Pro Arg Thr Phe Gly Gln Gly Thr Lys Val
625                 630                 635                 640

Glu Leu Lys Arg Thr Val Ala Ala Pro Ser Val Phe Ile Phe Pro Pro
                645                 650                 655

Ser Asp Glu Gln Leu Lys Ser Gly Thr Ala Ser Val Val Cys Leu Leu
            660                 665                 670

Asn Asn Phe Tyr Pro Arg Glu Ala Lys Val Gln Trp Lys Val Asp Asn
        675                 680                 685

Ala Leu Gln Ser Gly Asn Ser Gln Glu Ser Val Thr Glu Gln Asp Ser
        690                 695                 700

Lys Asp Ser Thr Tyr Ser Leu Ser Ser Thr Leu Thr Leu Ser Lys Ala
705                 710                 715                 720

Asp Tyr Glu Lys His Lys Val Tyr Ala Cys Glu Val Thr His Gln Gly
                725                 730                 735

Leu Ser Ser Pro Val Thr Lys Ser Phe Asn Arg Gly Glu Cys
            740                 745                 750

<210> SEQ ID NO 23
<211> LENGTH: 2404
<212> TYPE: DNA
<213> ORGANISM: Artificial Sequence
<220> FEATURE:
<223> OTHER INFORMATION: VB6-845-NVL-de-bouganin

<400> SEQUENCE: 23
gaattcctgc aggtctatgg aacgataaat gcccatgaaa attctatttc aaggagacag      60
tcataatgaa ataccattg cctacggcag ccgctggatt gttattactc gctgcccaac     120
cagcgatggc gcaccatcat caccatcacg aagtacagct ggttcagtcc ggcccgggtc     180
ttgttcaacc gggtggttcc gttcgtatct cttcgctgc ttctggttac acgttccacca    240 actacggcat gaactgggtc aaacaggctc cgggtaaagg cctggaatgg atgggctgga    300
tcaacaccta caccggtgaa ccacctacg ctgactcctt caaaggtcgc ttcactttct     360
```

| | |
|---|---|
| ccctcgacac aagtgctagt gctgcatacc tccaaatcaa ctcgctgcgt gcagaggata | 420 |
| cagcagtcta ttactgcgcc cgtttcgcta tcaaaggtga ctactggggt caaggcacgc | 480 |
| tgctgaccgt ttcctcggct agcaccaaag gcccatcggt cttccccctg cacctcct | 540 |
| ccaagagcac ctctgggggc acagcggccc tgggctgcct ggtcaaggac tacttcccccg | 600 |
| aaccggtgac ggtgtcgtgg aactcaggcg ccctgaccag cggcgtgcac accttcccgg | 660 |
| ctgtcctaca gtcctcagga ctctactccc tcagcagcgt ggtgaccgtg ccctccagca | 720 |
| gcttgggcac ccagacctac atctgcaacg tgaatcacaa gcccagcaac accaaggtgg | 780 |
| acaagaaagt tgagcccaaa tcttgttagt gatctagagt cgacctgcag gtctatggaa | 840 |
| cgataaatgc ccatgaaaat tctatttcaa ggagacagtc ataatgaaat acctattgcc | 900 |
| tacggcagcc gctggattgt tattactcgc tgcccaacca gcgatggcgt acaacaccgt | 960 |
| gtcatttaac cttggagaag cttatgagta ccccactttt atacaagatt gcgcaatga | 1020 |
| attggctaag gcacaccag tatgtcaact ccagtgaca ctacaaacca tagccgatga | 1080 |
| caagcgattt gttctagttg atatcactac gacctcgaag aaaacagtta aggttgctat | 1140 |
| agatgtgaca gatgtgtatg ttgtgggtta tcaagacaaa tgggatggca agatcgagc | 1200 |
| tgttttcctt gacaaggttc ctactgttgc aactagtaaa cttttcccag ggtgactaa | 1260 |
| tcgtgtaacg ttaacatttg atggcagcta tcagaaactt gtgaatgctg ccaaagctga | 1320 |
| tagaaaggct ctcgaactgg gggttaacaa attggaattt ccattgaag caatccatgg | 1380 |
| taaaacgata aatggtcaag aggcagccaa gttcttcct attgtcatcc aaatggtttc | 1440 |
| agaggcagct cggttcaaat atattgagac tgaggtggtt gatagaggat tatatggatc | 1500 |
| attcaaacct aattttaaag tattgaactt ggagaacaat tggggcgaca tctctgatgc | 1560 |
| cattcacaaa tcatccccac aatgtaccac tattaatccg gcacttcagt tgataagccc | 1620 |
| ctcaaatgac ccatgggttg taaataaagt gagtcaaatt agtccgata tgggtatcct | 1680 |
| taagtttaaa agctccaaaa ccaggcacag gcagcccaga ggctgggagc agctcgatat | 1740 |
| ccagatgacc cagtccccgt cctccctgag tgcttctgtt ggtgaccgtg ttaccatcac | 1800 |
| ctgccgttcc accaaatccc tcctgcactc caacggtatc acctaccttt attggtatca | 1860 |
| acagaaaccg ggtaaagctc cgaaacttct gatctaccag atgtccaacc tggcttccgg | 1920 |
| tgttccgtct cgtttctcca gttctggttc tggtaccgac ttcaccctga ccatctcttc | 1980 |
| tctgcagccg gaagacttcg ctacctacta ctgcgctcag aacctggaaa tcccgcgtac | 2040 |
| cttcggtcag ggtaccaaag ttgaacttaa gcgcactgtg gctgcaccat ctgtcttcat | 2100 |
| cttcccgcca tctgatgagc agttgaaatc tggaactgcc tctgttgtgt gcctgctgaa | 2160 |
| taacttctat cccagagagg ccaaagtaca gtggaaggtg gataacgccc tccaatcggg | 2220 |
| taactcccag gagagtgtca cagagcagga cagcaaggac agcacctaca gcctcagcag | 2280 |
| cacccctgacg ctgagcaaag cagactacga gaaacacaaa gtctacgcct gcgaagtcac | 2340 |
| ccatcagggc ctgagctcgc ccgtcacaaa gagcttcaac aggggagagt gttagtagct | 2400 |
| cgag | 2404 |

<210> SEQ ID NO 24
<211> LENGTH: 750
<212> TYPE: PRT
<213> ORGANISM: Artificial Sequence
<220> FEATURE:
<223> OTHER INFORMATION: VB6-845-NVL-de-bouganin

<400> SEQUENCE: 24

-continued

```
Met Lys Tyr Leu Leu Pro Thr Ala Ala Ala Gly Leu Leu Leu Ala
1               5                   10                  15

Ala Gln Pro Ala Met Ala His His His His His Glu Val Gln Leu
            20                  25                  30

Val Gln Ser Gly Pro Gly Leu Val Gln Pro Gly Gly Ser Val Arg Ile
        35                  40                  45

Ser Cys Ala Ala Ser Gly Tyr Thr Phe Thr Asn Tyr Gly Met Asn Trp
    50                  55                  60

Val Lys Gln Ala Pro Gly Lys Gly Leu Glu Trp Met Gly Trp Ile Asn
65                  70                  75                  80

Thr Tyr Thr Gly Glu Ser Thr Tyr Ala Asp Ser Phe Lys Gly Arg Phe
                85                  90                  95

Thr Phe Ser Leu Asp Thr Ser Ala Ser Ala Ala Tyr Leu Gln Ile Asn
            100                 105                 110

Ser Leu Arg Ala Glu Asp Thr Ala Val Tyr Tyr Cys Ala Arg Phe Ala
        115                 120                 125

Ile Lys Gly Asp Tyr Trp Gly Gln Gly Thr Leu Leu Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Met Lys Tyr Leu Leu Pro Thr Ala Ala
                245                 250                 255

Ala Gly Leu Leu Leu Leu Ala Ala Gln Pro Ala Met Ala Tyr Asn Thr
            260                 265                 270

Val Ser Phe Asn Leu Gly Glu Ala Tyr Glu Tyr Pro Thr Phe Ile Gln
        275                 280                 285

Asp Leu Arg Asn Glu Leu Ala Lys Gly Thr Pro Val Cys Gln Leu Pro
    290                 295                 300

Val Thr Leu Gln Thr Ile Ala Asp Asp Lys Arg Phe Val Leu Val Asp
305                 310                 315                 320

Ile Thr Thr Thr Ser Lys Lys Thr Val Lys Val Ala Ile Asp Val Thr
                325                 330                 335

Asp Val Tyr Val Val Gly Tyr Gln Asp Lys Trp Asp Gly Lys Asp Arg
            340                 345                 350

Ala Val Phe Leu Asp Lys Val Pro Thr Val Ala Thr Ser Lys Leu Phe
        355                 360                 365

Pro Gly Val Thr Asn Arg Val Thr Leu Thr Phe Asp Gly Ser Tyr Gln
    370                 375                 380

Lys Leu Val Asn Ala Ala Lys Ala Asp Arg Lys Ala Leu Glu Leu Gly
385                 390                 395                 400

Val Asn Lys Leu Glu Phe Ser Ile Glu Ala Ile His Gly Lys Thr Ile
                405                 410                 415
```

-continued

Asn Gly Gln Glu Ala Ala Lys Phe Phe Leu Ile Val Ile Gln Met Val
            420                 425                 430
Ser Glu Ala Ala Arg Phe Lys Tyr Ile Glu Thr Glu Val Val Asp Arg
        435                 440                 445
Gly Leu Tyr Gly Ser Phe Lys Pro Asn Phe Lys Val Leu Asn Leu Glu
    450                 455                 460
Asn Asn Trp Gly Asp Ile Ser Asp Ala Ile His Lys Ser Ser Pro Gln
465                 470                 475                 480
Cys Thr Thr Ile Asn Pro Ala Leu Gln Leu Ile Ser Pro Ser Asn Asp
                485                 490                 495
Pro Trp Val Val Asn Lys Val Ser Gln Ile Ser Pro Asp Met Gly Ile
            500                 505                 510
Leu Lys Phe Lys Ser Ser Lys Thr Arg His Arg Gln Pro Arg Gly Trp
        515                 520                 525
Glu Gln Leu Asp Ile Gln Met Thr Gln Ser Pro Ser Ser Leu Ser Ala
    530                 535                 540
Ser Val Gly Asp Arg Val Thr Ile Thr Cys Arg Ser Thr Lys Ser Leu
545                 550                 555                 560
Leu His Ser Asn Gly Ile Thr Tyr Leu Tyr Trp Tyr Gln Gln Lys Pro
                565                 570                 575
Gly Lys Ala Pro Lys Leu Leu Ile Tyr Gln Met Ser Asn Leu Ala Ser
            580                 585                 590
Gly Val Pro Ser Arg Phe Ser Ser Gly Ser Gly Thr Asp Phe Thr
        595                 600                 605
Leu Thr Ile Ser Ser Leu Gln Pro Glu Asp Phe Ala Thr Tyr Tyr Cys
    610                 615                 620
Ala Gln Asn Leu Glu Ile Pro Arg Thr Phe Gly Gln Gly Thr Lys Val
625                 630                 635                 640
Glu Leu Lys Arg Thr Val Ala Ala Pro Ser Val Phe Ile Phe Pro Pro
                645                 650                 655
Ser Asp Glu Gln Leu Lys Ser Gly Thr Ala Ser Val Val Cys Leu Leu
            660                 665                 670
Asn Asn Phe Tyr Pro Arg Glu Ala Lys Val Gln Trp Lys Val Asp Asn
        675                 680                 685
Ala Leu Gln Ser Gly Asn Ser Gln Glu Ser Val Thr Glu Gln Asp Ser
    690                 695                 700
Lys Asp Ser Thr Tyr Ser Leu Ser Ser Thr Leu Thr Leu Ser Lys Ala
705                 710                 715                 720
Asp Tyr Glu Lys His Lys Val Tyr Ala Cys Glu Val Thr His Gln Gly
                725                 730                 735
Leu Ser Pro Val Thr Lys Ser Phe Asn Arg Gly Glu Cys
            740                 745                 750

<210> SEQ ID NO 25
<211> LENGTH: 2407
<212> TYPE: DNA
<213> ORGANISM: Artificial Sequence
<220> FEATURE:
<223> OTHER INFORMATION: VB6-845-gelonin

<400> SEQUENCE: 25
gaattcctgc aggtctatgg aacgataaat gcccatgaaa attctatttc aaggagacag      60
tcataatgaa atacctattg cctacggcag ccgctggatt gttattactc gctgcccaac     120
cagcgatggc ggaagtacag ctggttcagt ccggcccggg tcttgttcaa ccgggtggtt     180

-continued

```
ccgttcgtat ctcttgcgct gcttctggtt acacgttcac caactacggc atgaactggg    240
tcaaacaggc tccgggtaaa ggcctggaat ggatgggctg atcaacacc tacaccggtg     300
aatccaccta cgctgactcc ttcaaaggtc gcttcacttt ctccctcgac acaagtgcta    360
gtgctgcata cctccaaatc aactcgctgc gtgcagagga tacagcagtc tattactgcg    420
cccgtttcgc tatcaaaggt gactactggg gtcaaggcac gctgctgacc gtttcctcgg    480
ctagcaccaa aggcccatcg gtcttccccc tggcaccctc ctccaagagc acctctgggg    540
gcacagcggc cctgggctgc ctggtcaagg actacttccc cgaaccggtg acggtgtcgt    600
ggaactcagg cgccctgacc agcggcgtgc acaccttccc ggctgtccta cagtcctcag    660
gactctactc cctcagcagc gtggtgaccg tgccctccag cagcttgggc acccagacct    720
acatctgcaa cgtgaatcac aagcccagca acaccaaggt ggacaagaaa gttgagccca    780
aatcttgtac caggcacagg cagcccagag gctgggagca gctcggcctg acaccgtga    840
gctttagcac taaaggtgcc acttatatta cctacgtgaa tttcttgaat gagctacgag    900
ttaaattgaa acccgaaggt aacagccatg gaatcccatt gctgcgcaaa aaatgtgatg    960
atcctggaaa gtgtttcgtt ttggtagcgc tttcaaatga caatgacag ttggcggaaa    1020
tagctataga tgttacaagt gtttatgtgg tgggctatca agtaagaaac agatcttact    1080
tctttaaaga tgctccagat gctgcttacg aaggcctctt caaaaacaca attaaaacaa    1140
gacttcattt tggcggcagc tatccctcgc tggaaggtga aaggcatat agagagacaa     1200
cagacttggg cattgaacca ttaaggattg gcatcaagaa acttgatgaa aatgcgatag    1260
acaattataa accaacggag atagctagtt ctctattggt tgttattcaa atggtgtctg    1320
aagcagctcg attcacccttt attgagaacc aaattagaaa taactttcaa cagagaatcc    1380
gcccgacgaa taatacaatc agccttgaga ataaatgggg taaactctcg ttccagatcc    1440
ggacatcagg tgcaaatgga atgttttcgg aggcagttga attggaacgt gcaaatggca    1500
aaaaatacta tgtcaccgca gttgatcaag taaaacccaa aatagcactc ttgaagttcg    1560
tcgataaaga tcctaaatag tgatctgag tcgacctgca ggtctatgga acgataaatg    1620
cccatgaaaa ttctatttca aggagacagt cataatgaaa tacctattgc ctacggcagc    1680
cgctggattg ttattactcg ctgcccaacc agcgatggcg caccatcatc accatcacga    1740
tatccagatg acccagtccc cgtcctccct gagtgcttct gttggtgacc gtgttaccat    1800
cacctgccgt tccaccaaat ccctcctgca ctccaacggt atcacctacc tttattggta    1860
tcaacagaaa ccgggtaaag ctccgaaact tctgatctac cagatgtcca acctggcttc    1920
cggtgttccg tctcgtttct ccagttctgg ttctggtacc gacttcaccc tgaccatctc    1980
ttctctgcag ccggaagact cgctacccta ctactgcgcg cagaacctgg aaatcccgcg    2040
taccttcggt cagggtacca agttgaact taagcgcact gtggctgcac catctgtctt    2100
catcttcccg ccatctgatg agcagttgaa atctggaact gcctctgttg tgtgcctgct    2160
gaataacttc tatcccagag aggccaaagt acagtggaag gtggataacg ccctccaatc    2220
gggtaactcc caggagagtg tcacagagca ggacagcaag gacagcacct acagcctcag    2280
cagcaccctg acgctgagca agcagacta cgagaaacac aaagtctacg cctgcgaagt    2340
cacccatcag ggcctgagct cgcccgtcac aaagagcttc aacaggggag agtgttagta    2400
gctcgag                                                              2407
```

<210> SEQ ID NO 26
<211> LENGTH: 751

-continued

<212> TYPE: PRT
<213> ORGANISM: Artificial Sequence
<220> FEATURE:
<223> OTHER INFORMATION: VB6-845-gelonin

<400> SEQUENCE: 26

```
Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Gln Ser Gly Pro Gly
            20                  25                  30

Leu Val Gln Pro Gly Gly Ser Val Arg Ile Ser Cys Ala Ala Ser Gly
        35                  40                  45

Tyr Thr Phe Thr Asn Tyr Gly Met Asn Trp Val Lys Gln Ala Pro Gly
    50                  55                  60

Lys Gly Leu Glu Trp Met Gly Trp Ile Asn Thr Tyr Thr Gly Glu Ser
65                  70                  75                  80

Thr Tyr Ala Asp Ser Phe Lys Gly Arg Phe Thr Phe Ser Leu Asp Thr
                85                  90                  95

Ser Ala Ser Ala Ala Tyr Leu Gln Ile Asn Ser Leu Arg Ala Glu Asp
            100                 105                 110

Thr Ala Val Tyr Tyr Cys Ala Arg Phe Ala Ile Lys Gly Asp Tyr Trp
        115                 120                 125

Gly Gln Gly Thr Leu Leu Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Thr Arg His Arg Gln Pro Arg Gly Trp Glu Gln Leu Gly Leu Asp
                245                 250                 255

Thr Val Ser Phe Ser Thr Lys Gly Ala Thr Tyr Ile Thr Tyr Val Asn
            260                 265                 270

Phe Leu Asn Glu Leu Arg Val Lys Leu Lys Pro Glu Gly Asn Ser His
        275                 280                 285

Gly Ile Pro Leu Leu Arg Lys Lys Cys Asp Asp Pro Gly Lys Cys Phe
    290                 295                 300

Val Leu Val Ala Leu Ser Asn Asp Asn Gly Gln Leu Ala Glu Ile Ala
305                 310                 315                 320

Ile Asp Val Thr Ser Val Tyr Val Val Gly Tyr Gln Val Arg Asn Arg
                325                 330                 335

Ser Tyr Phe Phe Lys Asp Ala Pro Asp Ala Ala Tyr Glu Gly Leu Phe
            340                 345                 350

Lys Asn Thr Ile Lys Thr Arg Leu His Phe Gly Gly Ser Tyr Pro Ser
        355                 360                 365

Leu Glu Gly Glu Lys Ala Tyr Arg Glu Thr Thr Asp Leu Gly Ile Glu
    370                 375                 380
```

```
Pro Leu Arg Ile Gly Ile Lys Lys Leu Asp Glu Asn Ala Ile Asp Asn
385                 390                 395                 400

Tyr Lys Pro Thr Glu Ile Ala Ser Ser Leu Leu Val Val Ile Gln Met
            405                 410                 415

Val Ser Glu Ala Ala Arg Phe Thr Phe Ile Glu Asn Gln Ile Arg Asn
        420                 425                 430

Asn Phe Gln Gln Arg Ile Arg Pro Thr Asn Asn Thr Ile Ser Leu Glu
    435                 440                 445

Asn Lys Trp Gly Lys Leu Ser Phe Gln Ile Arg Thr Ser Gly Ala Asn
450                 455                 460

Gly Met Phe Ser Glu Ala Val Glu Leu Glu Arg Ala Asn Gly Lys Lys
465                 470                 475                 480

Tyr Tyr Val Thr Ala Val Asp Gln Val Lys Pro Lys Ile Ala Leu Leu
            485                 490                 495

Lys Phe Val Asp Lys Asp Pro Lys Met Lys Tyr Leu Leu Pro Thr Ala
        500                 505                 510

Ala Ala Gly Leu Leu Leu Leu Ala Ala Gln Pro Ala Met Ala His His
    515                 520                 525

His His His His Asp Ile Gln Met Thr Gln Ser Pro Ser Ser Leu Ser
530                 535                 540

Ala Ser Val Gly Asp Arg Val Thr Ile Thr Cys Arg Ser Thr Lys Ser
545                 550                 555                 560

Leu Leu His Ser Asn Gly Ile Thr Tyr Leu Tyr Trp Tyr Gln Gln Lys
            565                 570                 575

Pro Gly Lys Ala Pro Lys Leu Leu Ile Tyr Gln Met Ser Asn Leu Ala
        580                 585                 590

Ser Gly Val Pro Ser Arg Phe Ser Ser Gly Ser Gly Thr Asp Phe
    595                 600                 605

Thr Leu Thr Ile Ser Ser Leu Gln Pro Glu Asp Phe Ala Thr Tyr Tyr
610                 615                 620

Cys Ala Gln Asn Leu Glu Ile Pro Arg Thr Phe Gly Gln Gly Thr Lys
625                 630                 635                 640

Val Glu Leu Lys Arg Thr Val Ala Ala Pro Ser Val Phe Ile Phe Pro
            645                 650                 655

Pro Ser Asp Glu Gln Leu Lys Ser Gly Thr Ala Ser Val Val Cys Leu
        660                 665                 670

Leu Asn Asn Phe Tyr Pro Arg Glu Ala Lys Val Gln Trp Lys Val Asp
    675                 680                 685

Asn Ala Leu Gln Ser Gly Asn Ser Gln Glu Ser Val Thr Glu Gln Asp
690                 695                 700

Ser Lys Asp Ser Thr Tyr Ser Leu Ser Ser Thr Leu Thr Leu Ser Lys
705                 710                 715                 720

Ala Asp Tyr Glu Lys His Lys Val Tyr Ala Cys Glu Val Thr His Gln
            725                 730                 735

Gly Leu Ser Ser Pro Val Thr Lys Ser Phe Asn Arg Gly Glu Cys
        740                 745                 750

<210> SEQ ID NO 27
<211> LENGTH: 2431
<212> TYPE: DNA
<213> ORGANISM: Artificial Sequence
<220> FEATURE:
<223> OTHER INFORMATION: VB6-011

<400> SEQUENCE: 27
```

-continued

```
gaattcctgc aggtctatgg aacgataaat gcccatgaaa attctatttc aaggagacag      60
tcataatgaa atacctattg cctacggcag ccgctggatt gttattactc gctgcccaac     120
cagcgatggc gcaggtgcag ctggtggagt ctggggagg cgtggtccag cctgggaggt      180
ccctgagact ctcctgtgca gcctctggat tccccttcag aagctttgct atgcactggg    240
tccgccaggc tctaggcaag gggctggagt ggtggcagt tatatcatat gatggaagca     300
ctaaatacta cgcagactcc gtgaagggcc gattcaccat ctccagagac acttccaaga    360
acacggtgta tctaaaaatg aacagcctga gaactgagga cacggctgtc tattactgtg    420
cgagagatca gagcctgttg ggtgactatg accactacta cggtttggac gtctggggca    480
aagggaccac ggtcacggtc tcttcagcta gcaccaaagg cccatcggtc ttccccctgg    540
caccctcctc caagagcacc tctggggca cagcggccct gggctgcctg gtcaaggact     600
acttccccga accggtgacg gtgtcgtgga actcaggcgc cctgaccagc ggcgtgcaca    660
ccttcccggc tgtcctacag tcctcaggac tctactccct cagcagcgtg gtgaccgtgc    720
cctccagcag cttgggcacc cagacctaca tctgcaacgt gaatcacaag cccagcaaca    780
ccaaggtgga caagaaagtt gagcccaaat cttgtaccag gcacaggcag cccagaggct    840
gggagcagct ctacaacacc gtgtcattta accttggaga agcttatgag tacccacctt    900
ttatacaaga tttgcgcaat gaattggcta agggcacacc agtatgtcaa cttccagtga    960
cactacaaac catagccgat gacaagcgat ttgttctagt tgatatcact acgacctcga   1020
agaaaacagt taaggttgct atagatgtga cagatgtgta tgttgtgggt tatcaagaca   1080
aatgggatgg caaagatcga gctgttttcc ttgacaaggt tcctactgtt gcaactagta   1140
aacttttccc aggggtgact aatcgtgtaa cgttaacatt tgatggcagc tatcagaaac   1200
ttgtgaatgc tgccaaagct gatagaaagg ctctcgaact gggggttaac aaattggaat   1260
tttccattga agcaatccat ggtaaaacga taaatggtca agaggcagcc aagttctttc   1320
ttattgtcat ccaaatggtt tcagaggcag ctcggttcaa atatattgag actgaggtgg   1380
ttgatagagg attatatgga tcattcaaac ctaattttaa agtattgaac ttggagaaca   1440
attggggcga catctctgat gccattcaca aatcatcccc acaatgtacc actattaatc   1500
cggcacttca gttgataagc ccctcaaatg acccatgggt tgtaaataaa gtgagtcaaa   1560
ttagtcccga tatgggtatc cttaagttta aaagctccaa atagtgatct agagtcgacc   1620
tgcaggtcta tggaacgata aatgcccatg aaaattctat ttcaaggaga cagtcataat   1680 gaaatacctta ttgcctacgg cagccgctgg attgttatta ctcgctgccc aaccagcgat   1740
ggcgcatcac catcaccatc acgatatcgt gttgacgcag tctccaggca ccctgtcttt   1800
gtctccaggg gaaagagcca ccctctcctg cagggccagt cagagtgtta gtagcagcta   1860
cttagcctgg taccagcaga aacctggcca ggctcccagg ctcctcatct atggtgcatc   1920
caccagggcc actggcatgc cagacaggtt cagtggcagt gggtccggga cagacttcac   1980
tctcaccatc agtagactgg agcctgaaga ttttgcagtg tattactgtc agcagtatgg   2040
tagctcacct cagacacctc agatcacttt cggcggaggg accaaggtgg agatcaaacg   2100
aactgtggct gcaccatctg tcttcatctt cccgccatct gatgagcagt tgaaatctgg   2160
aactgcctct gttgtgtgcc tgctgaataa cttctatccc agagaggcca agtacagtg    2220 gaaggtggat aacgccctcc aatcgggtaa ctcccaggag agtgtcacag agcaggacag   2280
caaggacagc acctacagcc tcagcagcac cctgacgctg agcaaagcag actacgagaa   2340
acacaaagtc tacgcctgcg aagtcaccca tcagggcctg agctcgcccg tcacaaagag   2400
```
cttcaacagg ggagagtgtt agtgactcga g 2431

<210> SEQ ID NO 28
<211> LENGTH: 759
<212> TYPE: PRT
<213> ORGANISM: Artificial Sequence
<220> FEATURE:
<223> OTHER INFORMATION: VB6-011

<400> SEQUENCE: 28

```
Met Lys Tyr Leu Leu Pro Thr Ala Ala Ala Gly Leu Leu Leu Leu Ala
 1               5                  10                  15

Ala Gln Pro Ala Met Ala Gln Val Gln Leu Val Glu Ser Gly Gly Gly
             20                  25                  30

Val Val Gln Pro Gly Arg Ser Leu Arg Leu Ser Cys Ala Ala Ser Gly
         35                  40                  45

Phe Pro Phe Arg Ser Phe Ala Met His Trp Val Arg Gln Ala Leu Gly
     50                  55                  60

Lys Gly Leu Glu Trp Val Ala Val Ile Ser Tyr Asp Gly Ser Thr Lys
 65                  70                  75                  80

Tyr Tyr Ala Asp Ser Val Lys Gly Arg Phe Thr Ile Ser Arg Asp Thr
                 85                  90                  95

Ser Lys Asn Thr Val Tyr Leu Lys Met Asn Ser Leu Arg Thr Glu Asp
            100                 105                 110

Thr Ala Val Tyr Tyr Cys Ala Arg Asp Gln Ser Leu Leu Gly Asp Tyr
        115                 120                 125

Asp His Tyr Tyr Gly Leu Asp Val Trp Gly Lys Gly Thr Thr Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Lys Val Glu Pro Lys Ser Cys Thr Arg His Arg Gln Pro
                245                 250                 255

Arg Gly Trp Glu Gln Leu Tyr Asn Thr Val Ser Phe Asn Leu Gly Glu
            260                 265                 270

Ala Tyr Glu Tyr Pro Thr Phe Ile Gln Asp Leu Arg Asn Glu Leu Ala
        275                 280                 285

Lys Gly Thr Pro Val Cys Gln Leu Pro Val Thr Leu Gln Thr Ile Ala
    290                 295                 300

Asp Asp Lys Arg Phe Val Leu Val Asp Ile Thr Thr Thr Ser Lys Lys
305                 310                 315                 320

Thr Val Lys Val Ala Ile Asp Val Thr Asp Val Tyr Val Val Gly Tyr
                325                 330                 335

Gln Asp Lys Trp Asp Gly Lys Asp Arg Ala Val Phe Leu Asp Lys Val
            340                 345                 350
```

-continued

```
Pro Thr Val Ala Thr Ser Lys Leu Phe Pro Gly Val Thr Asn Arg Val
        355                 360                 365
Thr Leu Thr Phe Asp Gly Ser Tyr Gln Lys Leu Val Asn Ala Ala Lys
    370                 375                 380
Ala Asp Arg Lys Ala Leu Glu Leu Gly Val Asn Lys Leu Glu Phe Ser
385                 390                 395                 400
Ile Glu Ala Ile His Gly Lys Thr Ile Asn Gly Gln Glu Ala Ala Lys
                405                 410                 415
Phe Phe Leu Ile Val Ile Gln Met Val Ser Glu Ala Ala Arg Phe Lys
            420                 425                 430
Tyr Ile Glu Thr Glu Val Val Asp Arg Gly Leu Tyr Gly Ser Phe Lys
        435                 440                 445
Pro Asn Phe Lys Val Leu Asn Leu Glu Asn Asn Trp Gly Asp Ile Ser
    450                 455                 460
Asp Ala Ile His Lys Ser Ser Pro Gln Cys Thr Thr Ile Asn Pro Ala
465                 470                 475                 480
Leu Gln Leu Ile Ser Pro Ser Asn Asp Pro Trp Val Val Asn Lys Val
                485                 490                 495
Ser Gln Ile Ser Pro Asp Met Gly Ile Leu Lys Phe Lys Ser Ser Lys
            500                 505                 510
Met Lys Tyr Leu Leu Pro Thr Ala Ala Ala Gly Leu Leu Leu Leu Ala
        515                 520                 525
Ala Gln Pro Ala Met Ala His His His His His Asp Ile Val Leu
    530                 535                 540
Thr Gln Ser Pro Gly Thr Leu Ser Leu Ser Pro Gly Glu Arg Ala Thr
545                 550                 555                 560
Leu Ser Cys Arg Ala Ser Gln Ser Val Ser Ser Ser Tyr Leu Ala Trp
                565                 570                 575
Tyr Gln Gln Lys Pro Gly Gln Ala Pro Arg Leu Leu Ile Tyr Gly Ala
            580                 585                 590
Ser Thr Arg Ala Thr Gly Met Pro Asp Arg Phe Ser Gly Ser Gly Ser
        595                 600                 605
Gly Thr Asp Phe Thr Leu Thr Ile Ser Arg Leu Glu Pro Glu Asp Phe
    610                 615                 620
Ala Val Tyr Tyr Cys Gln Gln Tyr Gly Ser Ser Pro Gln Thr Pro Gln
625                 630                 635                 640
Ile Thr Phe Gly Gly Gly Thr Lys Val Glu Ile Lys Arg Thr Val Ala
                645                 650                 655
Ala Pro Ser Val Phe Ile Phe Pro Pro Ser Asp Glu Gln Leu Lys Ser
            660                 665                 670
Gly Thr Ala Ser Val Val Cys Leu Leu Asn Asn Phe Tyr Pro Arg Glu
        675                 680                 685
Ala Lys Val Gln Trp Lys Val Asp Asn Ala Leu Gln Ser Gly Asn Ser
    690                 695                 700
Gln Glu Ser Val Thr Glu Gln Asp Ser Lys Asp Ser Thr Tyr Ser Leu
705                 710                 715                 720
Ser Ser Thr Leu Thr Leu Ser Lys Ala Asp Tyr Glu Lys His Lys Val
                725                 730                 735
Tyr Ala Cys Glu Val Thr His Gln Gly Leu Ser Ser Pro Val Thr Lys
            740                 745                 750
Ser Phe Asn Arg Gly Glu Cys
        755
```

```
<210> SEQ ID NO 29
<211> LENGTH: 15
<212> TYPE: PRT
<213> ORGANISM: Bougainvillea spectabilis

<400> SEQUENCE: 29

Ala Lys Ala Asp Arg Lys Ala Leu Glu Leu Gly Val Asn Lys Leu
1               5                   10                  15

<210> SEQ ID NO 30
<211> LENGTH: 15
<212> TYPE: PRT
<213> ORGANISM: Bougainvillea spectabilis

<400> SEQUENCE: 30

Leu Gly Val Asn Lys Leu Glu Phe Ser Ile Glu Ala Ile His Gly
1               5                   10                  15

<210> SEQ ID NO 31
<211> LENGTH: 15
<212> TYPE: PRT
<213> ORGANISM: Bougainvillea spectabilis

<400> SEQUENCE: 31

Asn Gly Gln Glu Ala Ala Lys Phe Phe Leu Ile Val Ile Gln Met
1               5                   10                  15

<210> SEQ ID NO 32
<211> LENGTH: 15
<212> TYPE: PRT
<213> ORGANISM: Bougainvillea spectabilis

<400> SEQUENCE: 32

Tyr Asn Thr Val Ser Phe Asn Leu Gly Glu Ala Tyr Glu Tyr Pro
1               5                   10                  15

<210> SEQ ID NO 33
<211> LENGTH: 15
<212> TYPE: PRT
<213> ORGANISM: Bougainvillea spectabilis

<400> SEQUENCE: 33

Val Ser Phe Asn Leu Gly Glu Ala Tyr Glu Tyr Pro Thr Phe Ile
1               5                   10                  15

<210> SEQ ID NO 34
<211> LENGTH: 15
<212> TYPE: PRT
<213> ORGANISM: Bougainvillea spectabilis

<400> SEQUENCE: 34

Asn Leu Gly Glu Ala Tyr Glu Tyr Pro Thr Phe Ile Gln Asp Leu
1               5                   10                  15

<210> SEQ ID NO 35
<211> LENGTH: 15
<212> TYPE: PRT
<213> ORGANISM: Bougainvillea spectabilis

<400> SEQUENCE: 35

Glu Ala Tyr Glu Tyr Pro Thr Phe Ile Gln Asp Leu Arg Asn Glu
1               5                   10                  15

<210> SEQ ID NO 36
<211> LENGTH: 15
```

```
<212> TYPE: PRT
<213> ORGANISM: Bougainvillea spectabilis

<400> SEQUENCE: 36

Glu Tyr Pro Thr Phe Ile Gln Asp Leu Arg Asn Glu Leu Ala Lys
1               5                   10                  15

<210> SEQ ID NO 37
<211> LENGTH: 15
<212> TYPE: PRT
<213> ORGANISM: Bougainvillea spectabilis

<400> SEQUENCE: 37

Thr Phe Ile Gln Asp Leu Arg Asn Glu Leu Ala Lys Gly Thr Pro
1               5                   10                  15

<210> SEQ ID NO 38
<211> LENGTH: 15
<212> TYPE: PRT
<213> ORGANISM: Bougainvillea spectabilis

<400> SEQUENCE: 38

Gln Asp Leu Arg Asn Glu Leu Ala Lys Gly Thr Pro Val Cys Gln
1               5                   10                  15

<210> SEQ ID NO 39
<211> LENGTH: 15
<212> TYPE: PRT
<213> ORGANISM: Bougainvillea spectabilis

<400> SEQUENCE: 39

Arg Asn Glu Leu Ala Lys Gly Thr Pro Val Cys Gln Leu Pro Val
1               5                   10                  15

<210> SEQ ID NO 40
<211> LENGTH: 15
<212> TYPE: PRT
<213> ORGANISM: Bougainvillea spectabilis

<400> SEQUENCE: 40

Leu Ala Lys Gly Thr Pro Val Cys Gln Leu Pro Val Thr Leu Gln
1               5                   10                  15

<210> SEQ ID NO 41
<211> LENGTH: 15
<212> TYPE: PRT
<213> ORGANISM: Bougainvillea spectabilis

<400> SEQUENCE: 41

Gly Thr Pro Val Cys Gln Leu Pro Val Thr Leu Gln Thr Ile Ala
1               5                   10                  15

<210> SEQ ID NO 42
<211> LENGTH: 15
<212> TYPE: PRT
<213> ORGANISM: Bougainvillea spectabilis

<400> SEQUENCE: 42

Val Cys Gln Leu Pro Val Thr Leu Gln Thr Ile Ala Asp Asp Lys
1               5                   10                  15

<210> SEQ ID NO 43
<211> LENGTH: 15
<212> TYPE: PRT
<213> ORGANISM: Bougainvillea spectabilis
```

-continued

<400> SEQUENCE: 43

Leu Pro Val Thr Leu Gln Thr Ile Ala Asp Asp Lys Arg Phe Val
1               5                   10                  15

<210> SEQ ID NO 44
<211> LENGTH: 15
<212> TYPE: PRT
<213> ORGANISM: Bougainvillea spectabilis

<400> SEQUENCE: 44

Thr Leu Gln Thr Ile Ala Asp Asp Lys Arg Phe Val Leu Val Asp
1               5                   10                  15

<210> SEQ ID NO 45
<211> LENGTH: 15
<212> TYPE: PRT
<213> ORGANISM: Bougainvillea spectabilis

<400> SEQUENCE: 45

Thr Ile Ala Asp Asp Lys Arg Phe Val Leu Val Asp Ile Thr Thr
1               5                   10                  15

<210> SEQ ID NO 46
<211> LENGTH: 15
<212> TYPE: PRT
<213> ORGANISM: Bougainvillea spectabilis

<400> SEQUENCE: 46

Asp Asp Lys Arg Phe Val Leu Val Asp Ile Thr Thr Thr Ser Lys
1               5                   10                  15

<210> SEQ ID NO 47
<211> LENGTH: 15
<212> TYPE: PRT
<213> ORGANISM: Bougainvillea spectabilis

<400> SEQUENCE: 47

Arg Phe Val Leu Val Asp Ile Thr Thr Thr Ser Lys Lys Thr Val
1               5                   10                  15

<210> SEQ ID NO 48
<211> LENGTH: 15
<212> TYPE: PRT
<213> ORGANISM: Bougainvillea spectabilis

<400> SEQUENCE: 48

Leu Val Asp Ile Thr Thr Thr Ser Lys Lys Thr Val Lys Val Ala
1               5                   10                  15

<210> SEQ ID NO 49
<211> LENGTH: 15
<212> TYPE: PRT
<213> ORGANISM: Bougainvillea spectabilis

<400> SEQUENCE: 49

Ile Thr Thr Thr Ser Lys Lys Thr Val Lys Val Ala Ile Asp Val
1               5                   10                  15

<210> SEQ ID NO 50
<211> LENGTH: 15
<212> TYPE: PRT
<213> ORGANISM: Bougainvillea spectabilis

<400> SEQUENCE: 50

-continued

Thr Ser Lys Lys Thr Val Lys Val Ala Ile Asp Val Thr Asp Val
1               5                   10                  15

<210> SEQ ID NO 51
<211> LENGTH: 15
<212> TYPE: PRT
<213> ORGANISM: Bougainvillea spectabilis

<400> SEQUENCE: 51

Lys Thr Val Lys Val Ala Ile Asp Val Thr Asp Val Tyr Val Val
1               5                   10                  15

<210> SEQ ID NO 52
<211> LENGTH: 15
<212> TYPE: PRT
<213> ORGANISM: Bougainvillea spectabilis

<400> SEQUENCE: 52

Lys Val Ala Ile Asp Val Thr Asp Val Tyr Val Val Gly Tyr Gln
1               5                   10                  15

<210> SEQ ID NO 53
<211> LENGTH: 15
<212> TYPE: PRT
<213> ORGANISM: Bougainvillea spectabilis

<400> SEQUENCE: 53

Ile Asp Val Thr Asp Val Tyr Val Val Gly Tyr Gln Asp Lys Trp
1               5                   10                  15

<210> SEQ ID NO 54
<211> LENGTH: 15
<212> TYPE: PRT
<213> ORGANISM: Bougainvillea spectabilis

<400> SEQUENCE: 54

Thr Asp Val Tyr Val Val Gly Tyr Gln Asp Lys Trp Asp Gly Lys
1               5                   10                  15

<210> SEQ ID NO 55
<211> LENGTH: 15
<212> TYPE: PRT
<213> ORGANISM: Bougainvillea spectabilis

<400> SEQUENCE: 55

Tyr Val Val Gly Tyr Gln Asp Lys Trp Asp Gly Lys Asp Arg Ala
1               5                   10                  15

<210> SEQ ID NO 56
<211> LENGTH: 15
<212> TYPE: PRT
<213> ORGANISM: Bougainvillea spectabilis

<400> SEQUENCE: 56

Gly Tyr Gln Asp Lys Trp Asp Gly Lys Asp Arg Ala Val Phe Leu
1               5                   10                  15

<210> SEQ ID NO 57
<211> LENGTH: 15
<212> TYPE: PRT
<213> ORGANISM: Bougainvillea spectabilis

<400> SEQUENCE: 57

Asp Lys Trp Asp Gly Lys Asp Arg Ala Val Phe Leu Asp Lys Val

```
                1               5                  10                 15
```

<210> SEQ ID NO 58
<211> LENGTH: 15
<212> TYPE: PRT
<213> ORGANISM: Bougainvillea spectabilis

<400> SEQUENCE: 58

Asp Gly Lys Asp Arg Ala Val Phe Leu Asp Lys Val Pro Thr Val
1               5                  10                 15

<210> SEQ ID NO 59
<211> LENGTH: 15
<212> TYPE: PRT
<213> ORGANISM: Bougainvillea spectabilis

<400> SEQUENCE: 59

Asp Arg Ala Val Phe Leu Asp Lys Val Pro Thr Val Ala Thr Ser
1               5                  10                 15

<210> SEQ ID NO 60
<211> LENGTH: 15
<212> TYPE: PRT
<213> ORGANISM: Bougainvillea spectabilis

<400> SEQUENCE: 60

Val Phe Leu Asp Lys Val Pro Thr Val Ala Thr Ser Lys Leu Phe
1               5                  10                 15

<210> SEQ ID NO 61
<211> LENGTH: 15
<212> TYPE: PRT
<213> ORGANISM: Bougainvillea spectabilis

<400> SEQUENCE: 61

Asp Lys Val Pro Thr Val Ala Thr Ser Lys Leu Phe Pro Gly Val
1               5                  10                 15

<210> SEQ ID NO 62
<211> LENGTH: 15
<212> TYPE: PRT
<213> ORGANISM: Bougainvillea spectabilis

<400> SEQUENCE: 62

Pro Thr Val Ala Thr Ser Lys Leu Phe Pro Gly Val Thr Asn Arg
1               5                  10                 15

<210> SEQ ID NO 63
<211> LENGTH: 15
<212> TYPE: PRT
<213> ORGANISM: Bougainvillea spectabilis

<400> SEQUENCE: 63

Ala Thr Ser Lys Leu Phe Pro Gly Val Thr Asn Arg Val Thr Leu
1               5                  10                 15

<210> SEQ ID NO 64
<211> LENGTH: 15
<212> TYPE: PRT
<213> ORGANISM: Bougainvillea spectabilis

<400> SEQUENCE: 64

Lys Leu Phe Pro Gly Val Thr Asn Arg Val Thr Leu Thr Phe Asp
1               5                  10                 15

```
<210> SEQ ID NO 65
<211> LENGTH: 15
<212> TYPE: PRT
<213> ORGANISM: Bougainvillea spectabilis

<400> SEQUENCE: 65

Pro Gly Val Thr Asn Arg Val Thr Leu Thr Phe Asp Gly Ser Tyr
1               5                   10                  15

<210> SEQ ID NO 66
<211> LENGTH: 15
<212> TYPE: PRT
<213> ORGANISM: Bougainvillea spectabilis

<400> SEQUENCE: 66

Thr Asn Arg Val Thr Leu Thr Phe Asp Gly Ser Tyr Gln Lys Leu
1               5                   10                  15

<210> SEQ ID NO 67
<211> LENGTH: 15
<212> TYPE: PRT
<213> ORGANISM: Bougainvillea spectabilis

<400> SEQUENCE: 67

Val Thr Leu Thr Phe Asp Gly Ser Tyr Gln Lys Leu Val Asn Ala
1               5                   10                  15

<210> SEQ ID NO 68
<211> LENGTH: 15
<212> TYPE: PRT
<213> ORGANISM: Bougainvillea spectabilis

<400> SEQUENCE: 68

Thr Phe Asp Gly Ser Tyr Gln Lys Leu Val Asn Ala Ala Lys Val
1               5                   10                  15

<210> SEQ ID NO 69
<211> LENGTH: 15
<212> TYPE: PRT
<213> ORGANISM: Bougainvillea spectabilis

<400> SEQUENCE: 69

Gly Ser Tyr Gln Lys Leu Val Asn Ala Ala Lys Val Asp Arg Lys
1               5                   10                  15

<210> SEQ ID NO 70
<211> LENGTH: 15
<212> TYPE: PRT
<213> ORGANISM: Bougainvillea spectabilis

<400> SEQUENCE: 70

Gln Lys Leu Val Asn Ala Ala Lys Val Asp Arg Lys Asp Leu Glu
1               5                   10                  15

<210> SEQ ID NO 71
<211> LENGTH: 15
<212> TYPE: PRT
<213> ORGANISM: Bougainvillea spectabilis

<400> SEQUENCE: 71

Val Asn Ala Ala Lys Val Asp Arg Lys Asp Leu Glu Leu Gly Val
1               5                   10                  15

<210> SEQ ID NO 72
```

-continued

```
<211> LENGTH: 15
<212> TYPE: PRT
<213> ORGANISM: Bougainvillea spectabilis

<400> SEQUENCE: 72

Ala Lys Val Asp Arg Lys Asp Leu Glu Leu Gly Val Tyr Lys Leu
1               5                   10                  15

<210> SEQ ID NO 73
<211> LENGTH: 15
<212> TYPE: PRT
<213> ORGANISM: Bougainvillea spectabilis

<400> SEQUENCE: 73

Asp Arg Lys Asp Leu Glu Leu Gly Val Tyr Lys Leu Glu Phe Ser
1               5                   10                  15

<210> SEQ ID NO 74
<211> LENGTH: 15
<212> TYPE: PRT
<213> ORGANISM: Bougainvillea spectabilis

<400> SEQUENCE: 74

Asp Leu Glu Leu Gly Val Tyr Lys Leu Glu Phe Ser Ile Glu Ala
1               5                   10                  15

<210> SEQ ID NO 75
<211> LENGTH: 15
<212> TYPE: PRT
<213> ORGANISM: Bougainvillea spectabilis

<400> SEQUENCE: 75

Leu Gly Val Tyr Lys Leu Glu Phe Ser Ile Glu Ala Ile His Gly
1               5                   10                  15

<210> SEQ ID NO 76
<211> LENGTH: 15
<212> TYPE: PRT
<213> ORGANISM: Bougainvillea spectabilis

<400> SEQUENCE: 76

Tyr Lys Leu Glu Phe Ser Ile Glu Ala Ile His Gly Lys Thr Ile
1               5                   10                  15

<210> SEQ ID NO 77
<211> LENGTH: 15
<212> TYPE: PRT
<213> ORGANISM: Bougainvillea spectabilis

<400> SEQUENCE: 77

Glu Phe Ser Ile Glu Ala Ile His Gly Lys Thr Ile Asn Gly Gln
1               5                   10                  15

<210> SEQ ID NO 78
<211> LENGTH: 15
<212> TYPE: PRT
<213> ORGANISM: Bougainvillea spectabilis

<400> SEQUENCE: 78

Ile Glu Ala Ile His Gly Lys Thr Ile Asn Gly Gln Glu Ile Ala
1               5                   10                  15

<210> SEQ ID NO 79
<211> LENGTH: 15
<212> TYPE: PRT
```

<213> ORGANISM: Bougainvillea spectabilis

<400> SEQUENCE: 79

Ile His Gly Lys Thr Ile Asn Gly Gln Glu Ile Ala Lys Phe Phe
1               5                   10                  15

<210> SEQ ID NO 80
<211> LENGTH: 15
<212> TYPE: PRT
<213> ORGANISM: Bougainvillea spectabilis

<400> SEQUENCE: 80

Lys Thr Ile Asn Gly Gln Glu Ile Ala Lys Phe Phe Leu Ile Val
1               5                   10                  15

<210> SEQ ID NO 81
<211> LENGTH: 15
<212> TYPE: PRT
<213> ORGANISM: Bougainvillea spectabilis

<400> SEQUENCE: 81

Asn Gly Gln Glu Ile Ala Lys Phe Phe Leu Ile Val Ile Gln Met
1               5                   10                  15

<210> SEQ ID NO 82
<211> LENGTH: 15
<212> TYPE: PRT
<213> ORGANISM: Bougainvillea spectabilis

<400> SEQUENCE: 82

Glu Ile Ala Lys Phe Phe Leu Ile Val Ile Gln Met Val Ser Glu
1               5                   10                  15

<210> SEQ ID NO 83
<211> LENGTH: 15
<212> TYPE: PRT
<213> ORGANISM: Bougainvillea spectabilis

<400> SEQUENCE: 83

Lys Phe Phe Leu Ile Val Ile Gln Met Val Ser Glu Ala Ala Arg
1               5                   10                  15

<210> SEQ ID NO 84
<211> LENGTH: 15
<212> TYPE: PRT
<213> ORGANISM: Bougainvillea spectabilis

<400> SEQUENCE: 84

Leu Ile Val Ile Gln Met Val Ser Glu Ala Ala Arg Phe Lys Tyr
1               5                   10                  15

<210> SEQ ID NO 85
<211> LENGTH: 15
<212> TYPE: PRT
<213> ORGANISM: Bougainvillea spectabilis

<400> SEQUENCE: 85

Ile Gln Met Val Ser Glu Ala Ala Arg Phe Lys Tyr Ile Glu Thr
1               5                   10                  15

<210> SEQ ID NO 86
<211> LENGTH: 15
<212> TYPE: PRT
<213> ORGANISM: Bougainvillea spectabilis

```
<400> SEQUENCE: 86

Val Ser Glu Ala Ala Arg Phe Lys Tyr Ile Glu Thr Glu Val Val
1               5                   10                  15

<210> SEQ ID NO 87
<211> LENGTH: 15
<212> TYPE: PRT
<213> ORGANISM: Bougainvillea spectabilis

<400> SEQUENCE: 87

Ala Ala Arg Phe Lys Tyr Ile Glu Thr Glu Val Val Asp Arg Gly
1               5                   10                  15

<210> SEQ ID NO 88
<211> LENGTH: 15
<212> TYPE: PRT
<213> ORGANISM: Bougainvillea spectabilis

<400> SEQUENCE: 88

Phe Lys Tyr Ile Glu Thr Glu Val Val Asp Arg Gly Leu Tyr Gly
1               5                   10                  15

<210> SEQ ID NO 89
<211> LENGTH: 15
<212> TYPE: PRT
<213> ORGANISM: Bougainvillea spectabilis

<400> SEQUENCE: 89

Ile Glu Thr Glu Val Val Asp Arg Gly Leu Tyr Gly Ser Phe Lys
1               5                   10                  15

<210> SEQ ID NO 90
<211> LENGTH: 15
<212> TYPE: PRT
<213> ORGANISM: Bougainvillea spectabilis

<400> SEQUENCE: 90

Glu Val Val Asp Arg Gly Leu Tyr Gly Ser Phe Lys Pro Asn Phe
1               5                   10                  15

<210> SEQ ID NO 91
<211> LENGTH: 15
<212> TYPE: PRT
<213> ORGANISM: Bougainvillea spectabilis

<400> SEQUENCE: 91

Asp Arg Gly Leu Tyr Gly Ser Phe Lys Pro Asn Phe Lys Val Leu
1               5                   10                  15

<210> SEQ ID NO 92
<211> LENGTH: 15
<212> TYPE: PRT
<213> ORGANISM: Bougainvillea spectabilis

<400> SEQUENCE: 92

Leu Tyr Gly Ser Phe Lys Pro Asn Phe Lys Val Leu Asn Leu Glu
1               5                   10                  15

<210> SEQ ID NO 93
<211> LENGTH: 15
<212> TYPE: PRT
<213> ORGANISM: Bougainvillea spectabilis

<400> SEQUENCE: 93
```

-continued

```
Ser Phe Lys Pro Asn Phe Lys Val Leu Asn Leu Glu Asn Asn Trp
1               5                   10                  15

<210> SEQ ID NO 94
<211> LENGTH: 15
<212> TYPE: PRT
<213> ORGANISM: Bougainvillea spectabilis

<400> SEQUENCE: 94

Pro Asn Phe Lys Val Leu Asn Leu Glu Asn Asn Trp Gly Asp Ile
1               5                   10                  15

<210> SEQ ID NO 95
<211> LENGTH: 15
<212> TYPE: PRT
<213> ORGANISM: Bougainvillea spectabilis

<400> SEQUENCE: 95

Lys Val Leu Asn Leu Glu Asn Asn Trp Gly Asp Ile Ser Asp Ala
1               5                   10                  15

<210> SEQ ID NO 96
<211> LENGTH: 15
<212> TYPE: PRT
<213> ORGANISM: Bougainvillea spectabilis

<400> SEQUENCE: 96

Asn Leu Glu Asn Asn Trp Gly Asp Ile Ser Asp Ala Ile His Lys
1               5                   10                  15

<210> SEQ ID NO 97
<211> LENGTH: 15
<212> TYPE: PRT
<213> ORGANISM: Bougainvillea spectabilis

<400> SEQUENCE: 97

Asn Asn Trp Gly Asp Ile Ser Asp Ala Ile His Lys Ser Ser Pro
1               5                   10                  15

<210> SEQ ID NO 98
<211> LENGTH: 15
<212> TYPE: PRT
<213> ORGANISM: Bougainvillea spectabilis

<400> SEQUENCE: 98

Gly Asp Ile Ser Asp Ala Ile His Lys Ser Ser Pro Gln Cys Thr
1               5                   10                  15

<210> SEQ ID NO 99
<211> LENGTH: 15
<212> TYPE: PRT
<213> ORGANISM: Bougainvillea spectabilis

<400> SEQUENCE: 99

Ser Asp Ala Ile His Lys Ser Ser Pro Gln Cys Thr Thr Ile Asn
1               5                   10                  15

<210> SEQ ID NO 100
<211> LENGTH: 15
<212> TYPE: PRT
<213> ORGANISM: Bougainvillea spectabilis

<400> SEQUENCE: 100

Ile His Lys Ser Ser Pro Gln Cys Thr Thr Ile Asn Pro Ala Leu
1               5                   10                  15
```

```
<210> SEQ ID NO 101
<211> LENGTH: 15
<212> TYPE: PRT
<213> ORGANISM: Bougainvillea spectabilis

<400> SEQUENCE: 101

Ser Ser Pro Gln Cys Thr Thr Ile Asn Pro Ala Leu Gln Leu Ile
1               5                   10                  15

<210> SEQ ID NO 102
<211> LENGTH: 15
<212> TYPE: PRT
<213> ORGANISM: Bougainvillea spectabilis

<400> SEQUENCE: 102

Gln Cys Thr Thr Ile Asn Pro Ala Leu Gln Leu Ile Ser Pro Ser
1               5                   10                  15

<210> SEQ ID NO 103
<211> LENGTH: 15
<212> TYPE: PRT
<213> ORGANISM: Bougainvillea spectabilis

<400> SEQUENCE: 103

Thr Ile Asn Pro Ala Leu Gln Leu Ile Ser Pro Ser Asn Asp Pro
1               5                   10                  15

<210> SEQ ID NO 104
<211> LENGTH: 15
<212> TYPE: PRT
<213> ORGANISM: Bougainvillea spectabilis

<400> SEQUENCE: 104

Pro Ala Leu Gln Leu Ile Ser Pro Ser Asn Asp Pro Trp Val Val
1               5                   10                  15

<210> SEQ ID NO 105
<211> LENGTH: 15
<212> TYPE: PRT
<213> ORGANISM: Bougainvillea spectabilis

<400> SEQUENCE: 105

Gln Leu Ile Ser Pro Ser Asn Asp Pro Trp Val Val Asn Lys Val
1               5                   10                  15

<210> SEQ ID NO 106
<211> LENGTH: 15
<212> TYPE: PRT
<213> ORGANISM: Bougainvillea spectabilis

<400> SEQUENCE: 106

Ser Pro Ser Asn Asp Pro Trp Val Val Asn Lys Val Ser Gln Ile
1               5                   10                  15

<210> SEQ ID NO 107
<211> LENGTH: 15
<212> TYPE: PRT
<213> ORGANISM: Bougainvillea spectabilis

<400> SEQUENCE: 107

Asn Asp Pro Trp Val Val Asn Lys Val Ser Gln Ile Ser Pro Asp
1               5                   10                  15
```

```
<210> SEQ ID NO 108
<211> LENGTH: 15
<212> TYPE: PRT
<213> ORGANISM: Bougainvillea spectabilis

<400> SEQUENCE: 108

Trp Val Val Asn Lys Val Ser Gln Ile Ser Pro Asp Met Gly Ile
1               5                   10                  15

<210> SEQ ID NO 109
<211> LENGTH: 15
<212> TYPE: PRT
<213> ORGANISM: Bougainvillea spectabilis

<400> SEQUENCE: 109

Asn Lys Val Ser Gln Ile Ser Pro Asp Met Gly Ile Leu Lys Phe
1               5                   10                  15

<210> SEQ ID NO 110
<211> LENGTH: 15
<212> TYPE: PRT
<213> ORGANISM: Bougainvillea spectabilis

<400> SEQUENCE: 110

Ser Gln Ile Ser Pro Asp Met Gly Ile Leu Lys Phe Lys Ser Ser
1               5                   10                  15

<210> SEQ ID NO 111
<211> LENGTH: 15
<212> TYPE: PRT
<213> ORGANISM: Bougainvillea spectabilis

<400> SEQUENCE: 111

Ser Pro Asp Met Gly Ile Leu Lys Phe Lys Ser Ser Lys Leu Thr
1               5                   10                  15

<210> SEQ ID NO 112
<211> LENGTH: 15
<212> TYPE: PRT
<213> ORGANISM: Bougainvillea spectabilis

<400> SEQUENCE: 112

Met Gly Ile Leu Lys Phe Lys Ser Ser Lys Leu Thr Gln Phe Ala
1               5                   10                  15

<210> SEQ ID NO 113
<211> LENGTH: 15
<212> TYPE: PRT
<213> ORGANISM: Bougainvillea spectabilis

<400> SEQUENCE: 113

Leu Lys Phe Lys Ser Ser Lys Leu Thr Gln Phe Ala Thr Met Ile
1               5                   10                  15

<210> SEQ ID NO 114
<211> LENGTH: 15
<212> TYPE: PRT
<213> ORGANISM: Bougainvillea spectabilis

<400> SEQUENCE: 114

Lys Ser Ser Lys Leu Thr Gln Phe Ala Thr Met Ile Arg Ser Ala
1               5                   10                  15

<210> SEQ ID NO 115
<211> LENGTH: 15
```

-continued

```
<212> TYPE: PRT
<213> ORGANISM: Bougainvillea spectabilis

<400> SEQUENCE: 115

Lys Leu Thr Gln Phe Ala Thr Met Ile Arg Ser Ala Ile Val Glu
1               5                   10                  15

<210> SEQ ID NO 116
<211> LENGTH: 15
<212> TYPE: PRT
<213> ORGANISM: Bougainvillea spectabilis

<400> SEQUENCE: 116

Gln Phe Ala Thr Met Ile Arg Ser Ala Ile Val Glu Asp Leu Asp
1               5                   10                  15

<210> SEQ ID NO 117
<211> LENGTH: 15
<212> TYPE: PRT
<213> ORGANISM: Bougainvillea spectabilis

<400> SEQUENCE: 117

Thr Met Ile Arg Ser Ala Ile Val Glu Asp Leu Asp Gly Asp Glu
1               5                   10                  15

<210> SEQ ID NO 118
<211> LENGTH: 15
<212> TYPE: PRT
<213> ORGANISM: Bougainvillea spectabilis

<400> SEQUENCE: 118

Arg Ser Ala Ile Val Glu Asp Leu Asp Gly Asp Glu Leu Glu Ile
1               5                   10                  15

<210> SEQ ID NO 119
<211> LENGTH: 15
<212> TYPE: PRT
<213> ORGANISM: Bougainvillea spectabilis

<400> SEQUENCE: 119

Ile Val Glu Asp Leu Asp Gly Asp Glu Leu Glu Ile Leu Glu Pro
1               5                   10                  15

<210> SEQ ID NO 120
<211> LENGTH: 15
<212> TYPE: PRT
<213> ORGANISM: Bougainvillea spectabilis

<400> SEQUENCE: 120

Asp Leu Asp Gly Asp Glu Leu Glu Ile Leu Glu Pro Asn Ile Ala
1               5                   10                  15

<210> SEQ ID NO 121
<211> LENGTH: 23
<212> TYPE: DNA
<213> ORGANISM: Artificial Sequence
<220> FEATURE:
<223> OTHER INFORMATION: Primer OL1032

<400> SEQUENCE: 121
cattacaaac gtctaccaag ttt                                        23

<210> SEQ ID NO 122
<211> LENGTH: 24
<212> TYPE: DNA
```

```
<213> ORGANISM: Artificial Sequence
<220> FEATURE:
<223> OTHER INFORMATION: Primer OL1033

<400> SEQUENCE: 122
ttacaaaagt agataagtaa tgtg                                            24

<210> SEQ ID NO 123
<211> LENGTH: 30
<212> TYPE: DNA
<213> ORGANISM: Artificial Sequence
<220> FEATURE:
<223> OTHER INFORMATION: Primer OL1322

<400> SEQUENCE: 123
gatatacata tgaaatacct attgcctacg                                      30

<210> SEQ ID NO 124
<211> LENGTH: 36
<212> TYPE: DNA
<213> ORGANISM: Artificial Sequence
<220> FEATURE:
<223> OTHER INFORMATION: Primer OL1067

<400> SEQUENCE: 124
tgacacagtg ttgtacgctg gttgggcagc gagtaa                               36

<210> SEQ ID NO 125
<211> LENGTH: 36
<212> TYPE: DNA
<213> ORGANISM: Artificial Sequence
<220> FEATURE:
<223> OTHER INFORMATION: Primer OL1068

<400> SEQUENCE: 125
gctgcccaac cagcgtacaa cactgtgtca tttaac                               36

<210> SEQ ID NO 126
<211> LENGTH: 35
<212> TYPE: DNA
<213> ORGANISM: Artificial Sequence
<220> FEATURE:
<223> OTHER INFORMATION: Primer OL1323

<400> SEQUENCE: 126
cgagtgcggc cgctcaatgg tgatggtgat ggtgt                                35

<210> SEQ ID NO 127
<211> LENGTH: 13
<212> TYPE: PRT
<213> ORGANISM: Influenza virus

<400> SEQUENCE: 127

Pro Lys Tyr Val Lys Gln Asn Thr Leu Lys Leu Ala Thr
1               5                   10

<210> SEQ ID NO 128
<211> LENGTH: 15
<212> TYPE: PRT
<213> ORGANISM: Chlamydia sp.

<400> SEQUENCE: 128

Lys Val Val Asp Gln Ile Lys Lys Ile Ser Lys Pro Val Gln His
1               5                   10                  15
```

-continued

```
<210> SEQ ID NO 129
<211> LENGTH: 250
<212> TYPE: PRT
<213> ORGANISM: Bougainvillea spectabilis

<400> SEQUENCE: 129

Tyr Asn Thr Val Ser Phe Asn Leu Gly Glu Ala Tyr Glu Tyr Pro Thr
1               5                   10                  15

Phe Ile Gln Asp Leu Arg Asn Glu Leu Ala Lys Gly Thr Pro Val Cys
            20                  25                  30

Gln Leu Pro Val Thr Leu Gln Thr Ile Ala Asp Asp Lys Arg Phe Val
        35                  40                  45

Leu Val Asp Ile Thr Thr Thr Ser Lys Lys Thr Val Lys Val Ala Ile
    50                  55                  60

Asp Val Thr Asp Val Ala Val Val Gly Tyr Gln Asp Lys Trp Asp Gly
65                  70                  75                  80

Lys Asp Arg Ala Val Phe Leu Asp Lys Val Pro Thr Val Ala Thr Ser
                85                  90                  95

Lys Leu Phe Pro Gly Val Thr Asn Arg Val Thr Leu Thr Phe Asp Gly
            100                 105                 110

Ser Tyr Gln Lys Leu Val Asn Ala Ala Lys Val Asp Arg Lys Asp Leu
        115                 120                 125

Glu Leu Gly Val Tyr Lys Leu Glu Phe Ser Ile Glu Ala Ile His Gly
    130                 135                 140

Lys Thr Ile Asn Gly Gln Glu Ile Ala Lys Phe Phe Leu Ile Val Ile
145                 150                 155                 160

Gln Met Val Ser Glu Ala Ala Arg Phe Lys Tyr Ile Glu Thr Glu Val
                165                 170                 175

Val Asp Arg Gly Leu Tyr Gly Ser Phe Lys Pro Asn Phe Lys Val Leu
            180                 185                 190

Asn Leu Glu Asn Asn Trp Gly Asp Ile Ser Asp Ala Ile His Lys Ser
        195                 200                 205

Ser Pro Gln Cys Thr Thr Ile Asn Pro Ala Leu Gln Leu Ile Ser Pro
    210                 215                 220

Ser Asn Asp Pro Trp Val Val Asn Lys Val Ser Gln Ile Ser Pro Asp
225                 230                 235                 240

Met Gly Ile Leu Lys Phe Lys Ser Ser Lys
                245                 250
```